US008017727B2

(12) United States Patent
O'Mahony et al.

(10) Patent No.: US 8,017,727 B2
(45) **Date of Patent: *Sep. 13, 2011**

(54) CONJUGATES OF MEMBRANE TRANSLOCATING AGENTS AND PHARMACEUTICALLY ACTIVE AGENTS

(75) Inventors: Daniel O'Mahony, Blackrock (IE); Imelda Lambkin, Sutton (IE); Clemencia Pinilla, Cardiff, CA (US); Richard Houghten, Solana Beach, CA (US)

(73) Assignee: Merrion Research III Limited, Dublin 2 (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/645,922

(22) Filed: Dec. 23, 2009

(65) Prior Publication Data

US 2010/0168381 A1 Jul. 1, 2010

Related U.S. Application Data

(63) Continuation of application No. 11/303,372, filed on Dec. 16, 2005, now Pat. No. 7,638,599, which is a continuation of application No. 10/955,656, filed on Sep. 30, 2004, now abandoned, which is a continuation of application No. 10/126,845, filed on Apr. 19, 2002, now abandoned, which is a continuation-in-part of application No. 09/671,089, filed on Sep. 27, 2000, now Pat. No. 6,780,846.

(60) Provisional application No. 60/156,246, filed on Sep. 27, 1999, provisional application No. 60/287,786, filed on Apr. 30, 2001.

(51) Int. Cl.
*A61K 38/00* (2006.01)
*A61K 38/04* (2006.01)

(52) U.S. Cl. ....................................... 530/326; 530/330

(58) Field of Classification Search ........................ None
See application file for complete search history.

(56) References Cited

U.S. PATENT DOCUMENTS

| | | | | |
|---|---|---|---|---|
| 4,244,946 | A | 1/1981 | Rivier et al. | |
| 4,305,872 | A | 12/1981 | Johnston et al. | |
| 4,316,891 | A | 2/1982 | Guillemin et al. | |
| 4,675,189 | A | 6/1987 | Kent et al. | |
| 4,847,240 | A | 7/1989 | Ryser et al. | |
| 5,449,616 | A * | 9/1995 | Campbell et al. | 435/325 |
| 6,117,632 | A | 9/2000 | O'Mahony | |
| 6,248,558 | B1 | 6/2001 | Lin et al. | |
| 6,346,613 | B1 | 2/2002 | O'Mahony et al. | |
| 6,361,938 | B1 | 3/2002 | O'Mahony et al. | |
| 6,380,370 | B1 * | 4/2002 | Doucette-Stamm et al. | 536/23.1 |
| 6,423,334 | B1 | 7/2002 | Brayden et al. | |
| 6,451,601 | B1 | 9/2002 | Baetge et al. | |

FOREIGN PATENT DOCUMENTS

| | | | |
|---|---|---|---|
| WO | WO 98/47913 | * | 10/1998 |
| WO | WO 98/47913 | A2 | 10/1998 |
| WO | WO 98/51325 | | 11/1998 |
| WO | WO 99/49879 | | 10/1999 |
| WO | WO 99/64449 | | 12/1999 |
| WO | WO 99/67284 | | 12/1999 |
| WO | WO 01/13957 | A2 | 3/2001 |
| WO | WO 01/27154 | * | 4/2001 |
| WO | WO 01/27154 | A2 | 4/2001 |
| WO | WO 02/088318 | A2 | 11/2002 |

OTHER PUBLICATIONS

Lin et al., Journal of Biological Chemistry, 1996, vol. 271, p. 5305.*
Rojas et al. Nature Biotechnology, 1998, vol. 16, p. 370.*
Examination Report corresponding to European Patent Application No. 03726420.7 dated Mar. 14, 2011.
Merrifield, R., "Solid Phase Peptide Synthesis. I. The Synthesis of a Tetrapeptide", J. Am. Chem. Soc., vol. 85, Jul. 20, 1963, pp. 2149-2154.
Sun, T. et al.; "Topography of Ribosomal Proteins of the *Escherichia coli* 30S Submit as Studied with the Reversible Cross-Linking Reagent Methyl 4-Mercaptobutyrimidate†" Biochemistry; vol. 13; No. 11; 1974; pp. 2334-2340.
Lomant, A.J., et al.; "Chemical Probes of Extended Biological Structures: Synthesis and Properties of the Cleavable Protein Cross-linking Reagent [$^{35}$S] Dithiobis (succinimidyl propionate)"; J. Mol. Biol.; 104; 1976; pp. 243-261.
Carlsson, J., et al.; "Protein Thiolation and Reversible Protein-Protein Conjugation"; Biochemistry J.; 173; 1978; pp. 723-737.
Jue, R., et al.; "Addition of Sulfhydryl Groups to *Escherichia coli* Ribosomes by Protein Modification with 2-Iminothiolane (Methyl 4-Mercaptobutyrimidate)†" Biochem; 1978; vol. 17; pp. 5399-5405.
Hutchison, C., et al.; "Mutagenesis at a Specific Position in a DNA Sequence"; The Journal of Biological Chemistry; vol, 253; No. 18; Sep. 25, 1978; pp. 6551-6560.
Yoshitake, et al.; Conjugation of Glucose Oxidase from *Aspergillus niger* and Rabbit Antibodies Using N-Hydroxysucinimide Ester of N-(4-Carboxycyclohexylmethyl)-Maleimide, Eur. J. Biochem; 101; 1979; pp. 395-399.
Liu, F., et al.; "New Procedures for Preparation and Isolation of Conjugates of Proteins and a Synthetic Copolymer of D-Amino Acids and Immunochemical Characterization of Such Conjugates"; Biochemistry; 1979; vol. 18; No. 4; pp. 690-697.
Pilch, P., et al.; "Interaction of Cross-Linking Agents with the Insulin Effector System of Isolated Fat Cells"; The Journal of Biological Chemistry, vol. 254; 1979; pp. 3375-3381.
Youle, R., et al.; "Anti-Thy 1.2 monoclonal antibody linked to ricin is a potent cell-type-specific toxin"; Proc. Natl. Acad. Sci. USA; vol. 77; No. 9; Sep. 1980; pp. 5483-5486.
Ranger and Peppas, "Mathematical Modeling of Diffusion Processes in Drug Delivery Polymeric Systems", J. Macromol. Sci. Rev. Macromol. Chem., Chapter 7, 1983, pp. 203-237.
Märki, W., et al., "Total Solid-Phase Synthesis of Porcine Gut Gastrin Releasing Peptide (GRP), a Mammalian Bombesin", J. Am. Chem. Soc., vol. 103, 1981, pp. 3178-3185.

(Continued)

*Primary Examiner* — Suzanne M. Noakes
(74) *Attorney, Agent, or Firm* — Myers Bigel Sibley & Sajovec, P.A.

(57) ABSTRACT

Membrane translocation peptides, compositions comprising them, chimeric molecules comprising them, and methods of using them to achieve transmembrane transport of various agents.

12 Claims, 6 Drawing Sheets

OTHER PUBLICATIONS

Vale, W., et al.; "Characterization of a 41-Residue Ovine Hypothalamic Peptide that Stimulates Secretion of Corticotropin and β-Endorphin"; Science; vol. 213; Sep. 18, 1981; pp. 1394-1397.

Lerner, R., et al.; "Chemically synthesized peptides predicted from the nucleotide sequence of the hepatitis B virus genome elicit antibodies reactive with the native envelope protein of Dane particles"; Proc. Natl. Acad. Sci. USA; vol. 78; No. 6; Jun. 1981; pp. 3403-3407.

Yoshitake, S., et al.; "Mild and Efficient Conjugation of Rabbit Fab' and Horseradish Peroxidase Using a Maleimide Compound and Its Use for Enzyme Immunoasay"; J. Biochem.; 92; 1982; pp. 1413-1424.

Staros, J., "N-Hydroxysulfosuccinimide Active Esters: Bis(N-hydroxysulfosuccinimide) Esters of Two Dicarboxylic Acids are Hydrophilic, Membrane-Impermeant, Protein Cross-Linkers", Biochemistry; vol. 21; 1982; pp. 3950-3955.

Jung, S., et al.; "Crosslinking of Platewlet Glycoprotein Ib by N-Succinimidyl (4-Azidophenyldithio) Propionate and 3,3'-Dithiobis (Sulfosuccinimidyl Propionate)"; Biochimica Acta; 761; 1983; pp. 152-162.

Hashida, S., et al., "More Useful Maleimide Compounds for the Conjugation of Fab' to Horseradish Peroxidase through Thiol Groups in the Hinge", Journal of Applied Biochemistry, vol. 6, 1984, pp. 56-63.

Levy, R., et al.; "Inhibition of Calcification of Bioprosthetic Heart Valves by Local Controlled-Release Diphosphonate"; Science; vol. 228; Apr. 12, 1985; pp. 190-192.

Cumber, A.J., et al.; "Preparation of Antibody-Toxin Conjugates"; Methods in Enzymology; vol. 112; 1985; pp. 207-225.

Blättler, W., et al.;"New Heterobifunctional Protein Cross-Linking Reagent that Forms an Acid-Labile Link"; Biochemistry; 1985; vol. 24; pp. 1517-1524.

Rink, H.; "Solid-Phase Synthesis of Protected Peptide Fragments using a trialkoxy-Diphenyl-Methylester Resin".; Tetrahedron Letters; vol. 28; No. 33; 1987; pp. 3787-3790.

Hamada, H., et al.; "Determination of Membrane Antigens by a Covalent Crosslinking Method with Monoclonal Antibodies"; Analytical Biochemistry; 160; 1987; pp. 483-488.

Novick, et al.; "The Human Interferon-γ Receptor"; The Journal of Biological Chemistry; vol. 262; No. 18; Jun. 25, 1987; pp. 8483-8487.

During, M., et al.;"Controlled release of Dopamine from a Polymeric Brain Implant: In Vivo Characterization"; Annals of Neurology; vol. 25; No. 4; Apr. 1989; pp. 351-356.

Howard, M., et al.; "Intracerebral drug delivery in rats with lesion-induced memory deficits"; J. Neurosurg.; vol. 71; Jul. 1989; pp. 105-112.

Means, G.†, et al., "Chemical Modifications of Proteins: History and Applications", Bioconjugate Chem, vol. 1, 1990, pp. 2-12.

Maniatis, T., Molecular Cloning, A Laboratory Manual, $2^{nd}$ Ed., Cold Spring Harbor Laboratory, Cold Spring Harbor, New York, 1990, pp. 16.1-17.44.

Fong, S., et al., "Scanning Whole Cells with Phage-Display Libraries: Identification of Peptide Ligands that Modulate Cell Function", Drug Development Research, vol. 33, 1994, pp. 64-70.

Lin, Y. ‡, et al.; "Inhibition of Nuclear Translocation of Transcription Factor NK-kappaB by a Synthetic Peptide Containing a Cell Membrane-permeable Motif and Nuclear Localization Sequence" The Journal of Biological Chemistry, vol. 270, No. 24, Jun. 16, 1995, pp. 14255-14258.

Lin, et al., "Role of the Nuclear Localization Sequence in Fibroblast Growth Factor-1-stimulated Mitogenic Pathways", The Journal of Biological Chemistry, vol. 271, No. 10, Mar. 8, 1996, pp. 5305-5308.

Liu, X., et al.; "Identification of a Functionally Important Sequence in the Cytoplasmic Tail of Integrin $\beta_3$ by Using Cell-Permeable Peptide Analogs"; Proc. Natl. Acad. Sci. USA; vol. 93; Oct. 1996; pp. 11819-11824.

Rojas, M., et al.; "Controlling Epidermal Growth Factor (EGF)-stimulated Ras Activation in Intact Cells by a Cell-permeable Peptide Mimicking Phosphorylated EGF Receptor"; The Journal of Biological Chemistry; vol. 271; No. 44; Nov. 1, 1996; pp. 27456-27461.

Fix, J.; "Strategies for Delivery of Peptides Utilizing Absorption-Enhancing Agents"; Journal of Pharmaceutical Sciences; vol. 85; No. 12; Dec. 1996; pp. 1282-1285.

Rojas, M., et al.; "An Alternative to Phyosphotyrosine-Containing Motifs for Binding to an SH2 Domain"; Biochemical and Biophysical Research Communications; 234; 1997; pp. 675-680.

Rojas, M., et al.; "Genetic Engineering of Proteins with Cell Membrane Permeability"; Nature Biotechnology; vol. 16; Apr. 1998; pp. 370-375.

Eason, P.D. et al., "A Potent Oligosaccharyl Transferase Inhibitor that Crosses the Intracellular Endoplasmic Reticulum Membrane", Biochemstry, vol. 38, No. 4, Aug. 1999 pp. 5430-5437.

Nezil, F.A. et al., "Combined Influence of Cholesterol and Synthetic Amphiphillic Peptides upon Bilayer Thickness in Model Membranes", Biophysical Journal, vol. 61, May 1992, pp. 1176-1183.

International Search Report for Application No. PCT/IB/01491, Jul. 1998.

Koltover et al., An Inverted Hexagonal Phase of Cationic Liposome±DNA Complexes Related to DNA Release and Delivery, Science, 281, 78-81, Jul. 1998.

Sun, T., et al.; "Topography of Ribosomal Proteins of the *Escherichia coli* 30S Submit as Studied with the Reversible Cross-Linking Reagent Methyl 4-Mercaptobutyrimidate†" Biochemistry; vol. 13; No. 11; 1974; pp. 2334-2340.

Carlsson, J., et al,; "Protein Thiolation and Reversible Protein-Protein Conjugation"; Biochemistry J.; 173; 1978; pp. 723-737.

Peppas, "Mathematical Modeling of Diffusion Processes in Drug Delivery Polymeric Systems", J. Macromol. Sci. Rev. Macromol. Chem. Chapter 7, 1983, pp. 203-237.

Blättler, W., et al.; "New Heterobifunctional Protein Cross-Linking Reagent that Forms an Acid-Labile Link"; Biochemistry; 1985; vol. 24; pp. 1517-1524.

During, M., et al.; "Controlled release of Dopamine from a Polymeric Brain Implant: In Vivo Characterization"; Annals of Neurology; vol. 25; No. 4; Apr. 1989; pp. 351-356.

Sambrook, J. et al., Molecular Cloning, A Laboratory Manual, $2^{nd}$ Ed., Cold Spring Harbor Laboratory, Cold Spring Harbor, New York, 1990, pp. 16.1-17.44.

Fong, S.,et al., "Scanning Whole Cells with Phage-Display Libraries: Identification of Peptide Ligands that Modulate Cell Function", Drug Development Research, vol. 33, 1994, pp. 64-70.

Rojas, M., et al,; "Genetic Engineering of Proteins with Cell Membrane Permeability"; Nature Biotechnology; vol. 16; Apr. 1998; pp. 370-375.

International Search Report for Application No. PCT/IB00/01491, Jul. 1998.

* cited by examiner

Kyte-Doolittle Hydrophathy Plot for ZElan094 (SEQ ID NO: 2)

In vivo Delivery of Insulin by ZElan094-Insulin Nanoparticle Complexes and by Targeting Agent-Insulin Nanoparticle Complexes in the Rat Model Figure 6: Transport of 3H Kappa peptides across Caco-2 monolayers
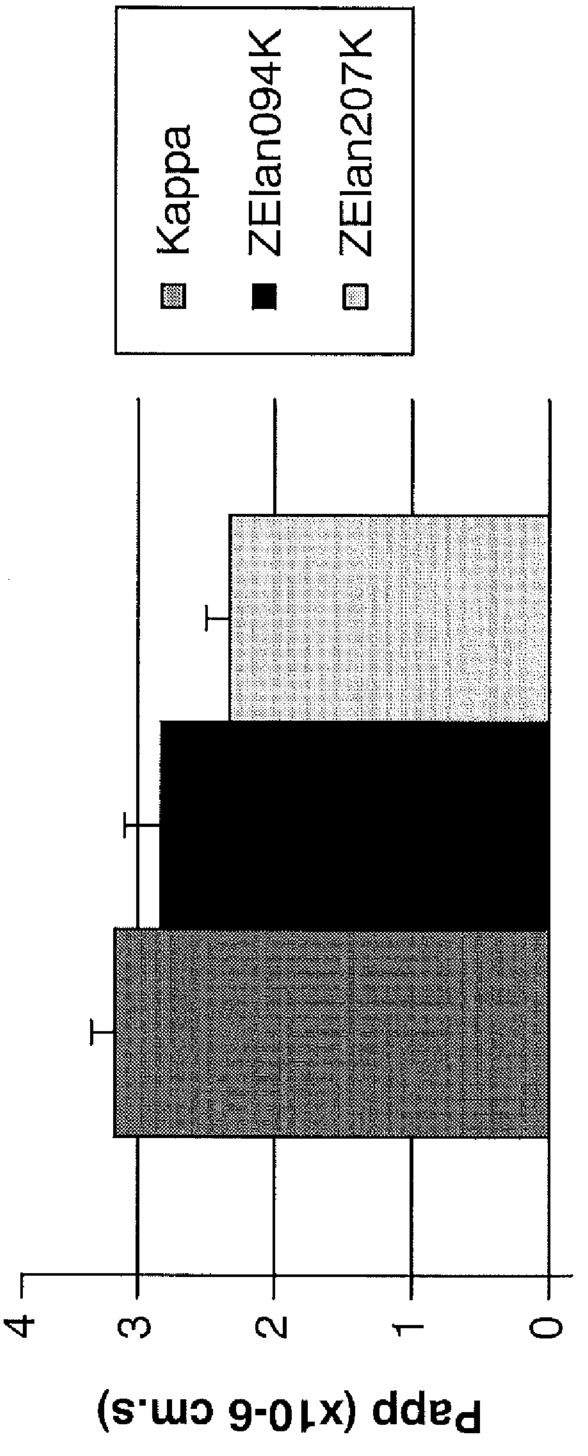

```
                              SEQUENCE LISTING


<160> NUMBER OF SEQ ID NOS: 121

<210> SEQ ID NO 1
<211> LENGTH: 12
<212> TYPE: PRT
<213> ORGANISM: Artificial Sequence
<220> FEATURE:
<223> OTHER INFORMATION: membrane translocating peptide

<400> SEQUENCE: 1

Ala Ala Val Leu Leu Pro Val Leu Leu Ala Ala Pro
1               5                   10


<210> SEQ ID NO 2
<211> LENGTH: 15
<212> TYPE: PRT
<213> ORGANISM: Artificial Sequence
<220> FEATURE:
<223> OTHER INFORMATION: membrane translocating peptide

<400> SEQUENCE: 2

Lys Lys Ala Ala Ala Val Leu Leu Pro Val Leu Leu Ala Ala Pro
1               5                   10                  15


<210> SEQ ID NO 3
<211> LENGTH: 15
<212> TYPE: PRT
<213> ORGANISM: Artificial Sequence
<220> FEATURE:
<223> OTHER INFORMATION: membrane translocating peptide
<220> FEATURE:
<221> NAME/KEY: MISC_FEATURE
<222> LOCATION: (15)..(15)
<223> OTHER INFORMATION: Linked to FITC-LC

<400> SEQUENCE: 3

Lys Lys Ala Ala Ala Val Leu Leu Pro Val Leu Leu Ala Ala Pro
1               5                   10                  15


<210> SEQ ID NO 4
<211> LENGTH: 19
<212> TYPE: PRT
<213> ORGANISM: Artificial Sequence
<220> FEATURE:
<223> OTHER INFORMATION: membrane translocating peptide

<400> SEQUENCE: 4

Lys Lys Ala Ala Ala Val Leu Leu Pro Val Leu Leu Ala Ala Pro Arg
1               5                   10                  15

Glu Asp Leu


<210> SEQ ID NO 5
<211> LENGTH: 16
<212> TYPE: PRT
<213> ORGANISM: Artificial Sequence
<220> FEATURE:
```

<223> OTHER INFORMATION: membrane translocating peptide, cyclic internal

<400> SEQUENCE: 5

Lys Lys Cys Ala Ala Val Leu Leu Pro Val Leu Leu Ala Ala Pro Cys
1 5 10 15

<210> SEQ ID NO 6
<211> LENGTH: 13
<212> TYPE: PRT
<213> ORGANISM: Artificial Sequence
<220> FEATURE:
<223> OTHER INFORMATION: membrane translocating peptide, cyclic

<400> SEQUENCE: 6

Cys Ala Ala Val Leu Leu Pro Val Leu Leu Ala Ala Cys
1 5 10

<210> SEQ ID NO 7
<211> LENGTH: 14
<212> TYPE: PRT
<213> ORGANISM: Artificial Sequence
<220> FEATURE:
<223> OTHER INFORMATION: membrane translocating peptide, cyclic internal

<400> SEQUENCE: 7

Lys Lys Cys Ala Ala Val Leu Leu Pro Val Leu Leu Ala Cys
1 5 10

<210> SEQ ID NO 8
<211> LENGTH: 11
<212> TYPE: PRT
<213> ORGANISM: Artificial Sequence
<220> FEATURE:
<223> OTHER INFORMATION: membrane translocating peptide, cyclic

<400> SEQUENCE: 8

Cys Ala Ala Val Leu Leu Pro Val Leu Leu Cys
1 5 10

<210> SEQ ID NO 9
<211> LENGTH: 10
<212> TYPE: PRT
<213> ORGANISM: Artificial Sequence
<220> FEATURE:
<223> OTHER INFORMATION: membrane translocating peptide, cyclic

<400> SEQUENCE: 9

Cys Ala Ala Val Leu Leu Pro Val Leu Cys
1 5 10

<210> SEQ ID NO 10
<211> LENGTH: 13
<212> TYPE: PRT
<213> ORGANISM: Artificial Sequence
<220> FEATURE:
<223> OTHER INFORMATION: membrane translocating peptide, cyclic

<400> SEQUENCE: 10

Cys Ala Val Leu Leu Pro Val Leu Leu Ala Ala Pro Cys
1 5 10

<210> SEQ ID NO 11
<211> LENGTH: 12
<212> TYPE: PRT
<213> ORGANISM: Artificial Sequence
<220> FEATURE:
<223> OTHER INFORMATION: membrane translocating peptide, cyclic

<400> SEQUENCE: 11

Cys Val Leu Leu Pro Val Leu Leu Ala Ala Pro Cys
1 5 10

<210> SEQ ID NO 12
<211> LENGTH: 11
<212> TYPE: PRT
<213> ORGANISM: Artificial Sequence
<220> FEATURE:
<223> OTHER INFORMATION: membrane translocating peptide, cyclic

<400> SEQUENCE: 12

Cys Leu Leu Pro Val Leu Leu Ala Ala Pro Cys
1 5 10

<210> SEQ ID NO 13
<211> LENGTH: 10
<212> TYPE: PRT
<213> ORGANISM: Artificial Sequence
<220> FEATURE:
<223> OTHER INFORMATION: membrane translocating peptide, cyclic

<400> SEQUENCE: 13

Cys Leu Pro Val Leu Leu Ala Ala Pro Cys
1 5 10

<210> SEQ ID NO 14
<211> LENGTH: 12
<212> TYPE: PRT
<213> ORGANISM: Artificial Sequence
<220> FEATURE:
<223> OTHER INFORMATION: membrane translocating peptide

<400> SEQUENCE: 14

Ala Ala Val Leu Leu Pro Val Leu Leu Ala Ala Pro
1 5 10

<210> SEQ ID NO 15
<211> LENGTH: 11
<212> TYPE: PRT
<213> ORGANISM: Artificial Sequence
<220> FEATURE:
<223> OTHER INFORMATION: membrane translocating peptide

<400> SEQUENCE: 15

Ala Ala Val Leu Leu Pro Val Leu Leu Ala Ala
1 5 10

<210> SEQ ID NO 16
<211> LENGTH: 12
<212> TYPE: PRT
<213> ORGANISM: Artificial Sequence
<220> FEATURE:
<223> OTHER INFORMATION: membrane translocating peptide

<400> SEQUENCE: 16

Lys Lys Ala Ala Val Leu Leu Pro Val Leu Leu Ala
1 5 10

<210> SEQ ID NO 17
<211> LENGTH: 9
<212> TYPE: PRT
<213> ORGANISM: Artificial Sequence
<220> FEATURE:
<223> OTHER INFORMATION: membrane translocating peptide

<400> SEQUENCE: 17

Ala Ala Val Leu Leu Pro Val Leu Leu
1 5

<210> SEQ ID NO 18
<211> LENGTH: 8
<212> TYPE: PRT
<213> ORGANISM: Artificial Sequence
<220> FEATURE:
<223> OTHER INFORMATION: membrane translocating peptide

<400> SEQUENCE: 18

Ala Ala Val Leu Leu Pro Val Leu
1 5

<210> SEQ ID NO 19
<211> LENGTH: 11
<212> TYPE: PRT
<213> ORGANISM: Artificial Sequence
<220> FEATURE:
<223> OTHER INFORMATION: membrane translocating peptide

<400> SEQUENCE: 19

Ala Val Leu Leu Pro Val Leu Leu Ala Ala Pro
1 5 10

<210> SEQ ID NO 20
<211> LENGTH: 10
<212> TYPE: PRT
<213> ORGANISM: Artificial Sequence
<220> FEATURE:
<223> OTHER INFORMATION: membrane translocating peptide

<400> SEQUENCE: 20

Val Leu Leu Pro Val Leu Leu Ala Ala Pro
1 5 10

<210> SEQ ID NO 21
<211> LENGTH: 9
<212> TYPE: PRT
<213> ORGANISM: Artificial Sequence
<220> FEATURE:
<223> OTHER INFORMATION: membrane translocating peptide

<400> SEQUENCE: 21

Leu Leu Pro Val Leu Leu Ala Ala Pro
1 5

<210> SEQ ID NO 22
<211> LENGTH: 8
<212> TYPE: PRT
<213> ORGANISM: Artificial Sequence
<220> FEATURE:
<223> OTHER INFORMATION: membrane translocating peptide

<400> SEQUENCE: 22

Leu Pro Val Leu Leu Ala Ala Pro
1 5

<210> SEQ ID NO 23
<211> LENGTH: 17
<212> TYPE: PRT
<213> ORGANISM: Artificial Sequence
<220> FEATURE:
<223> OTHER INFORMATION: membrane translocating peptide

<400> SEQUENCE: 23

Ala Ala Val Leu Leu Pro Val Leu Leu Ala Ala Lys Lys Lys Arg Lys
1 5 10 15

Ala

<210> SEQ ID NO 24
<211> LENGTH: 17
<212> TYPE: PRT
<213> ORGANISM: Artificial Sequence
<220> FEATURE:
<223> OTHER INFORMATION: membrane translocating peptide

<400> SEQUENCE: 24

Lys Lys Lys Arg Lys Ala Ala Ala Ala Val Leu Leu Pro Val Leu Leu
1 5 10 15

Ala

<210> SEQ ID NO 25
<211> LENGTH: 48
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)

<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (48)..(48)
<223> OTHER INFORMATION: n is a, c, g, or t

<400> SEQUENCE: 25
aaraaraarg cngcngcngt nytnytnccn gtnytnytng cngcnccn 48

<210> SEQ ID NO 26
<211> LENGTH: 45
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)

<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (37)..(37)
<223> OTHER INFORMATION: "y is C or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (48)..(48)
<223> OTHER INFORMATION: "n is A or C or G or T"

<400> SEQUENCE: 26
aaraargcng cngcngtnyt nytnccngtn ytnytngcng cnccn 45

<210> SEQ ID NO 27
<211> LENGTH: 60
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)

-continued

<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (37)..(37)
<223> OTHER INFORMATION: "y is C or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (48)..(48)
<223> OTHER INFORMATION: "n is A or C or G or T"
<220> FEATURE:
<221> NAME/KEY: misc_feature
<222> LOCATION: (49)..(49)
<223> OTHER INFORMATION: "m is A or C"
<220> FEATURE:
<221> NAME/KEY: misc_feature
<222> LOCATION: (51)..(51)
<223> OTHER INFORMATION: "n is A or C or G or T"
<220> FEATURE:
<221> NAME/KEY: misc_feature
<222> LOCATION: (54)..(54)
<223> OTHER INFORMATION: "r is A or G"
<220> FEATURE:
<221> NAME/KEY: misc_feature
<222> LOCATION: (57)..(57)
<223> OTHER INFORMATION: "y is C or T"
<220> FEATURE:
<221> NAME/KEY: misc_feature
<222> LOCATION: (58)..(58)
<223> OTHER INFORMATION: "y is C or T"
<220> FEATURE:
<221> NAME/KEY: misc_feature
<222> LOCATION: (60)..(60)
<223> OTHER INFORMATION: "n is A or C or G or T"

<400> SEQUENCE: 27

-continued aaraaraarg cngcngcngt nytnytnccn gtnytnytng cngcnccnmg ngargayytn 60

<210> SEQ ID NO 28
<211> LENGTH: 51
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (12)..(12)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (37)..(37)
<223> OTHER INFORMATION: "y is C or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)

<223> OTHER INFORMATION: "n is A or C or G or T"
<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (48)..(48)
<223> OTHER INFORMATION: "n is A or C or G or T"
<220> FEATURE:
<221> NAME/KEY: misc_feature
<222> LOCATION: (51)..(51)
<223> OTHER INFORMATION: "y is C or T"

<400> SEQUENCE: 28
aaraaraart gygcngcngt nytnytnccn gtnytnytng cngcnccntg y 51

<210> SEQ ID NO 29
<211> LENGTH: 42
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)

<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "y is C or T"

<400> SEQUENCE: 29
aartgygcng cngtnytnyt nccngtnytn ytngcngcnt gy 42

<210> SEQ ID NO 30
<211> LENGTH: 39
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)

<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "y is C or T"

<400> SEQUENCE: 30
aartgygcng cngtnytnyt nccngtnytn ytngcntgy 39

<210> SEQ ID NO 31
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "y is C or T"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)

<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "y is C or T"

<400> SEQUENCE: 31
aartgygcng cngtnytnyt nccngtnytn ytntgy 36

<210> SEQ ID NO 32
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)

<223> OTHER INFORMATION: "y is C or T"

<400> SEQUENCE: 32
aartgygcng cngtnytnyt nccngtnytn tgy 33

<210> SEQ ID NO 33
<211> LENGTH: 42
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)

<223> OTHER INFORMATION: "n is A or C or G or T"
<220> FEATURE:
<221> NAME/KEY: misc_feature
<222> LOCATION: (42)..(42)
<223> OTHER INFORMATION: "y is C or T"

<400> SEQUENCE: 33
aartgygcng tnytnytncc ngtnytnytn gcngcnccnt gy 42

<210> SEQ ID NO 34
<211> LENGTH: 39
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (33)..(36)

<223> OTHER INFORMATION: "n is A or C or G or T"
<220> FEATURE:
<221> NAME/KEY: misc_feature
<222> LOCATION: (39)..(39)
<223> OTHER INFORMATION: "y is C or T"

<400> SEQUENCE: 34
aartgygtny tnytnccngt nytnytngcn gcnccntgy 39

<210> SEQ ID NO 35
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)

<223> OTHER INFORMATION: "y is C or T"

<400> SEQUENCE: 35
aartgyytny tnccngtnyt nytngcngcn ccntgy 36

<210> SEQ ID NO 36
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "y is C or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "y is C or T"

<400> SEQUENCE: 36
aartgyytnc cngtnytnyt ngcngcnccn tgy 33

<210> SEQ ID NO 37
<211> LENGTH: 39
<212> TYPE: DNA
<213> ORGANISM: Artificial Sequence
<220> FEATURE:

<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"

<400> SEQUENCE: 37
aargcngcng tnytnytncc ngtnytnytn gcngcnccn 39

<210> SEQ ID NO 38
<211> LENGTH: 36
<212> TYPE: DNA
<213> ORGANISM: Artificial Sequence
<220> FEATURE:

<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"

<400> SEQUENCE: 38
aargcngcng tnytnytncc ngtnytnytn gcngcn 36

<210> SEQ ID NO 39
<211> LENGTH: 39
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)

<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (31)..(31)
<223> OTHER INFORMATION: "y is C or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (39)..(39)
<223> OTHER INFORMATION: "n is A or C or G or T"

<400> SEQUENCE: 39
aaraaraarg cngcngtnyt nytnccngtn ytnytngcn 39

<210> SEQ ID NO 40
<211> LENGTH: 30
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)

<223> OTHER INFORMATION: "r is A or G"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (28)..(28)
<223> OTHER INFORMATION: "y is C or T"
<220> FEATURE:
<221> NAME/KEY: misc_feature
<222> LOCATION: (30)..(30)
<223> OTHER INFORMATION: "n is A or C or G or T"

<400> SEQUENCE: 40
aargcngcng tnytnytncc ngtnytnytn 30

<210> SEQ ID NO 41
<211> LENGTH: 30
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)

<223> OTHER INFORMATION: “n is A or C or G or T”
<220> FEATURE:
<221> NAME/KEY: misc_feature
<222> LOCATION: (13)..(13)
<223> OTHER INFORMATION: “y is C or T”
<220> FEATURE:
<221> NAME/KEY: misc_feature
<222> LOCATION: (15)..(15)
<223> OTHER INFORMATION: “n is A or C or G or T”
<220> FEATURE:
<221> NAME/KEY: misc_feature
<222> LOCATION: (16)..(16)
<223> OTHER INFORMATION: “y is C or T”
<220> FEATURE:
<221> NAME/KEY: misc_feature
<222> LOCATION: (18)..(18)
<223> OTHER INFORMATION: “n is A or C or G or T”
<220> FEATURE:
<221> NAME/KEY: misc_feature
<222> LOCATION: (21)..(21)
<223> OTHER INFORMATION: “n is A or C or G or T”
<220> FEATURE:
<221> NAME/KEY: misc_feature
<222> LOCATION: (24)..(24)
<223> OTHER INFORMATION: “n is A or C or G or T”
<220> FEATURE:
<221> NAME/KEY: misc_feature
<222> LOCATION: (25)..(25)
<223> OTHER INFORMATION: “y is C or T”
<220> FEATURE:
<221> NAME/KEY: misc_feature
<222> LOCATION: (27)..(27)
<223> OTHER INFORMATION: “n is A or C or G or T”
<220> FEATURE:
<221> NAME/KEY: misc_feature
<222> LOCATION: (28)..(28)
<223> OTHER INFORMATION: “y is C or T”
<220> FEATURE:
<221> NAME/KEY: misc_feature
<222> LOCATION: (30)..(30)
<223> OTHER INFORMATION: “n is A or C or G or T”

<400> SEQUENCE: 41
aargcngcng tnytnytncc ngtnytnytn 30

<210> SEQ ID NO 42
<211> LENGTH: 36
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: “r is A or G”
<220> FEATURE:
<221> NAME/KEY: misc_feature
<222> LOCATION: (6)..(6)
<223> OTHER INFORMATION: “n is A or C or G or T”
<220> FEATURE:
<221> NAME/KEY: misc_feature
<222> LOCATION: (9)..(9)
<223> OTHER INFORMATION: “n is A or C or G or T”
<220> FEATURE:
<221> NAME/KEY: misc_feature
<222> LOCATION: (10)..(10)
<223> OTHER INFORMATION: “y is C or T”
<220> FEATURE:
<221> NAME/KEY: misc_feature
<222> LOCATION: (12)..(12)
<223> OTHER INFORMATION: “n is A or C or G or T”
<220> FEATURE:
<221> NAME/KEY: misc_feature
<222> LOCATION: (13)..(13)
<223> OTHER INFORMATION: “y is C or T”
<220> FEATURE:
<221> NAME/KEY: misc_feature
<222> LOCATION: (15)..(15)

<223> OTHER INFORMATION: "n is A or C or G or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (25)..(25)
<223> OTHER INFORMATION: "y is C or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"
<220> FEATURE:
<221> NAME/KEY: misc_feature
<222> LOCATION: (36)..(36)
<223> OTHER INFORMATION: "n is A or C or G or T"

<400> SEQUENCE: 42
aargcngtny tnytnccngt nytnytngcn gcnccn 36

<210> SEQ ID NO 43
<211> LENGTH: 33
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (10)..(10)
<223> OTHER INFORMATION: "y is C or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)

<223> OTHER INFORMATION: "n is A or C or G or T"
<220> FEATURE:
<221> NAME/KEY: misc_feature
<222> LOCATION: (19)..(19)
<223> OTHER INFORMATION: "y is C or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (22)..(22)
<223> OTHER INFORMATION: "y is C or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)
<223> OTHER INFORMATION: "n is A or C or G or T"

<400> SEQUENCE: 43
aargtnytny tnccngtnyt nytngcngcn ccn 33

<210> SEQ ID NO 44
<211> LENGTH: 30
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (1)..(1)
<223> OTHER INFORMATION: "r is A or G"
<220> FEATURE:
<221> NAME/KEY: misc_feature
<222> LOCATION: (4)..(4)
<223> OTHER INFORMATION: "y is C or T"
<220> FEATURE:
<221> NAME/KEY: misc_feature
<222> LOCATION: (6)..(6)
<223> OTHER INFORMATION: "n is for A or C or G or T"
<220> FEATURE:
<221> NAME/KEY: misc_feature
<222> LOCATION: (7)..(7)
<223> OTHER INFORMATION: "y is C or T"
<220> FEATURE:
<221> NAME/KEY: misc_feature
<222> LOCATION: (9)..(9)
<223> OTHER INFORMATION: "n is for A or C or G or T"
<220> FEATURE:
<221> NAME/KEY: misc_feature
<222> LOCATION: (12)..(12)
<223> OTHER INFORMATION: "n is for A or C or G or T"
<220> FEATURE:
<221> NAME/KEY: misc_feature
<222> LOCATION: (15)..(15)
<223> OTHER INFORMATION: "n is for A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is for A or C or G or T"
<220> FEATURE:
<221> NAME/KEY: misc_feature
<222> LOCATION: (19)..(19)

<223> OTHER INFORMATION: "y is C or T"
<220> FEATURE:
<221> NAME/KEY: misc_feature
<222> LOCATION: (21)..(21)
<223> OTHER INFORMATION: "n is for A or C or G or T"
<220> FEATURE:
<221> NAME/KEY: misc_feature
<222> LOCATION: (24)..(24)
<223> OTHER INFORMATION: "n is for A or C or G or T"
<220> FEATURE:
<221> NAME/KEY: misc_feature
<222> LOCATION: (27)..(27)
<223> OTHER INFORMATION: "n is for A or C or G or T"
<220> FEATURE:
<221> NAME/KEY: misc_feature
<222> LOCATION: (30)..(30)
<223> OTHER INFORMATION: "n is for A or C or G or T"

<400> SEQUENCE: 44
aarytnytnc cngtnytnyt ngcngcnccn 30

<210> SEQ ID NO 45
<211> LENGTH: 27
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (1)..(1)
<223> OTHER INFORMATION: "r is A or G"
<220> FEATURE:
<221> NAME/KEY: misc_feature
<222> LOCATION: (4)..(4)
<223> OTHER INFORMATION: "y is C or T"
<220> FEATURE:
<221> NAME/KEY: misc_feature
<222> LOCATION: (6)..(6)
<223> OTHER INFORMATION: "n is A or C or G or T"
<220> FEATURE:
<221> NAME/KEY: misc_feature
<222> LOCATION: (9)..(9)
<223> OTHER INFORMATION: "n is A or C or G or T"
<220> FEATURE:
<221> NAME/KEY: misc_feature
<222> LOCATION: (12)..(12)
<223> OTHER INFORMATION: "n is A or C or G or T"
<220> FEATURE:
<221> NAME/KEY: misc_feature
<222> LOCATION: (13)..(13)
<223> OTHER INFORMATION: "y is C or T"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (16)..(16)
<223> OTHER INFORMATION: "y is C or T"
<220> FEATURE:
<221> NAME/KEY: misc_feature
<222> LOCATION: (18)..(18)
<223> OTHER INFORMATION: "n is A or C or G or T"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"

<400> SEQUENCE: 45
aarytnccng tnytnytngc ngcnccn 27

<210> SEQ ID NO 46
<211> LENGTH: 53
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (5)..(5)
<223> OTHER INFORMATION: "n is A or C or G or T"
<220> FEATURE:
<221> NAME/KEY: misc_feature
<222> LOCATION: (8)..(8)
<223> OTHER INFORMATION: "n is A or C or G or T"
<220> FEATURE:
<221> NAME/KEY: misc_feature
<222> LOCATION: (11)..(11)
<223> OTHER INFORMATION: "n is A or C or G or T"
<220> FEATURE:
<221> NAME/KEY: misc_feature
<222> LOCATION: (12)..(12)
<223> OTHER INFORMATION: "y is C or T"
<220> FEATURE:
<221> NAME/KEY: misc_feature
<222> LOCATION: (14)..(14)
<223> OTHER INFORMATION: "n is A or C or G or T"
<220> FEATURE:
<221> NAME/KEY: misc_feature
<222> LOCATION: (15)..(15)
<223> OTHER INFORMATION: "y is C or T"
<220> FEATURE:
<221> NAME/KEY: misc_feature
<222> LOCATION: (17)..(17)
<223> OTHER INFORMATION: "n is A or C or G or T"
<220> FEATURE:
<221> NAME/KEY: misc_feature
<222> LOCATION: (20)..(20)
<223> OTHER INFORMATION: "n is A or C or G or T"
<220> FEATURE:
<221> NAME/KEY: misc_feature
<222> LOCATION: (23)..(23)
<223> OTHER INFORMATION: "n is A or C or G or T"
<220> FEATURE:
<221> NAME/KEY: misc_feature
<222> LOCATION: (24)..(24)
<223> OTHER INFORMATION: "y is C or T"
<220> FEATURE:
<221> NAME/KEY: misc_feature
<222> LOCATION: (26)..(26)
<223> OTHER INFORMATION: "n is A or C or G or T"
<220> FEATURE:
<221> NAME/KEY: misc_feature
<222> LOCATION: (27)..(27)
<223> OTHER INFORMATION: "y is C or T"
<220> FEATURE:
<221> NAME/KEY: misc_feature
<222> LOCATION: (29)..(29)
<223> OTHER INFORMATION: "n is A or C or G or T"
<220> FEATURE:
<221> NAME/KEY: misc_feature
<222> LOCATION: (32)..(32)
<223> OTHER INFORMATION: "n is A or C or G or T"
<220> FEATURE:
<221> NAME/KEY: misc_feature
<222> LOCATION: (35)..(35)
<223> OTHER INFORMATION: "n is A or C or G or T"
<220> FEATURE:
<221> NAME/KEY: misc_feature
<222> LOCATION: (38)..(38)
<223> OTHER INFORMATION: "r is A or G"
<220> FEATURE:
<221> NAME/KEY: misc_feature
<222> LOCATION: (41)..(41)

<223> OTHER INFORMATION: "r is A or G"
<220> FEATURE:
<221> NAME/KEY: misc_feature
<222> LOCATION: (44)..(44)
<223> OTHER INFORMATION: "r is A or G"
<220> FEATURE:
<221> NAME/KEY: misc_feature
<222> LOCATION: (45)..(45)
<223> OTHER INFORMATION: "m is A or C"
<220> FEATURE:
<221> NAME/KEY: misc_feature
<222> LOCATION: (47)..(47)
<223> OTHER INFORMATION: "n is A or C or G or T"
<220> FEATURE:
<221> NAME/KEY: misc_feature
<222> LOCATION: (50)..(50)
<223> OTHER INFORMATION: "r is A or G"
<220> FEATURE:
<221> NAME/KEY: misc_feature
<222> LOCATION: (53)..(53)
<223> OTHER INFORMATION: "n is A or C or G or T"

<400> SEQUENCE: 46
aarcngcngt nytnytnccn gtnytnytng cngcnaaraa raarmgnaar gcn 53

<210> SEQ ID NO 47
<211> LENGTH: 54
<212> TYPE: DNA
<213> ORGANISM: Artificial Sequence
<220> FEATURE:
<223> OTHER INFORMATION: encodes membrane translocating peptide
<220> FEATURE:
<221> NAME/KEY: misc_feature
<222> LOCATION: (3)..(3)
<223> OTHER INFORMATION: "r is A or G"
<220> FEATURE:
<221> NAME/KEY: misc_feature
<222> LOCATION: (6)..(6)
<223> OTHER INFORMATION: "r is A or G"
<220> FEATURE:
<221> NAME/KEY: misc_feature
<222> LOCATION: (9)..(9)
<223> OTHER INFORMATION: "r is A or G"
<220> FEATURE:
<221> NAME/KEY: misc_feature
<222> LOCATION: (12)..(12)
<223> OTHER INFORMATION: "r is A or G"
<220> FEATURE:
<221> NAME/KEY: misc_feature
<222> LOCATION: (13)..(13)
<223> OTHER INFORMATION: "m is A or C"
<220> FEATURE:
<221> NAME/KEY: misc_feature
<222> LOCATION: (15)..(15)
<223> OTHER INFORMATION: "n is A or C or G or T"
<220> FEATURE:
<221> NAME/KEY: misc_feature
<222> LOCATION: (18)..(18)
<223> OTHER INFORMATION: "r is A or G"
<220> FEATURE:
<221> NAME/KEY: misc_feature
<222> LOCATION: (21)..(21)
<223> OTHER INFORMATION: "n is A or C or G or T"
<220> FEATURE:
<221> NAME/KEY: misc_feature
<222> LOCATION: (24)..(24)
<223> OTHER INFORMATION: "n is A or C or G or T"
<220> FEATURE:
<221> NAME/KEY: misc_feature
<222> LOCATION: (27)..(27)
<223> OTHER INFORMATION: "n is A or C or G or T"
<220> FEATURE:
<221> NAME/KEY: misc_feature
<222> LOCATION: (30)..(30)
<223> OTHER INFORMATION: "n is A or C or G or T"
<220> FEATURE:
<221> NAME/KEY: misc_feature
<222> LOCATION: (33)..(33)

<223> OTHER INFORMATION: "n is A or C or G or T"
<220> FEATURE:
<221> NAME/KEY: misc_feature
<222> LOCATION: (34)..(34)
<223> OTHER INFORMATION: "y is C or T"
<220> FEATURE:
<221> NAME/KEY: misc_feature
<222> LOCATION: (36)..(36)
<223> OTHER INFORMATION: "n is A or C or G or T"
<220> FEATURE:
<221> NAME/KEY: misc_feature
<222> LOCATION: (37)..(37)
<223> OTHER INFORMATION: "y is C or T"
<220> FEATURE:
<221> NAME/KEY: misc_feature
<222> LOCATION: (39)..(39)
<223> OTHER INFORMATION: "n is A or C or G or T"
<220> FEATURE:
<221> NAME/KEY: misc_feature
<222> LOCATION: (42)..(42)
<223> OTHER INFORMATION: "n is A or C or G or T"
<220> FEATURE:
<221> NAME/KEY: misc_feature
<222> LOCATION: (45)..(45)
<223> OTHER INFORMATION: "n is A or C or G or T"
<220> FEATURE:
<221> NAME/KEY: misc_feature
<222> LOCATION: (46)..(46)
<223> OTHER INFORMATION: "y is C or T"
<220> FEATURE:
<221> NAME/KEY: misc_feature
<222> LOCATION: (48)..(48)
<223> OTHER INFORMATION: "n is A or C or G or T"
<220> FEATURE:
<221> NAME/KEY: misc_feature
<222> LOCATION: (49)..(49)
<223> OTHER INFORMATION: "y is C or T"
<220> FEATURE:
<221> NAME/KEY: misc_feature
<222> LOCATION: (51)..(51)
<223> OTHER INFORMATION: "n is A or C or G or T"
<220> FEATURE:
<221> NAME/KEY: misc_feature
<222> LOCATION: (54)..(54)
<223> OTHER INFORMATION: "n is A or C or G or T"

<400> SEQUENCE: 47
aaraaraara armgnaargc ngcngcngcn gtnytnytnc cngtnytnyt ngcn 54

<210> SEQ ID NO 48
<211> LENGTH: 16
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 48

Lys Lys Lys Ala Ala Ala Val Leu Leu Pro Val Leu Leu Ala Ala Pro
1 5 10 15

<210> SEQ ID NO 49
<211> LENGTH: 44
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 49

Lys Ser Asp His Ala Leu Gly Thr Asn Leu Arg Ser Asp Asn Ala Lys
1 5 10 15

Glu Pro Gly Asp Tyr Asn Cys Cys Gly Asn Gly Asn Ser Thr Gly Arg
20 25 30

Lys Val Phe Asn Arg Arg Arg Ser Ala Ile Pro Tyr
35 40

<210> SEQ ID NO 50
<211> LENGTH: 15
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 50

Lys Pro Gly Asp Tyr Asn Cys Cys Gly Asn Gly Asn Ser Thr Gly
1 5 10 15

<210> SEQ ID NO 51
<211> LENGTH: 41
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 51

Lys Leu Ser Thr Pro Pro Ser Arg Glu Ala Tyr Ser Arg Pro Tyr Ser
1 5 10 15

Val Asp Ser Asp Ser Asp Thr Asn Ala Lys His Ser Ser His Asn Arg
20 25 30

Arg Leu Arg Thr Arg Ser Arg Pro Asn
35 40

<210> SEQ ID NO 52
<211> LENGTH: 18
<212> TYPE: PRT
<213> ORGANISM: Artificial Sequence
<220> FEATURE:
<223> OTHER INFORMATION: dansylated cyclic D form peptide
<220> FEATURE:
<221> NAME/KEY: MOD_RES
<222> LOCATION: (1)..(1)
<223> OTHER INFORMATION: dansylated
<220> FEATURE:
<221> NAME/KEY: MISC_FEATURE
<222> LOCATION: (3)..(3)
<223> OTHER INFORMATION: D form amino acid
<220> FEATURE:
<221> NAME/KEY: MISC_FEATURE
<222> LOCATION: (7)..(7)
<223> OTHER INFORMATION: D form amino acid
<220> FEATURE:
<221> NAME/KEY: MISC_FEATURE
<222> LOCATION: (11)..(11)
<223> OTHER INFORMATION: D form amino acid
<220> FEATURE:
<221> NAME/KEY: MISC_FEATURE
<222> LOCATION: (13)..(13)
<223> OTHER INFORMATION: D form amino acid
<220> FEATURE:
<221> NAME/KEY: MISC_FEATURE
<222> LOCATION: (14)..(14)

<223> OTHER INFORMATION: D form amino acid

<400> SEQUENCE: 52

Lys Lys Thr Arg Lys Ser Ser Arg Ser Asn Pro Arg Gly Arg Arg His
1 5 10 15

Pro Gly

<210> SEQ ID NO 53
<211> LENGTH: 16
<212> TYPE: PRT
<213> ORGANISM: Artificial Sequence
<220> FEATURE:
<223> OTHER INFORMATION: D form retroinversion peptide
<220> FEATURE:
<221> NAME/KEY: MOD_RES
<222> LOCATION: (1)..(1)
<223> OTHER INFORMATION: dansylated
<220> FEATURE:
<221> NAME/KEY: MISC_FEATURE
<222> LOCATION: (2)..(16)
<223> OTHER INFORMATION: D form amino acid

<400> SEQUENCE: 53

Lys Arg Thr Arg Leu Arg Arg Asn His Ser Ser His Lys Ala Asn Thr
1 5 10 15

<210> SEQ ID NO 54
<211> LENGTH: 16
<212> TYPE: PRT
<213> ORGANISM: Artificial Sequence
<220> FEATURE:
<223> OTHER INFORMATION: dansylated membrane translocating peptide
<220> FEATURE:
<221> NAME/KEY: MOD_RES
<222> LOCATION: (1)..(1)
<223> OTHER INFORMATION: dansylated

<400> SEQUENCE: 54

Lys Thr Asn Ala Lys His Ser Ser His Asn Arg Arg Leu Arg Thr Arg
1 5 10 15

<210> SEQ ID NO 55
<211> LENGTH: 12
<212> TYPE: PRT
<213> ORGANISM: Artificial Sequence
<220> FEATURE:
<223> OTHER INFORMATION: dansylated cyclic peptide
<220> FEATURE:
<221> NAME/KEY: MOD_RES
<222> LOCATION: (1)..(1)
<223> OTHER INFORMATION: dansylated

<400> SEQUENCE: 55

Lys Lys Thr Asn Ala Lys His Ser Ser His Asn Arg
1 5 10

<210> SEQ ID NO 56
<211> LENGTH: 16
<212> TYPE: PRT
<213> ORGANISM: Artificial Sequence
<220> FEATURE:
<223> OTHER INFORMATION: dansylated peptide, cyclic internal
<220> FEATURE:
<221> NAME/KEY: MOD_RES
<222> LOCATION: (1)..(1)
<223> OTHER INFORMATION: dansylated

<400> SEQUENCE: 56

Lys Thr Asn Ala Lys His Ser Ser Cys Asn Arg Arg Leu Arg Cys Arg
1 5 10 15

<210> SEQ ID NO 57
<211> LENGTH: 267
<212> TYPE: PRT
<213> ORGANISM: Homo sapiens

<400> SEQUENCE: 57

```
Met Pro Arg Ser Cys Cys Ser Arg Ser Gly Ala Leu Leu Leu Ala Leu
1               5                   10                  15

Leu Leu Gln Ala Ser Met Glu Val Arg Gly Trp Cys Leu Glu Ser Ser
            20                  25                  30

Gln Cys Gln Asp Leu Thr Thr Glu Ser Asn Leu Leu Glu Cys Ile Arg
        35                  40                  45

Ala Cys Lys Pro Asp Leu Ser Ala Glu Thr Pro Met Phe Pro Gly Asn
    50                  55                  60

Gly Asp Glu Gln Pro Leu Thr Glu Asn Pro Arg Lys Tyr Val Met Gly
65                  70                  75                  80

His Phe Arg Trp Asp Arg Phe Gly Arg Arg Asn Ser Ser Ser Ser Gly
                85                  90                  95

Ser Ser Gly Ala Gly Gln Lys Arg Glu Asp Val Ser Ala Gly Glu Asp
            100                 105                 110

Cys Gly Pro Leu Pro Glu Gly Gly Pro Glu Pro Arg Ser Asp Gly Ala
        115                 120                 125

Lys Pro Gly Pro Arg Glu Gly Lys Arg Ser Tyr Ser Met Glu His Phe
    130                 135                 140

Arg Trp Gly Lys Pro Val Gly Lys Lys Arg Arg Pro Val Lys Val Tyr
145                 150                 155                 160

Pro Asn Gly Ala Glu Asp Glu Ser Ala Glu Ala Phe Pro Leu Glu Phe
                165                 170                 175

Lys Arg Glu Leu Thr Gly Gln Arg Leu Arg Glu Gly Asp Gly Pro Asp
            180                 185                 190

Gly Pro Ala Asp Asp Gly Ala Gly Ala Gln Ala Asp Leu Glu His Ser
        195                 200                 205

Leu Leu Val Ala Ala Glu Lys Lys Asp Glu Gly Pro Tyr Arg Met Glu
    210                 215                 220

His Phe Arg Trp Gly Ser Pro Pro Lys Asp Lys Arg Tyr Gly Gly Phe
225                 230                 235                 240

Met Thr Ser Glu Lys Ser Gln Thr Pro Leu Val Thr Leu Phe Lys Asn
                245                 250                 255

Ala Ile Ile Lys Asn Ala Tyr Lys Lys Gly Glu
            260                 265
```

<210> SEQ ID NO 58
<211> LENGTH: 267
<212> TYPE: PRT
<213> ORGANISM: Homo sapiens

<400> SEQUENCE: 58

```
Met Ala Arg Phe Leu Thr Leu Cys Thr Trp Leu Leu Leu Leu Gly Pro
1               5                   10                  15

Gly Leu Leu Ala Thr Val Arg Ala Glu Cys Ser Gln Asp Cys Ala Thr
            20                  25                  30

Cys Ser Tyr Arg Leu Val Arg Pro Ala Asp Ile Asn Phe Leu Ala Cys
        35                  40                  45

Val Met Glu Cys Glu Gly Lys Leu Pro Ser Leu Lys Ile Trp Glu Thr
    50                  55                  60
```

```
Cys Lys Glu Leu Leu Gln Leu Ser Lys Pro Glu Leu Pro Gln Asp Gly
65                  70                  75                  80

Thr Ser Thr Leu Arg Glu Asn Ser Lys Pro Glu Glu Ser His Leu Leu
                85                  90                  95

Ala Lys Arg Tyr Gly Gly Phe Met Lys Arg Tyr Gly Gly Phe Met Lys
            100                 105                 110

Lys Met Asp Glu Leu Tyr Pro Met Glu Pro Glu Glu Glu Ala Asn Gly
        115                 120                 125

Ser Glu Ile Leu Ala Lys Arg Tyr Gly Gly Phe Met Lys Lys Asp Ala
    130                 135                 140

Glu Glu Asp Asp Ser Leu Ala Asn Ser Ser Asp Leu Leu Lys Glu Leu
145                 150                 155                 160

Leu Glu Thr Gly Asp Asn Arg Glu Arg Ser His His Gln Asp Gly Ser
                165                 170                 175

Asp Asn Glu Glu Glu Val Ser Lys Arg Tyr Gly Gly Phe Met Arg Gly
            180                 185                 190

Leu Lys Arg Ser Pro Gln Leu Glu Asp Glu Ala Lys Glu Leu Gln Lys
        195                 200                 205

Arg Tyr Gly Gly Phe Met Arg Arg Val Gly Arg Pro Glu Trp Trp Met
    210                 215                 220

Asp Tyr Gln Lys Arg Tyr Gly Gly Phe Leu Lys Arg Phe Ala Glu Ala
225                 230                 235                 240

Leu Pro Ser Asp Glu Glu Gly Glu Ser Tyr Ser Lys Glu Val Pro Glu
                245                 250                 255

Met Glu Lys Arg Tyr Gly Gly Phe Met Arg Phe
            260                 265


<210> SEQ ID NO 59
<211> LENGTH: 254
<212> TYPE: PRT
<213> ORGANISM: Homo sapiens

<400> SEQUENCE: 59

Met Ala Trp Gln Gly Leu Val Leu Ala Ala Cys Leu Leu Met Phe Pro
1               5                   10                  15

Ser Thr Thr Ala Asp Cys Leu Ser Arg Cys Ser Leu Cys Ala Val Lys
            20                  25                  30

Thr Gln Asp Gly Pro Lys Pro Ile Asn Pro Leu Ile Cys Ser Leu Gln
        35                  40                  45

Cys Gln Ala Ala Leu Leu Pro Ser Glu Glu Trp Glu Arg Cys Gln Ser
    50                  55                  60

Phe Leu Ser Phe Phe Thr Pro Ser Thr Leu Gly Leu Asn Asp Lys Glu
65                  70                  75                  80

Asp Leu Gly Ser Lys Ser Val Gly Glu Gly Pro Tyr Ser Glu Leu Ala
                85                  90                  95

Lys Leu Ser Gly Ser Phe Leu Lys Glu Leu Glu Lys Ser Lys Phe Leu
            100                 105                 110

Pro Ser Ile Ser Thr Lys Glu Asn Thr Leu Ser Lys Ser Leu Glu Glu
        115                 120                 125

Lys Leu Arg Gly Leu Ser Asp Gly Phe Arg Glu Gly Ala Glu Ser Glu
    130                 135                 140

Leu Met Arg Asp Ala Gln Leu Asn Asp Gly Ala Met Glu Thr Gly Thr
145                 150                 155                 160

Leu Tyr Leu Ala Glu Glu Asp Pro Lys Glu Gln Val Lys Arg Tyr Gly
                165                 170                 175
```

```
Gly Phe Leu Arg Lys Tyr Pro Lys Arg Ser Ser Glu Val Ala Gly Glu
            180                 185                 190

Gly Asp Gly Asp Ser Met Gly His Glu Asp Leu Tyr Lys Arg Tyr Gly
        195                 200                 205

Gly Phe Leu Arg Arg Ile Arg Pro Lys Leu Lys Trp Asp Asn Gln Lys
    210                 215                 220

Arg Tyr Gly Gly Phe Leu Arg Arg Gln Phe Lys Val Val Thr Arg Ser
225                 230                 235                 240

Gln Glu Asp Pro Asn Ala Tyr Ser Gly Glu Leu Phe Asp Ala
                245                 250


<210> SEQ ID NO 60
<211> LENGTH: 15
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(15)
<223> OTHER INFORMATION: D form amino acid

<400> SEQUENCE: 60

Lys Lys Ala Ala Ala Val Leu Leu Pro Val Leu Leu Ala Ala Pro
1               5                   10                  15


<210> SEQ ID NO 61
<211> LENGTH: 15
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(15)
<223> OTHER INFORMATION: D form amino acid

<400> SEQUENCE: 61

Lys Lys Ala Ala Ala Val Leu Leu Pro Val Leu Leu Ala Ala Pro
1               5                   10                  15


<210> SEQ ID NO 62
<211> LENGTH: 19
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(19)
<223> OTHER INFORMATION: D form amino acid

<400> SEQUENCE: 62

Lys Lys Ala Ala Ala Val Leu Leu Pro Val Leu Leu Ala Ala Pro Arg
1               5                   10                  15

Glu Asp Leu


<210> SEQ ID NO 63
<211> LENGTH: 16
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(16)
<223> OTHER INFORMATION: D form amino acid
```

<400> SEQUENCE: 63

Lys Lys Cys Ala Ala Val Leu Leu Pro Val Leu Leu Ala Ala Pro Cys
1 5 10 15

<210> SEQ ID NO 64
<211> LENGTH: 13
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(13)
<223> OTHER INFORMATION: D form amino acid

<400> SEQUENCE: 64

Cys Ala Ala Val Leu Leu Pro Val Leu Leu Ala Ala Cys
1 5 10

<210> SEQ ID NO 65
<211> LENGTH: 14
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(14)
<223> OTHER INFORMATION: D form amino acid

<400> SEQUENCE: 65

Lys Lys Cys Ala Ala Val Leu Leu Pro Val Leu Leu Ala Cys
1 5 10

<210> SEQ ID NO 66
<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form amino acid

<400> SEQUENCE: 66

Cys Ala Ala Val Leu Leu Pro Val Leu Leu Cys
1 5 10

<210> SEQ ID NO 67
<211> LENGTH: 10
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(10)
<223> OTHER INFORMATION: D form amino acid

<400> SEQUENCE: 67

Cys Ala Ala Val Leu Leu Pro Val Leu Cys
1 5 10

<210> SEQ ID NO 68
<211> LENGTH: 13
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(13)
<223> OTHER INFORMATION: D form amino acid

<400> SEQUENCE: 68

Cys Ala Val Leu Leu Pro Val Leu Leu Ala Ala Pro Cys
1 5 10

<210> SEQ ID NO 69
<211> LENGTH: 12
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(12)
<223> OTHER INFORMATION: D form amino acid

<400> SEQUENCE: 69

Cys Val Leu Leu Pro Val Leu Leu Ala Ala Pro Cys
1 5 10

<210> SEQ ID NO 70
<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form amino acid

<400> SEQUENCE: 70

Cys Leu Leu Pro Val Leu Leu Ala Ala Pro Cys
1 5 10

<210> SEQ ID NO 71
<211> LENGTH: 10
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(10)
<223> OTHER INFORMATION: D form amino acid

<400> SEQUENCE: 71

Cys Leu Pro Val Leu Leu Ala Ala Pro Cys
1 5 10

<210> SEQ ID NO 72
<211> LENGTH: 12
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(12)
<223> OTHER INFORMATION: D form amino acid

<400> SEQUENCE: 72

Ala Ala Val Leu Leu Pro Val Leu Leu Ala Ala Pro
1 5 10

<210> SEQ ID NO 73

<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form amino acid

<400> SEQUENCE: 73

Ala Ala Val Leu Leu Pro Val Leu Leu Ala Ala
1 5 10

<210> SEQ ID NO 74
<211> LENGTH: 12
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(12)
<223> OTHER INFORMATION: D form amino acid

<400> SEQUENCE: 74

Lys Lys Ala Ala Val Leu Leu Pro Val Leu Leu Ala
1 5 10

<210> SEQ ID NO 75
<211> LENGTH: 9
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(9)
<223> OTHER INFORMATION: D form amino acid

<400> SEQUENCE: 75

Ala Ala Val Leu Leu Pro Val Leu Leu
1 5

<210> SEQ ID NO 76
<211> LENGTH: 8
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(8)
<223> OTHER INFORMATION: D form amino acid

<400> SEQUENCE: 76

Ala Ala Val Leu Leu Pro Val Leu
1 5

<210> SEQ ID NO 77
<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form amino acid

<400> SEQUENCE: 77

Ala Val Leu Leu Pro Val Leu Leu Ala Ala Pro
1 5 10

<210> SEQ ID NO 78
<211> LENGTH: 10
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(10)
<223> OTHER INFORMATION: D form amino acid

<400> SEQUENCE: 78

Val Leu Leu Pro Val Leu Leu Ala Ala Pro
1 5 10

<210> SEQ ID NO 79
<211> LENGTH: 9
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(9)
<223> OTHER INFORMATION: D form amino acid

<400> SEQUENCE: 79

Leu Leu Pro Val Leu Leu Ala Ala Pro
1 5

<210> SEQ ID NO 80
<211> LENGTH: 8
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(8)
<223> OTHER INFORMATION: D form amino acid

<400> SEQUENCE: 80

Leu Pro Val Leu Leu Ala Ala Pro
1 5

<210> SEQ ID NO 81
<211> LENGTH: 17
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(17)
<223> OTHER INFORMATION: D form amino acid

<400> SEQUENCE: 81

Ala Ala Val Leu Leu Pro Val Leu Leu Ala Ala Lys Lys Lys Arg Lys
1 5 10 15

Ala

<210> SEQ ID NO 82
<211> LENGTH: 17
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(17)
<223> OTHER INFORMATION: D form amino acid

<400> SEQUENCE: 82

Lys Lys Lys Arg Lys Ala Ala Ala Ala Val Leu Leu Pro Val Leu Leu
1 5 10 15

Ala

<210> SEQ ID NO 83
<211> LENGTH: 15
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(15)
<223> OTHER INFORMATION: D form retroinversion peptide

<400> SEQUENCE: 83

Pro Ala Ala Leu Leu Val Pro Leu Leu Val Ala Ala Ala Lys Lys
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(15)
<223> OTHER INFORMATION: D form retroinversion peptide

<400> SEQUENCE: 84

Pro Ala Ala Leu Leu Val Pro Leu Leu Val Ala Ala Ala Lys Lys
1 5 10 15

<210> SEQ ID NO 85
<211> LENGTH: 19
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(19)
<223> OTHER INFORMATION: D form retroinversion peptide

<400> SEQUENCE: 85

Leu Asp Glu Arg Pro Ala Ala Leu Leu Val Pro Leu Leu Val Ala Ala
1 5 10 15

Ala Lys Lys

<210> SEQ ID NO 86
<211> LENGTH: 16
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(16)
<223> OTHER INFORMATION: D form retroinversion peptide

<400> SEQUENCE: 86

Pro Cys Ala Ala Leu Leu Val Pro Leu Leu Val Ala Ala Cys Lys Lys

-continued 1 5 10 15

<210> SEQ ID NO 87
<211> LENGTH: 13
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(13)
<223> OTHER INFORMATION: D form retroinversion peptide

<400> SEQUENCE: 87

Cys Ala Ala Leu Leu Val Pro Leu Leu Val Ala Ala Cys
1 5 10

<210> SEQ ID NO 88
<211> LENGTH: 14
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(14)
<223> OTHER INFORMATION: D form retroinversion peptide

<400> SEQUENCE: 88

Cys Ala Leu Leu Val Pro Leu Leu Val Ala Ala Cys Lys Lys
1 5 10

<210> SEQ ID NO 89
<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form retroinversion peptide

<400> SEQUENCE: 89

Cys Leu Leu Val Pro Leu Leu Val Ala Ala Cys
1 5 10

<210> SEQ ID NO 90
<211> LENGTH: 10
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(10)
<223> OTHER INFORMATION: D form retroinversion peptide

<400> SEQUENCE: 90

Cys Leu Val Pro Leu Leu Val Ala Ala Cys
1 5 10

<210> SEQ ID NO 91
<211> LENGTH: 13
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(13)

<223> OTHER INFORMATION: D form retroinversion peptide

<400> SEQUENCE: 91

Cys Pro Ala Ala Leu Leu Val Pro Leu Leu Val Ala Cys
1 5 10

<210> SEQ ID NO 92
<211> LENGTH: 12
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(12)
<223> OTHER INFORMATION: D form retroinversion peptide

<400> SEQUENCE: 92

Cys Pro Ala Ala Leu Leu Val Pro Leu Leu Val Cys
1 5 10

<210> SEQ ID NO 93
<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form retroinversion peptide

<400> SEQUENCE: 93

Cys Pro Ala Ala Leu Leu Val Pro Leu Leu Cys
1 5 10

<210> SEQ ID NO 94
<211> LENGTH: 10
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(10)
<223> OTHER INFORMATION: D form retroinversion peptide

<400> SEQUENCE: 94

Cys Pro Ala Ala Leu Leu Val Pro Leu Cys
1 5 10

<210> SEQ ID NO 95
<211> LENGTH: 12
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(12)
<223> OTHER INFORMATION: D form retroinversion peptide

<400> SEQUENCE: 95

Pro Ala Ala Leu Leu Val Pro Leu Leu Val Ala Ala
1 5 10

<210> SEQ ID NO 96
<211> LENGTH: 11
<212> TYPE: PRT
<213> ORGANISM: Artificial Sequence -continued
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form retroinversion peptide

<400> SEQUENCE: 96

Ala Ala Leu Leu Val Pro Leu Leu Val Ala Ala
1               5                   10

<210> SEQ ID NO 97
<211> LENGTH: 12
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(12)
<223> OTHER INFORMATION: D form retroinversion peptide

<400> SEQUENCE: 97

Ala Leu Leu Val Pro Leu Leu Val Ala Ala Lys Lys
1               5                   10

<210> SEQ ID NO 98
<211> LENGTH: 9
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(9)
<223> OTHER INFORMATION: D form retroinversion peptide

<400> SEQUENCE: 98

Leu Leu Val Pro Leu Leu Val Ala Ala
1               5

<210> SEQ ID NO 99
<211> LENGTH: 8
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(8)
<223> OTHER INFORMATION: D form retroinversion peptide

<400> SEQUENCE: 99

Leu Val Pro Leu Leu Val Ala Ala
1               5

<210> SEQ ID NO 100
<211> LENGTH: 11
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(11)
<223> OTHER INFORMATION: D form retroinversion peptide

<400> SEQUENCE: 100

Pro Ala Ala Leu Leu Val Pro Leu Leu Val Ala
1               5                   10

<210> SEQ ID NO 101
<211> LENGTH: 10
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(10)
<223> OTHER INFORMATION: D form retroinversion peptide

<400> SEQUENCE: 101

Pro Ala Ala Leu Leu Val Pro Leu Leu Val
1               5                   10

<210> SEQ ID NO 102
<211> LENGTH: 9
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(9)
<223> OTHER INFORMATION: D form retroinversion peptide

<400> SEQUENCE: 102

Pro Ala Ala Leu Leu Val Pro Leu Leu
1               5

<210> SEQ ID NO 103
<211> LENGTH: 8
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(8)
<223> OTHER INFORMATION: D form retroinversion peptide

<400> SEQUENCE: 103

Pro Ala Ala Leu Leu Val Pro Leu
1               5

<210> SEQ ID NO 104
<211> LENGTH: 17
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(17)
<223> OTHER INFORMATION: D form retroinversion peptide

<400> SEQUENCE: 104

Ala Lys Arg Lys Lys Lys Ala Ala Leu Leu Val Pro Leu Leu Val Ala
1               5                   10                  15

Ala

<210> SEQ ID NO 105
<211> LENGTH: 17
<212> TYPE: PRT
<213> ORGANISM: Artificial Sequence
<220> FEATURE:
<223> OTHER INFORMATION: D form peptide
<220> FEATURE:
<221> NAME/KEY: MISC_FEATURE
<222> LOCATION: (1)..(17)

<223> OTHER INFORMATION: D form retroinversion peptide

<400> SEQUENCE: 105

Ala Leu Leu Val Pro Leu Leu Val Ala Ala Ala Ala Lys Arg Lys Lys
1               5                   10                  15

Lys

<210> SEQ ID NO 106
<211> LENGTH: 20
<212> TYPE: PRT
<213> ORGANISM: Artificial Sequence
<220> FEATURE:
<223> OTHER INFORMATION: D-form peptide; Comprises opioid peptide
<220> FEATURE:
<221> NAME/KEY: MISC_FEATURE
<222> LOCATION: (1)..(20)
<223> OTHER INFORMATION: D-form amino acid
<220> FEATURE:
<221> NAME/KEY: MOD_RES
<222> LOCATION: (20)..(20)
<223> OTHER INFORMATION: Amidation

<400> SEQUENCE: 106

Phe Phe Ile Arg Lys Lys Lys Ala Ala Ala Val Leu Leu Pro Val Leu
1               5                   10                  15

Leu Ala Ala Pro
            20

<210> SEQ ID NO 107
<211> LENGTH: 20
<212> TYPE: PRT
<213> ORGANISM: Artificial Sequence
<220> FEATURE:
<223> OTHER INFORMATION: D-form peptide; Comprises opioid peptide
<220> FEATURE:
<221> NAME/KEY: MISC_FEATURE
<222> LOCATION: (1)..(20)
<223> OTHER INFORMATION: D-form amino acid
<220> FEATURE:
<221> NAME/KEY: MOD_RES
<222> LOCATION: (20)..(20)
<223> OTHER INFORMATION: Amidation

<400> SEQUENCE: 107

Lys Lys Ala Ala Ala Val Leu Leu Pro Val Leu Leu Ala Ala Pro Lys
1               5                   10                  15

Phe Phe Ile Arg
            20

<210> SEQ ID NO 108
<211> LENGTH: 19
<212> TYPE: PRT
<213> ORGANISM: Artificial Sequence
<220> FEATURE:
<223> OTHER INFORMATION: D-form peptide; Comprises opioid peptide
<220> FEATURE:
<221> NAME/KEY: MISC_FEATURE
<222> LOCATION: (1)..(19)
<223> OTHER INFORMATION: D-form amino acid
<220> FEATURE:
<221> NAME/KEY: MOD_RES
<222> LOCATION: (19)..(19)
<223> OTHER INFORMATION: Amidation

<400> SEQUENCE: 108

Phe Phe Ile Arg Lys Lys Ala Ala Ala Val Leu Leu Pro Val Leu Leu
1               5                   10                  15

Ala Ala Pro

```
<210> SEQ ID NO 109
<211> LENGTH: 21
<212> TYPE: PRT
<213> ORGANISM: Artificial Sequence
<220> FEATURE:
<223> OTHER INFORMATION: Comprises opioid peptide
<220> FEATURE:
<221> NAME/KEY: MISC_FEATURE
<222> LOCATION: (1)..(1)
<223> OTHER INFORMATION: Linked to biotin-LC
<220> FEATURE:
<221> NAME/KEY: MISC_FEATURE
<222> LOCATION: (18)..(21)
<223> OTHER INFORMATION: D-form amino acid
<220> FEATURE:
<221> NAME/KEY: MOD_RES
<222> LOCATION: (21)..(21)
<223> OTHER INFORMATION: Amidation

<400> SEQUENCE: 109

Lys Lys Lys Ala Ala Ala Val Leu Leu Pro Val Leu Leu Ala Ala Pro
1               5                   10                  15

Lys Phe Phe Ile Arg
            20


<210> SEQ ID NO 110
<211> LENGTH: 20
<212> TYPE: PRT
<213> ORGANISM: Artificial Sequence
<220> FEATURE:
<223> OTHER INFORMATION: Comprises opioid peptide
<220> FEATURE:
<221> NAME/KEY: MISC_FEATURE
<222> LOCATION: (1)..(1)
<223> OTHER INFORMATION: Linked to biotin-LC
<220> FEATURE:
<221> NAME/KEY: MISC_FEATURE
<222> LOCATION: (18)..(20)
<223> OTHER INFORMATION: D-form amino acid
<220> FEATURE:
<221> NAME/KEY: MOD_RES
<222> LOCATION: (20)..(20)
<223> OTHER INFORMATION: Amidation

<400> SEQUENCE: 110

Lys Lys Lys Cys Ala Ala Val Leu Leu Pro Val Leu Leu Ala Cys Lys
1               5                   10                  15

Phe Phe Ile Arg
            20


<210> SEQ ID NO 111
<211> LENGTH: 21
<212> TYPE: PRT
<213> ORGANISM: Artificial Sequence
<220> FEATURE:
<223> OTHER INFORMATION: Comprises opioid peptide
<220> FEATURE:
<221> NAME/KEY: MISC_FEATURE
<222> LOCATION: (1)..(1)
<223> OTHER INFORMATION: Linked to biotin-LC
<220> FEATURE:
<221> NAME/KEY: MISC_FEATURE
<222> LOCATION: (2)..(21)
<223> OTHER INFORMATION: D-form amino acid
<220> FEATURE:
<221> NAME/KEY: MOD_RES
<222> LOCATION: (21)..(21)
<223> OTHER INFORMATION: Amidation

<400> SEQUENCE: 111

Lys Lys Lys Ala Ala Ala Val Leu Leu Pro Val Leu Leu Ala Ala Pro
1               5                   10                  15
```

Lys Phe Phe Ile Arg
20

<210> SEQ ID NO 112
<211> LENGTH: 21
<212> TYPE: PRT
<213> ORGANISM: Artificial Sequence
<220> FEATURE:
<223> OTHER INFORMATION: Comprises opioid peptide
<220> FEATURE:
<221> NAME/KEY: MISC_FEATURE
<222> LOCATION: (1)..(1)
<223> OTHER INFORMATION: Linked to biotin-LC
<220> FEATURE:
<221> NAME/KEY: MISC_FEATURE
<222> LOCATION: (2)..(16)
<223> OTHER INFORMATION: D-form amino acid
<220> FEATURE:
<221> NAME/KEY: MISC_FEATURE
<222> LOCATION: (18)..(21)
<223> OTHER INFORMATION: D-form amino acid
<220> FEATURE:
<221> NAME/KEY: MOD_RES
<222> LOCATION: (21)..(21)
<223> OTHER INFORMATION: Amidation

<400> SEQUENCE: 112

Lys Pro Ala Ala Leu Leu Val Pro Leu Leu Val Ala Ala Ala Lys Lys
1 5 10 15

Lys Phe Phe Ile Arg
20

<210> SEQ ID NO 113
<211> LENGTH: 4
<212> TYPE: PRT
<213> ORGANISM: Artificial Sequence
<220> FEATURE:
<223> OTHER INFORMATION: opioid peptide; D-form peptide
<220> FEATURE:
<221> NAME/KEY: MISC_FEATURE
<222> LOCATION: (1)..(4)
<223> OTHER INFORMATION: D-form amino acid
<220> FEATURE:
<221> NAME/KEY: MOD_RES
<222> LOCATION: (4)..(4)
<223> OTHER INFORMATION: Amidation

<400> SEQUENCE: 113

Phe Phe Ile Arg
1

<210> SEQ ID NO 114
<211> LENGTH: 5
<212> TYPE: PRT
<213> ORGANISM: Artificial Sequence
<220> FEATURE:
<223> OTHER INFORMATION: opioid peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid

<400> SEQUENCE: 114

Tyr Ala Gly Phe Leu
1 5

<210> SEQ ID NO 115

-continued

```
<211> LENGTH: 5
<212> TYPE: PRT
<213> ORGANISM: Artificial Sequence
<220> FEATURE:
<223> OTHER INFORMATION: opioid peptide

<400> SEQUENCE: 115

Tyr Gly Gly Phe Leu
1               5


<210> SEQ ID NO 116
<211> LENGTH: 5
<212> TYPE: PRT
<213> ORGANISM: Artificial Sequence
<220> FEATURE:
<223> OTHER INFORMATION: opioid peptide

<400> SEQUENCE: 116

Tyr Gly Gly Phe Met
1               5


<210> SEQ ID NO 117
<211> LENGTH: 6
<212> TYPE: PRT
<213> ORGANISM: Artificial Sequence
<220> FEATURE:
<223> OTHER INFORMATION: opioid peptide
<220> FEATURE:
<221> NAME/KEY: MISC_FEATURE
<222> LOCATION: (2)..(2)
<223> OTHER INFORMATION: D-amino acid

<400> SEQUENCE: 117

Tyr Thr Gly Phe Leu Thr
1               5


<210> SEQ ID NO 118
<211> LENGTH: 4
<212> TYPE: PRT
<213> ORGANISM: Artificial Sequence
<220> FEATURE:
<223> OTHER INFORMATION: opioid peptide
<220> FEATURE:
<221> NAME/KEY: MISC_FEATURE
<222> LOCATION: (4)..(4)
<223> OTHER INFORMATION: Linked to -NH-NH-Phe-Gly-Gly-Tyr

<400> SEQUENCE: 118

Tyr Gly Gly Phe
1


<210> SEQ ID NO 119
<211> LENGTH: 4
<212> TYPE: PRT
<213> ORGANISM: Artificial Sequence
<220> FEATURE:
<223> OTHER INFORMATION: opioid peptide
<220> FEATURE:
<221> NAME/KEY: MISC_FEATURE
<222> LOCATION: (1)..(1)
<223> OTHER INFORMATION: Linked to Tyr-Gly-Gly-Phe-NH-NH-

<400> SEQUENCE: 119

Phe Gly Gly Tyr
1


<210> SEQ ID NO 120
<211> LENGTH: 16
<212> TYPE: PRT
<213> ORGANISM: Artificial
```

-continued

```
<220> FEATURE:
<223> OTHER INFORMATION: Membrane translocating peptide ZElan094

<400> SEQUENCE: 120

Lys Lys Lys Ala Ala Ala Val Leu Leu Pro Val Leu Leu Ala Ala Pro
1               5                   10                  15


<210> SEQ ID NO 121
<211> LENGTH: 4
<212> TYPE: PRT
<213> ORGANISM: Artificial
<220> FEATURE:
<223> OTHER INFORMATION: N-terminal sequence of ZElan094

<400> SEQUENCE: 121

Lys Lys Lys Ala
1
```

CONJUGATES OF MEMBRANE TRANSLOCATING AGENTS AND PHARMACEUTICALLY ACTIVE AGENTS

CROSS REFERENCE TO RELATED APPLICATIONS

This application is a continuation application of U.S. application Ser. No. 11/303,372, filed Dec. 16, 2005, now U.S. Pat. No. 7,638,599, which is a continuation application of U.S. application Ser. No. 10/955,656, filed Sep. 30, 2004, abandoned, which is a continuation of U.S. application Ser. No. 10/126,845, filed Apr. 19, 2002, abandoned, which is a continuation-in-part of U.S. application Ser. No. 09/671,089, filed Sep. 27, 2000, now U.S. Pat. No. 6,780,846, which claims the benefit of U.S. Provisional Application Ser. No. 60/156,246, filed Sep. 27, 1999, the disclosures of which are incorporated by reference herein in their entireties. U.S. application Ser. No. 10/126,845 claims the benefit of U.S. Provisional Application Ser. No. 60/287,786, filed Apr. 30, 2001, the disclosure of which is incorporated by reference herein in its entirety.

FIELD OF THE INVENTION

The present invention relates to peptides, which enhance uptake of a pharmaceutically active agent into a cell, into or out of an intracellular compartment, and across a cell layer. More particularly, the present invention relates to membrane translocating peptides, thereof and to the nucleotide sequences coding therefor, which enhance uptake of a pharmaceutically active agent into a cell, into or out of an intracellular compartment, and across a cell layer either directly or from a pharmaceutically active agent loaded particle.

INCORPORATION OF ASCII-COMPLIANT SEQUENCE LISTING

The content of the ASCII-compliant text file, "9701-18IPCT3_SUBSTITUTE_ST25.TXT" (71,901 bytes, created May 8, 2010) is incorporated herein in its entirety.

BACKGROUND OF THE INVENTION

The epithelium lining the gastrointestinal tract (hereinafter, "GIT") is a major barrier to absorption of orally administered pharmaceutically active agents (hereinafter, "active agents"). Absorption across the GIT epithelium can be by transcellular transport through the cells and by paracellular transport between the cells. Transcellular transport includes, but is not limited to, receptor-mediated, transporter-mediated, channel-mediated, pinocytotic and endocytotic mechanisms and to diffusion. Paracellular transport includes, but is not limited to, movement through tight junctions. Of particular interest is the development of non-invasive methods for enhancing uptake of active agents across the GIT epithelium into the body (Evers, P. Developments in Drug Delivery: Technology and Markets, Financial Times Management Report, 1995).

To develop non-invasive methods, phage display libraries have been used to identify specific peptide sequences, which bind preferentially to specific GIT membrane receptor, transporter, channel, pinocytotic or endocytotic target pathways (hereinafter, "targeting peptides") within the GIT. Included among the target pathways, which have been screened with phage display libraries, are the GIT membrane transporters HPT1, hPEPT1, D2H and hSI. HPT1 and hPEPT1 transport dipeptides and tripeptides. D2H transports neutral and basic amino acids and is a transport activating protein for a range of amino acid translocases. hSI is involved in sugar metabolism and comprises 9% of the brush border protein in the jejunum. Specific peptide sequences, which interact with the HPT1, hPEPT1, D2H and hSI membrane transporters have been identified in the following 4 applications, each of which is incorporated herein in its entirety: U.S. patent application Ser. Nos. 09/079,819, 09/079,723 and 09/079,678, and PCT application, PCT/US98/10088, published as WO 98/51325.

Non-target pathway based assays have been used to identify peptides with inherent cell membrane translocating properties. These cell membrane translocating peptides interact directly with and penetrate the lipids of cell membranes (Fong et al. Drug Development Research 33:64, 1994). The central hydrophobic h-region of the signal sequence of Kaposi's fibroblast growth factor, AAVLLPVLLAAP (SEQ ID NO: 1) is considered to be a membrane translocating peptide. This peptide (SEQ ID NO: 1) has been used as a carrier to deliver various short peptides (<25 mer), through the lipid bilayer, into living cells in order to study intracellular protein functions and intracellular processes (Lin et al. J. Biol. Chem. 271:5305, 1996; Liu et al. Proc. Natl. Acad. Sci. USA 93:11819, 1996; Rojas et al. J. Biol. Chem. 271:27456, 1996; Rojas et al. Biochem. Biophys. Res. Commun. 234:675, 1997). A 41-kDa glutathione S-transferase fusion protein containing SEQ ID NO: 1 (GST-Grbs-$SH_2$ fused to SEQ ID NO: 1) has been shown to be imported into NIH 3T3 fibroblasts and to inhibit epidermal growth factor induced EGFR-Grb2 association and MAP kinase activation (Rojas et al. Nature Biotechnology 16:370, 1998). However, these studies do not address the use of membrane translocating peptides to enhance active agent uptake into a cell, into and out of an intracellular compartment, or across a cell layer when the active agent is complexed to a membrane translocating peptide or when the active agent is incorporated into a particle and the particle is modified with (hereinafter, "complexed to") a membrane translocating peptide.

The ability to enhance movement of an active agent across a cell membrane is important because, although an active agent can be administered to an animal by a variety of routes including, but not limited to, oral, nasal, mucosal, topical transdermal, intravenous, intramuscular, intraperitoneal, intrathecal and subcutaneous, oral administration is the preferred route. Nasal, mucosal, topical and transdermal administration depend on drug absorption through the mucosa or skin into the circulation. Intravenous administration can result in adverse effects from rapid accumulation of high concentrations of drug, in patient discomfort and in infection at the injection site. Intramuscular administration can cause pain at the injection site. Subcutaneous administration is not suitable for large volumes or for irritating substances. Although oral administration is the preferred route, many active agents are not absorbed efficiently across the GIT epithelium. This results from enzymatic degradation of active agents within the lumen of the GIT, from the limited permeability of the GIT epithelium to active agents, from the large molecular size of active agents and from the hydrophilic properties of active agents (Fix, J A. J. Pharmac. Sci. 85:1282, 1996). To develop an oral formulation, an active agent must be protected from enzymatic digestion within the lumen of the GIT, presented to the absorptive epithelial cells of the GIT in an effective concentration and "moved" across the epithelium in an apical to basolateral direction.

Therefore, because of the advantages of oral drug administration, there is a need for delivery systems, which protect orally ingested active agents from enzymatic degradation within the lumen of the GIT and which promote the absorption of orally ingested active agents into and across the epithelial cells lining the GIT.

BRIEF SUMMARY OF THE INVENTION

The present invention fulfills the above-noted needs by providing membrane translocating peptides (hereinafter referred to interchangeably either as "MTLPs" or "translocating peptides") or nucleotide sequences coding therefore, MTLP-active agent complexes and MTLP-active particle complexes, wherein the MTLP enhances movement of the active agent or the active particle across a lipid membrane. More particularly, the present invention provides a MTLP, MTLP-active agent complexes and MLTP-active particle complexes, wherein the MTLP enhances movement of the active agent or of the active particle into a cell, into and out of an intracellular compartment and across a cell layer in an animal, including a human. Methods of making and methods of using MTLPs, MTLP-active agent complexes and MTLP-active particle complexes also are included.

Compositions and their Peptides

More precisely, in a first general aspect, the invention is a composition comprising a translocating peptide, said translocating peptide selected from the group consisting of a transport peptide, an extended peptide comprising said transport peptide, and a transport-active fragment of at least 4 amino acids of said transport peptide, wherein said transport peptide is selected from the group consisting of an L-peptide, a d-peptide, and a retroinverted peptide, and wherein said L-peptide has an amino acid sequence selected from the group consisting of SEQ ID NOS: 2-13, and 15-24, wherein said d-peptide has an amino acid sequence selected from the group consisting of SEQ ID NOS. 60-82, corresponding to the d-forms of L-peptides of SEQ ID NOS. 2-24, and wherein the retroinverted peptide has an amino acid sequence selected from the group consisting of a peptide of SEQ ID NOS. 83-105, corresponding to retroinverted forms of L-peptides of SEQ ID NOS: 2-24.

A specific embodiment of the composition (first general aspect) is one wherein terminal or near-terminal lysines play a role:

the L-peptide has an amino acid sequence selected from the group consisting of SEQ ID NOS: 2-4, 16, 23 and 24.

the d-peptide has an amino acid sequence selected from the group consisting of SEQ ID NOS. 60-62, 74, 81 and 82, corresponding to the d-forms of L-peptides of SEQ ID NOS. 2-4, 16, 23 and 24, and the retroinverted peptide has an amino acid sequence selected from the group consisting of a peptide of SEQ ID NOS. 83-85, 97, 104 and 105, corresponding to retroinverted forms of an L-peptides of SEQ ID NOS: 2-4, 16, 23 and 24.

In another specific embodiment of the composition, the transport peptide is partially or completely cyclic. In a related embodiment, any fragment of the transport peptide is also partially or completely cyclic. Cyclic peptides of particular interest are those in which the L-peptide has an amino acid sequence selected from the group consisting of SEQ ID NOS: 5-13;

the d-peptide has an amino acid sequence selected from the group consisting of SEQ ID NOS. 63-71, corresponding to the d-forms of L-peptides of SEQ ID NOS. 5-13, and the retroinverted peptide has an amino acid sequence selected from the group consisting of a peptide of SEQ ID NOS. 86-94, corresponding to retroinverted forms of L-peptides of SEQ ID NOS: 5-13.

In another particular embodiment of the composition, the translocating peptide is an extended peptide of a transport peptide. Preferably, the extended peptide is not more than 100 amino acids in length, more preferably not more than 50 amino acids in length.

In a further embodiment of the composition, the translocating peptide is a transport peptide.

It is preferred that the transport-active fragment is at least 6 amino acids, more preferably 8 amino acids of a transport peptide.

In preferred embodiments, the carboxyl end group of the translocating peptide is one that has been modified to create an amide group.

Closely related to the above compositions is one comprising a translocating peptide, said translocating peptide selected from the group consisting of a transport peptide, an extended peptide comprising said transport peptide, and a transport-active fragment of at least 4 amino acids of said transport peptide, said transport peptide being an L-peptide that has an amino acid sequence SEQ ID NO: 14 blocked at its carboxyl end with an amide group and wherein any of said fragments is also blocked at its carboxyl end with an amide group.

The foregoing compositions can, for example, further comprise an active agent, wherein the translocating peptide is complexed to an active agent to form a translocating peptide-active agent complex.

Additionally, the compositions can, for example, further comprise an active particle, wherein the translocating peptide is complexed to the active particle to form a translocating peptide-active particle complex.

Chimeric Peptides

Chimeric polypeptides comprising the translocating peptides are also part of the invention. Specifically such polypeptides comprise (A) a translocating peptide of this invention, (B) a translocatable peptide, and (C) an amino acid linker sequence that directly linked the translocating peptide to the translocatable peptide, wherein said translocatable peptide is between 3 and 200 amino acids, and wherein said amino acid linker sequence is between 1 and 20 amino acids.

In particular embodiments of the chimeric peptides, the translocatable peptide is between 3 and 30 amino acids.

In other embodiments, the translocatable peptide is an opioid peptide (examples of which are listed elsewhere herein).

In some particular embodiments, the linker sequence is not more than 7 amino acids, preferably not more than 3 amino acids. In some useful embodiments, the linker sequence is 1 amino acid.

In some preferred embodiments least 50% of the amino acids in the linker sequence are lysines. More preferably at least 80% of the amino acids in the linker sequence are lysines. Most preferably all of the amino acids in the linker sequence are lysines.

Chimeric Constructs

Closely related to the chimeric peptides of this invention are chimeric constructs. Such constructs comprise (A) a translocating peptide of this invention, (B) a translocatable peptide, and (C) a non-amino acid linker that directly links the translocating peptide to the translocatable peptide, wherein said translocatable peptide is between 3 and 200 amino acids.

Preferred non-amino acid linkers are those that have a molecular weight of less than 1000 (more preferably less than 500).

Preferred non-amino acid linkers are those that provide the chimeric construct at least 50% (more preferably at least 100%) of the stability in SIF as a single lysine linker does for the corresponding chimeric peptide when the translocating peptide is Elan207 and the translocatable peptide is the kappa opioid peptide (at 37° C. for 1 hour, where stability is indicated by retention of the structure of the chimeric structure or peptide.)

Preferred non-amino acid linkers are those that provide the chimeric construct with an IC50 that is not more than twice that of the corresponding chimeric peptide when the translocating peptide is Elan207 and the translocatable peptide is the kappa opioid peptide and the IC50 is measured in the radio-labelled kappa peptide rat brain homogenate assay described herein.

Two or more of the above preferred aspects for a non-amino acid linker is even more preferable.

Examples of Non-Amino Acid Linkers are:

Hydrocarbon chains which can include both unsubstituted and substituted alkyl, aryl, or macrocyclic R groups. Alkyl is intended to mean any straight, branched, saturated, unsaturated or cyclic C1-20 alkyl group. Aryl is intended to mean any aromatic cyclic hydrocarbon based on a six-membered ring. Macrocycle refers to R groups containing at least one ring containing more than seven carbon atoms. Substituted is intended to mean any alkyl, aryl, or macrocyclic groups in which at least one carbon atom is covalently bonded to any functional groups comprising the atoms H, C, N, O, S, F, Cl, Br and I. For details see Application PCT/US00/23440 published as WO 01/01/13957, pages 5-7 of which are incorporated by reference herein in their entirety).

Additional possible linkers are summarized in PCT application/US99/13660 published as WO 99/67284, especially pages 21-23;

Some linkers are well-suited for situations where cleavage of the linker is desired only at specific sites in a person, for example, specific tissue, specific fluid, specific cells, or specific sub-cellular compartments. Examples of where some of the linkers display such cleavage specificity is denoted in parentheses after those linkers, as follows:

Amide (amidase sensitive)

Carbamate (stable in plasma, triggered release)

Disulphide (stable in plasma, reduced in cell compartments, reduced during crossing of BBB)

Ester (pH sensitive, esterase sensitive)

Carbonate (pH sensitive, non-specific enzymatic degradation)

Methods of the Invention

Related to the compositions of the invention are methods that utilize them.

One method of the invention is one that delivers a chimeric peptide to the blood, said method comprising orally administering a chimeric peptide of the invention.

Another method of the invention is a method of delivering a chimeric construct to a site within a person, said method comprising administering a chimeric construct of this invention, said site being selected from the group consisting of a tissue, a fluid, a cell, and a sub-cellular compartment.

Another method of the invention is for enhancing movement of an active agent across a lipid membrane, which comprises using a translocating peptide-active agent complex, wherein the translocating peptide enhances movement of the active agent across the lipid membrane.

Another method of the invention is one for enhancing movement of an active particle across a lipid membrane, which comprises using a translocating peptide-active particle complex, wherein the translocating peptide enhances movement of the active particle across the lipid membrane.

Still another method of the invention is one for identifying a compound having enhanced ability to transport an active agent across a lipid membrane, wherein the compound competes with the translocating peptide for transport across a membrane selected from the group consisting of a cell membrane, an intracellular membrane, the apical and basal membranes of an epithelial cell layer. In a particular embodiment, the epithelial cell layer is a polarized epithelial cell layer.

Another method of the invention is one for treating a pathological disorder in an animal, comprising orally administering to the animal in need of such treatment a complex selected from the group consisting of a translocating peptide-active agent complex and a translocating peptide-active particle complex, wherein an amount of the active agent effective to treat the pathological disorder is moved across the gastrointestinal epithelium of the animal into the circulation.

MTLPs of the present invention are capable of displaying one or more known functional activities associated with a full-length MTLP. Such functional activities include, but are not limited to, the ability to interact with a membrane and the ability to compete for transport of a reporter drug molecule (fMLP) across epithelial cells including, but not limited to, polarized, differentiated human derived Caco-2 cells. Additional functional activities include, but are not limited to, antigenicity, which includes, but is not limited to, the ability to bind to an anti-MTLP antibody and the ability to compete with a MTLP for interaction with a membrane; and, immunogenicity, which includes, but is not limited to, the ability to stimulate antibody generation.

Methods of making a MTLP-active agent complex include, but are not limited to, covalent coupling of a MTLP and an active agent and noncovalent coupling of a MTLP and an active agent. Methods of making a MTLP-active particle complex include, but are not limited to, incorporating an active agent into a particle including, but not limited to, a nanoparticle, a microparticle, a capsule, a liposome, a non-viral vector system and a viral vector system. The MTLP can be complexed to the active particle by methods including, but not limited to, adsorption to the active particle, noncovalent coupling to the active particle and covalent coupling, either directly or via a linker, to the active particle, to the polymer or polymers used to synthesize the active particle, to the monomer or monomers used to synthesize the polymer, and to other components comprising the active particle.

The present invention also includes the nucleotide sequences, which code for the MTLPs. Methods of making nucleotide sequences include, but are not limited to, recombinant means.

MTLPs, MTLP-active agent complexes and MTLP-active particle complexes can be used alone, in combination with or conjugated to other molecules including, but not limited to, molecules that bind to target pathways, to nuclear uptake pathways and to endosomal pathways, molecules that enable mucoadhesion, molecules that facilitate diffusion across lipid membranes or through water filled pores and molecules that regulate or direct intra-cellular trafficking. That is, by using different mechanisms simultaneously, active agent bioavailability may be enhanced.

Related inventions are the use of translocating peptides (i.e., MTLPs) in the following:

a composition comprising a translocating peptide-active particle complex, wherein the particle is a microparticle;

- a composition comprising a translocating peptide-active particle complex, wherein the particle is a nanoparticle;
- a composition comprising a translocating peptide-active particle complex, wherein the particle is a liposome;
- a composition comprising a viral DNA particle, wherein the viral particle is modified to express a translocating peptide on its surface;
- a composition comprising a viral DNA particle, wherein the viral particle is complexed to a translocating peptide following virus production and purification;
- a composition comprising a viral DNA particle, wherein the viral particle is complexed to a translocating peptide following virus production in and purification from a mammalian cell; and
- a composition comprising a non-viral based gene delivery system, wherein the non-viral based gene delivery system is complexed to a translocating peptide.

Further related inventions are the use of translocating peptides in the following methods:

- a method to enhance the movement of an active agent across a lipid membrane;
- a method to enhance the uptake of an active agent into a cell;
- a method to enhance the uptake of an active agent across a cell layer;
- a method to enhance the uptake of an active agent into an epithelial cell;
- a method to enhance the uptake of an active agent across an epithelial cell layer;
- a method to enhance the uptake of an active agent across the epithelial cell layer lining the GIT into the circulation of an animal;
- a method to enhance the movement of an active particle across a lipid membrane;
- a method to enhance the uptake of an active particle into a cell;
- a method to enhance the uptake of an active particle across a cell layer;
- a method to enhance the uptake of an active particle into an epithelial cell;
- a method to enhance the uptake of an active particle across an epithelial cell layer;
- a method to enhance the uptake of an active particle across the epithelial cell layer lining the GIT into the circulation of an animal;
- a method to provide intracellular gene delivery by a non-viral based gene delivery system;
- a method to provide intracellular gene delivery by a non-viral based gene delivery system, wherein the non-viral based gene delivery system is complexed to a translocating peptide;
- a method to provide a rapid screening method to identify translocating peptides, which retain the essential functional activity of the full-length translocating peptide;
- a method to provide cell-based screens for assaying the functional activity of; and
- a method to provide cell-based screens for characterizing the properties of a translocating peptide.

Another aspect of the present invention is a method to provide a method for diagnosing a pathological disorder by oral administration of an amount of a translocating peptide-active agent complex, wherein the active agent is a diagnostic agent, such that the systemic concentration of the diagnostic agent is effective to diagnose the pathological disorder.

Another aspect of the present invention is a method to provide a method for preventing a pathological disorder by oral administration of a translocating peptide-active agent complex, wherein the active agent is a prophylactic agent, such that the systemic concentration of the prophylactic agent is effective to prevent the pathological disorder.

Another aspect of the present invention is a method for treating a pathological disorder by oral administration of a translocating peptide-active agent complex, wherein the active agent is a therapeutic agent, such that the systemic concentration of the therapeutic agent is effective to treat the pathological disorder.

Another aspect of the present invention is a method to provide a method for diagnosing a pathological disorder by oral administration of a translocating-active particle complex, wherein the active particle contains a diagnostic agent, such that the systemic concentration of the diagnostic agent is effective to diagnose the pathological disorder.

Another aspect of the present invention is a method to provide a method for preventing a pathological disorder by oral administration of a translocating peptide-active particle complex, wherein the active particle contains a prophylactic agent, such that the systemic concentration of the prophylactic agent is effective to prevent the pathological disorder.

Another aspect of the present invention is a method to provide a method for treating a pathological disorder by oral administration of a translocating peptide-active particle complex, wherein the active particle contains a therapeutic agent such that the systemic concentration of the therapeutic agent is effective to treat the pathological disorder.

Other objectives, features and advantages of the present invention will become apparent after a review of the following detailed description of the disclosed embodiments and the appended claims.

BRIEF DESCRIPTION OF THE DRAWINGS

FIG. 6 shows the transport of $^3$H-Kappa peptide conjugates across Caco-2 monolayers.

DETAILED DESCRIPTION OF THE INVENTION

Figure 1:
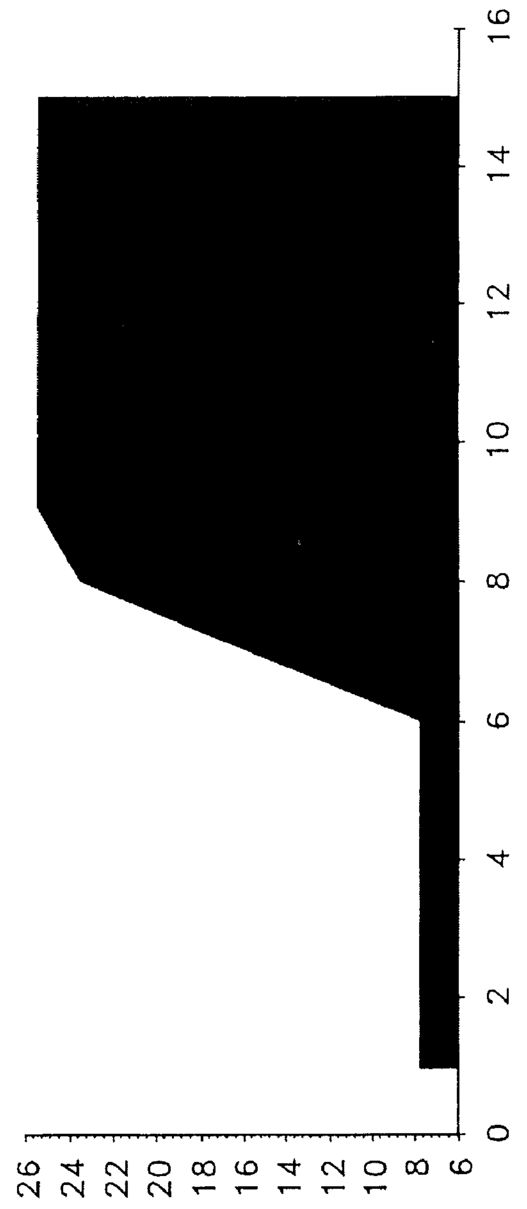
FIG. 1 shows the hydropathy plot for ZElan094 (16 mer) (SEQ ID NO: 2)

The present invention relates to novel membrane translocating peptides (MTLPs or, alternatively, "translocating peptides") to nucleotide sequences coding therefor, to MTLP-active agent complexes and to MTLP-active particle complexes, wherein the MTLP enhances movement of the active agent or of the active particle across a membrane. More particularly, the present invention relates to novel MTLPs, to nucleotide sequences coding therefore, to MTLP-active agent complexes and to MTLP-active particle complexes, wherein the MTLP enhances movement of the active agent in the MTLP-active agent complex, of the active agent in the MTLP-active particle complex and of the active particle in the MTLP active-particle complex into a cell, into and out of an intracellular compartment and across a cell layer in an animal, including a human. Methods of making and methods of using MTLPs also are included.

The present invention also provides methods for diagnosing, preventing or treating a pathological disorder in an animal in need of diagnosis, prevention or treatment of a pathological disorder by administrating to the animal an amount of a MTLP-active agent complex or of a MTLP-active particle complex, such that the systemic concentration of the active agent is effective to diagnose, prevent or treat the pathological disorder.

An “active agent”, as used herein, includes any diagnostic, prophylactic or therapeutic agent that can be used in an animal, including a human.

An “active particle”, as used herein is a particle into which one or more active agents have been loaded.

A membrane translocating peptide, as used herein, is a peptide which interacts directly with and penetrates the lipids of a physiological membrane.

A “MTLP”, as used herein, is a general term that refers to any translocating peptides referred to herein. Specific MTLPs where sequences are described herein can be part of larger peptides or polypeptides, all which, in turn, are MTLPs. Transport-active fragments of MTLPs are also MTLPs.

A “transport-active fragment” of a translocating peptide is one that increases the plasma $^3$H bioavailability of a Kappa peptide by 30%, compared to the Kappa peptide above after intraduodenal installation in the Wistar rat model described herein in Example 15.

The terms “peptide” and “polypeptide” are used to some extent interchangeably herein and no precise size demarcation between the two is intended.

A “composition comprising a translocating peptide” could include not only homogeneous composition consisting only of particular peptide, but also compositions that contain additional components, including end-group moities that are covalently linked to the amino or carboxyl end of such translocating peptides. Specific examples of such in end-group moieties, such as amide, dansyl and biotin groups, are provided herein.

The term “translocating peptide” is used for convenience in phrasing claims that refer to a group of various possible transport peptides. No biochemical difference in function between translocating and transport peptides is intended.

“Complexed to”, as used herein, includes adsorption, non-covalent coupling and covalent coupling of a MTLP to an active agent or to an active particle.

A “MTLP-active agent complex”, as used herein, includes one or more MTLPs complexed to an active agent.

A “MTLP-active particle complex”, as used herein, includes one or more MTLPs complexed to an active particle.

The active agent used depends on the pathological condition to be diagnosed, prevented or treated, the individual to whom it is to be administered, and the route of administration. Active agents include, but are not limited to, imaging agents, antigens, antibodies, oligonucleotides, antisense oligonucleotides, genes, gene correcting hybrid oligonucleotides, aptameric oligonucleotides, triple-helix forming oligonucleotides, ribozymes, signal transduction pathway inhibitors, tyrosine kinase inhibitors, DNA-modifying agents, therapeutic genes, systems for therapeutic gene delivery, drugs and other agents including, but not limited to, those listed in the United States Pharmacopeia and in other known pharmacopeias Drugs include, but are not limited to, peptides, proteins, hormones and analgesics, cardiovascular, narcotic, antagonist, chelating, chemotherapeutic, sedative, anti-hypertensive, anti-anginal, anti-migraine, anti-coagulant, anti-emetic anti-neoplastic and anti-diuretic agents Hormones include, but are not limited to, insulin, calcitonin, calcitonin gene regulating protein, atrial natriuretic protein, colony stimulating factor, erythropoietin (EPO), interferons, somatotropin, somatostatin, somatomedin, luteinizing hormone releasing hormone (LHRH), tissue plasminogen activator (TPA), growth hormone releasing hormone (GHRH), oxytocin, estradiol, growth hormones, leuprolide acetate, factor VIII, testosterone and analogs thereof. Analgesics include, but are not limited to, fentanyl, sufentanil, butorphanol, buprenorphine, levorphanol, morphine, hydromorphone, hydrocodeine, oxymorphone, methadone, lidocaine, bupivacaine, diclofenac, naproxen, paverin, and analogs thereof. Anti-migraine agents include, but are not limited to heparin, hirudin, and analogs thereof. Anti-coagulant agents include, but are not limited to, scopolamine, ondansetron, domperidone, etoclopramide, and analogs thereof. Cardiovascular, anti-hypertensive and vasodilator agents include, but are not limited to, diltiazem, clonidine, nifedipine, verapamil, isosorbide-5-mononitrate, organic nitrates, nitroglycerine and analogs thereof. Sedatives include, but are not limited to, benzodiazeines, phenothiozines and analogs thereof. Narcotic antagonists include, but are not limited to, naltrexone, naloxone and analogs thereof. Chelating agents include, but are not limited to deferoxamine and analogs thereof. Anti-diuretic agents include, but are not limited to, desmopressin, vasopressin and analogs thereof. Anti-neoplastic agents include, but are not limited to, 5-fluorouracil, bleomycin, vincristine, procarbazine, temezolamide, CCNU, 6-thioguanine, hydroxyurea and analogs thereof.

An active agent can be formulated in neutral or salt form. Pharmaceutically acceptable salts include, but are not limited to, those formed with free amino groups; those formed with free carboxyl groups; and, those derived from sodium, potassium, ammonium, calcium, ferric hydroxide, isopropylamine, triethylamine, 2-ethylaminoethanol, histidine and procaine. An active agent can be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

MTLPs have functional activities. Such functional activities include, but are not limited to, enhancing uptake of an active agent into a cell, into and out of an intracellular compartment and across a cell layer and competing with the full-length peptide in enhancing uptake of an active agent into a cell, across a cell layer or into and out of an intracellular compartment.

Examples of MTLPs of the present invention include, but are not limited, to those containing as primary amino acid sequences, all or part of the amino acid sequences substantially as depicted in Table 1

TABLE 1

| MTLPs Amino acid sequences | | |
|---|---|---|
| SEQUENCE + K(ϵ-dansyl) | ELAN NO. | SEQ ID NO. |
| H-K(ϵ-dansyl)KKAAAVLLPVLLAAP-NH2 | ZElan094 | 2 |
| H-KKAAAVLLPVLLAAP-FITC-LC-NH2 | FElan094 | 3 |
| H-K(ϵ-dansyl)KKAAAVLLPVLLAAPREDL-NH2 | ZElan094R | 4 |
| H-K(ϵ-dansyl)KKCAAVLLPVLLAAPC-NH2 | ZElan176 | 5 |
| H-K(ϵ-dansyl)CAAVLLPVLLAAC-NH2 | ZElan177 | 6 |
| H-K(ϵ-dansyl)KKCAAVLLPVLLAC-NH2 | ZElan178 | 7 |
| H-K(ϵ-dansyl)CAAVLLPVLLC-NH2 | ZElan179 | 8 |
| H-K(ϵ-dansyl)CAAVLLPVLC-NH2 | ZElan180 | 9 |
| H-K(ϵ-dansyl)CAVLLPVLLAAPC-NH2 | ZElan181 | 10 |
| H-K(ϵ-dansyl)CVLLPVLLAAPC-NH2 | ZElan182 | 11 |
| H-K(ϵ-dansyl)CLLPVLLAAPC-NH2 | ZElan183 | 12 |
| H-K(ϵ-dansyl)CLPVLLAAPC-NH2 | ZElan184 | 13 |
| H-K(ϵ-dansyl)AAVLLPVLLAAP-NH2 | ZElan185 | 14 |
| H-K(ϵ-dansyl)AAVLLPVLLAA-NH2 | ZElan186 | 15 |
| H-K(ϵ-dansyl)KKAAVLLPVLLA-NH2 | ZElan187 | 16 |
| H-K(ϵ-dansyl)AAVLLPVLL-NH2 | ZElan188 | 17 |
| H-K(ϵ-dansyl)AAVLLPVL-NH2 | ZElan189 | 18 |
| H-K(ϵ-dansyl)AVLLPVLLAAP-NH2 | ZElan190 | 19 |
| H-K(ϵ-dansyl)VLLPVLLAAP-NH2 | ZElan191 | 20 |
| H-K(ϵ-dansyl)LLPVLLAAP-NH2 | ZElan192 | 21 |
| H-K(ϵ-dansyl)LPVLLAAP-NH2 | ZElan193 | 22 |
| H-K(ϵ-dansyl)AAVLLPVLLAAKKKRKA-NH2 | ZElan204N | 23 |
| H-K(ϵ-dansyl)KKKRKAAAAVLLPVLLA-NH2 | ZElanN204 | 24 |

[Underline denotes cyclisation]

An L-peptide that has an amino acid sequence of SEQ ID NO:2 would be KKAAAVLLPVLLAAP. A composition that comprises ZElan094, comprises an L-peptide of SEQ ID NO:2, and further comprises both a K(ϵ-dansyl) group and an amide group.

The 16 residue hydrophobic peptide ZElan094 (SEQ ID NO:120) is related in sequence to the 12 residue hydrophobic peptide sequence AAVLLPVLLAAP (SEQ ID NO:1) (Rojas et al. Nature Biotechnology 16:370, 1998). However, the 16 residue ZElan094 differs from the 12 residue SEQ ID NO:1 in that it has four additional amino acid residues, KKKA (SEQ ID NO:121), at the N-terminus and a blocking amide at the C-terminus. These N-terminus and C-terminus modifications are designed to enhance the solubility and the in vivo stability of the MTLP, respectively. The $NH_2$ terminus alanine also may contribute to the alpha helical properties of the peptide.

The MTLPs of the present invention include peptides comprising all of or a fragment of ZElan094 or having at least 4 of the contiguous amino acids of ZElan094. The MTLPs of the present invention also include sequences that are substantially homologous to regions of ZElan094. Preferably these show at least 70%, 80% or 90% identity over an identical size sequence.

It is understood that a person in the art can make chemical changes in the MTLPs without significantly altering their activity.

Examples of nucleic acid sequences, which encode the peptide sequences of the MTLPs ZElan094, Felan 094, ZElan 094R, 176-193, 204N and N204 (SEQ ID NOS: 2-24) are provided in Table 2 (SEQ ID NOS: 25-47). However, due to the degeneracy of nucleotide coding sequences, different nucleotide sequences, which encode substantially the same amino acid sequence, may be used. That is, a nucleotide sequence, altered by substitution of a different codon, can encode a functionally equivalent amino acid to produce a silent change.

MTLPs may be synthesized using chemical methods (U.S. Pat. Nos. 4,244,946, 4,305,872 and 4,316,891; Merrifield et al. J. Am. Chem. Soc. 85:2149, 1964; Vale et al. Science 213:1394, 1981; Marki et al. J. Am. Chem. Soc. 103:3178, 1981); recombinant DNA methods (Maniatis, Molecular Cloning, a Laboratory Manual, 2d ed. Cold Spring Harbor Laboratory, Cold Spring Harbor N.Y., 1990); viral expression or other methods known to those skilled in the art.

Chemical methods include, but are not limited to, solid phase peptide synthesis. Briefly, solid phase peptide synthesis consists of coupling the carboxyl group of the C-terminal amino acid to a resin and successively adding N-alpha protected amino acids. The protecting groups may be any known in the art. Before an amino acid is added to the growing peptide chain, the protecting group of the previous amino acid is removed (Merrifield J. Am. Chem. Soc. 85:2149 1964; Vale et al. Science 213:1394, 1981; Marki et al. J. Am. Chem. Soc. 103:3178, 1981). The synthesized peptides are then purified by methods known in the art.

TABLE 2

| MTLPs nucleic acid sequences | | |
|---|---|---|
| SEQ ID NO: | ELAN NO: | SEQUENCE |
| 25 | ZElan094 | AARAARAARGCNGCNGCNGTNYTNYTNCCNGTNYT NYTNGCNGCNCCN |
| 26 | FElan094 | AARAARGCNGCNGCNGTNYTNYTNCCNGTNY-TNYTN-GCNGCNCCN |
| 27 | ZElan094R | AARAARAARGCNGCNGCNGTNYTNYTNCCNGTNY-TNYTNGCNGCNCCNMGNGARGAYYTN |
| 28 | ZElan176 | AARAARAARTGYGCNGCNGTNYTNYTNCCNGTNYT NYTNGCCNGNCCNTGY |

TABLE 2-continued

MTLPs nucleic acid sequences

| SEQ ID NO: | ELAN NO: | SEQUENCE |
|---|---|---|
| 29 | ZElan177 | AARTGYGCNGCNGTNYTNYTNCCNGTNYTNYTNGC NGCNTGY |
| 30 | ZElan178 | AARAARAARTGYGCNGCNGTNYTNYTNCCNGTNYT NYTNGCNTGY |
| 31 | ZElan179 | AARTGYGCNGCNGTNYTNYTNCCNGTNYTNYTNTGY |
| 32 | ZElan180 | AARTGYGCNGCNGTNYTNYTNCCNGTNYTNTGY |
| 33 | ZElan181 | AARTGYGCNGTNYTNYTNCCNGTNYTNYTNGCNGC NCCNTGY |
| 34 | ZElan182 | AARTGYGTNYTNYTNCCNGTNYTNYTNGCNGCNCC NTGY |
| 35 | ZElan183 | AARTGYYTNYTNCCNGTNYTNYTNGCNGCNCCNTGY |
| 36 | ZElan184 | AARTGYYTNCCNGTNYTNYTNGCNGCNCCNTGY |
| 37 | ZElan185 | AARGCNGCNGTNYTNYTNCCNGTNYTNYTNGCNGC NCCN |
| 38 | ZElan186 | AARGCNGCNGTNYTNYTNCCNGTNYTNYTNGGNGCN |
| 39 | ZElan187 | AARAARAARGCNGCNGTNYTNYTNCCNGTNYTNYT NGGN |
| 40 | ZElan188 | AARGCNGCNGTNYTNYTNCCNGTNYTNYTN |
| 41 | ZElan189 | AARGCNGCNGTNYTNYTNCCNGTNYTNYTN |
| 42 | ZElan190 | AARGCNGTNYTNYTNCCNGTNYTNYTNGCNGCNCCN |
| 43 | ZElan191 | AARGTNYTNYTNCCNGTNYTNYTNGCNGCNCCN |
| 44 | ZElan192 | AARYTNYTNCCNGTNYTNYTNGCNGCNCCN |
| 45 | ZElan193 | AARYTNGCNGTNYTNYTNGCNGCNCCN |
| 46 | ZElan204N | AARGCNGCNGTNYTNYTNCCNGTNYTNYTNGCNGC NAARAARAARMGNAARGCN |
| 47 | ZElanN204 | AARAARAARAARMGNAARGCNGCNGCNGCNGTNY- TNYTNCCNGTNYTNYTNGCN |

Preferably, solid phase peptide synthesis is done using an automated peptide synthesizer such as, but not limited to, an Applied Biosystems Inc. (ABI) model 431A using the "Fastmoc" synthesis protocol supplied by ABI. This protocol uses 2-(1H-Benzotriazol-1-yl)-1,1,3,3-tetramethyluronium hexafluorophosphate (HBTU) as coupling agent (Knorr et al. Tet. Lett. 30:1927, 1989). Syntheses can be carried out on 0.25 mmol of commercially available 4-(2',4'-dimethoxyphenyl-(9-fluorenyl-ethoxycarbonyl)-aminomethyl) phenoxy polystyrene resin (Rink H. Tet. Lett. 28:3787, 1987). Fmoc amino acids (1 mmol) are coupled according to the Fastmoc protocol. N-methylpyrrolidone (NMP) is used as solvent, with HBTU dissolved in N,N-dimethylformamide (DMF). The following side chain protected Fmoc amino acid derivatives are used: FmocArg(Pmc)OH; FmocAsn(Mbh)OH; FmocAsp(tBu)OH; FmocCys(Acm)OH; FmocGlu(tBu)OH; FmocGln(Mbh)OH; FmocHis(Tr)OH; FmocLys(Boc)OH; FmocSer-(tBu)OH; FmocThr(tBu)OH; FmocTyr(tBu)OH. (Abbreviations: Acm: acetamidomethyl; Boc: tert-butoxycarbonyl; tBu: tert-butyl; Fmoc: 9-fluorenylmethoxy-carbonyl; Mbh: 4,4'-dimethoxybenzhydryl; Pmc: 2,2,5,7,8-pentamethyl-chro-man-6-sulfonyl; Tr: 5 trityl.)

At the end of each synthesis, the amount of peptide is assayed by ultraviolet spectroscopy. A sample of dry peptide resin (about 3-10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol/g) is calculated according to the equation:

$$\text{Substitution} = \frac{A \times v \times 1000}{7800 \times w}$$

where A is the absorbance at 301 nm, v the ml of 20% piperidine in DMA, 7800 the extinction coefficient (mol/$dm^3$/cm) of the dibenzofulvene-piperidine adduct, and w the mg of peptide resin sample. The N-terminal Fmoc group is cleaved using 20% piperidine in DMA, then acetylated using acetic anhydride and pyridine in DMA. The peptide resin is thoroughly washed with DMA, $CH_2C_{l2}$ and diethyl ether.

Methods used for cleavage and deprotection (King et al. Int. J. Peptide Protein Res. 36:255, 1990) include, but are not limited to, treating the air-dried peptide resin with ethylmethyl-sulfide (EtSMe), ethanedithiol (EDT) and thioanisole (PhSMe) for approximately 20 min and adding 95% aqueous trifluoracetic acid (TFA). Approximately 50 ml of these reagents are used per gram of peptide resin in a ratio of TFA:EtSMe:EDT:PhSme (10:0.5:0.5:0.5). The mixture is stirred for 3 h at RT under an $N_2$ atmosphere, filtered and washed with TFA (2×3 ml). The combined filtrate is evaporated in vacuo and anhydrous diethyl ether is added to the yellow/orange residue. The resulting white precipitate is isolated by filtration. Purification of the synthesized peptides is done by standard methods including, but not limited to, ion exchange, affinity, sizing column and high performance liquid chromatography, centrifugation or differential solubility.

Recombinant DNA methods for expressing peptides are well known to those skilled in the art and include expression in a biological system including, but not limited to a mammalian system, an insect system, a plant system and a viral system (Maniatis, T. Molecular Cloning, A Laboratory Manual, 2d ed., Cold Spring Harbor Laboratory, Cold Spring Harbor, N.Y., 1990). For example, a MTLP can be expressed by a virus, by a virus fused to a viral coat protein, a viral capsid protein or a viral surface protein. Further, MTLP-viral protein complexes can be expressed in mammalian hosts or in helper viruses used to produce the virus of interest.

In the production of a gene encoding an extended version of, or a fragment of a full-length peptide, care should be taken to ensure that the modified gene remains within the same translational reading frame uninterrupted by translational stop signals in the gene region where the desired activity is encoded.

Further, phage display vectors including, but not limited to, bacteriophage M13 or bacteriophage Fd can be modified to express a MTLP fused to the gene III protein product or gene VII protein product of the bacteriophage. A library of sequences coding for MTLPs or potential MTLPs can be created including, but not limited to, alanine scan positional mutants, successive random positional scanning mutants and sequences derived therefrom as, for example, those shown in Table 1, can be cloned in-frame to either gene III or gene VII of the bacteriophage. The phage display library can then be screened to identify new MTLPs having enhanced ability to transport active agents or active particles across membranes.

Chimeric or fusion peptides include, without limitation, those comprising a MTLP or multiple repeats thereof, preferably consisting of at least one domain or motif of the full-length peptide sequence or a portion thereof joined at its amino-terminus, at its carboxy-terminus or at an internal site via a peptide bond to an amino acid sequence of a different peptide. Methods for producing chimeric peptides include, but are not limited to, recombinant expression of a nucleic acid including the MTLP coding sequence joined in-frame to the coding sequence of a different peptide. Using methods known in the art, the nucleic acid sequences encoding the desired amino acid sequences are ligated to each other in the proper order and the chimeric product is expressed. For example, chimeric genes comprising portions of MTLP nucleic acid fused to any heterologous protein-encoding nucleic acid may be constructed. Alternatively, chimeric MTLPs may be synthesized using techniques including, but not limited to, a peptide synthesizer.

Opioid peptides include those contained in the corticotropin-lipoprotein precursor, the proenkaphalin A precursor, and the beta-neoendorphin-dynorphin precursor, as follows:

COLI_HUMAN (P01189)
Corticotropin-lipotropin precursor (Pro-opiomelanocortin) (POMC) Contains: NPP; Melanotropin gamma (Gamma-MSH); Corticotropin (Adrenocorticotropic hormone) (ACTH); Melanotropin alpha (Alpha-MSH); Corticotropin-like intermediary peptide (CLIP); Lipotropin beta (Beta-LPH); Lipotropin gamma (Gamma-LPH); Melanotropin beta (Beta-MSH); Beta-endorphin; and Met-enkephalin].
PENK_HUMAN (P01210)
Proenkephalin A precursor contains: Met-enkephalin; and Leu-enkephalin.
NDDB_HUMAN (P01213)
Beta-neoendorphin-dynorphin precursor (Proenkephalin B) (Preprodynorphin) contains: Beta-neoendorphin; Dynorphin; Leu-Enkephalin; Rimorphin; and Leumorphin].

Their amino acid sequences as obtained from the SWISSPROT database are as follows:

```
LOCUS COLI_HUMAN 267 aa linear PRI 01-MAR-2002
DEFINITION Corticotropin-lipotropin precursor (Pro-opiomelanocortin) (POMC)
[Contains: NPP; Melanotropin gamma (Gamma-MSH); Corticotropin
(Adrenocorticotropic hormone) (ACTH); Melanotropin alpha
(Alpha-MSH); Corticotropin-like intermediary peptide (CLIP);
Lipotropin beta (Beta-LPH); Lipotropin gamma (Gamma-LPH);
Melanotropin beta (Beta-MSH); Beta-endorphin; Met-enkephalin].

ACCESSION P01189
PID g116880
VERSION P01189 GI:116880
DBSOURCE swissprot: locus COLI_HUMAN, accession P01189;
SOURCE human.

Region  27 . . . 102 = NPP
Region  77 . . .  87 = "MELANOTROPIN GAMMA."
Region 105 . . . 134 = "?"
Region 138 . . . 150 = "MELANOTROPIN ALPHA."
Region 138 . . . 176 = "CORTICOTROPIN."
Region 156 . . . 176 = "CORTICOTROPIN-LIKE INTERMEDIARY PEPTIDE."
Region 179 . . . 234 = "LIPOTROPIN GAMMA."
Region 179 . . . 267 = "LIPOTROPIN BETA."
Region 217 . . . 234 = "MELANOTROPIN BETA."
Region 237 . . . 241 = "MET-ENKEPHALIN."
Region 237 . . . 267 = "BETA-ENDORPHIN."
```

-continued

ORIGIN (SEQ ID NO: 57)

1 mprsccsrsg alllalllqa smevrgwcle ssqcqdltte snllecirac kpdlsaetpm 61 fpgngdeqpl tenprkyvmg hfrwdrfgrr nssssgssga gqkredvsag edcgplpegg 121 peprsdgakp gpregkrsys mehfrwgkpv gkkrrpvkvy pngaedesae afplefkrel 181 tgqrlregdg pdgpaddgag aqadlehsll vaaekkdegp yrmehfrwgs ppkdkryggf 241 mtseksqtpl vtlfknaiik naykkge LOCUS PENK_HUMAN 267 aa linear PRI 15-JUL-1999
DEFINITION PROENKEPHALIN A PRECURSOR
[CONTAINS: MET-ENKEPHALIN; LEU-ENKEPHALIN].
ACCESSION P01210
PID g129770
VERSION P01210 GI:129770
DBSOURCE swissprot: locus PENK_HUMAN, accession P01210;
SOURCE human.

Region 100 . . . 104 = "MET-ENKEPHALIN 1."
Region 107 . . . 111 = "MET-ENKEPHALIN 2."
Region 136 . . . 140 = "MET-ENKEPHALIN 3."
Region 186 . . . 193 = "MET-ENKEPHALIN-ARG-GLY-LEU."
Region 210 . . . 214 = "MET-ENKEPHALIN 4."
Region 230 . . . 234 = "LEU-ENKEPHALIN."
Region 261 . . . 267 = "MET-ENKEPHALIN-ARG-PHE."

ORIGIN (SEQ ID NO: 58)

1 marfltlctw llllgpglla tvraecsqdc atcsyrlvrp adinflacvm ecegklpslk 61 iwetckellq lskpelpqdg tstlrenskp eeshllakry ggfmkryggf mkkmdelypm 121 epeeeangse ilakryggfm kkdaeeddsl anssdllkel letgdnrers hhqdgsdnee 181 evskryggfm rglkrspqle deakelqkry ggfmrrvgrp ewwmdyqkry qqflkrfaea 241 lpsdeegesy skevpemekr yggfmrf LOCUS PENK_HUMAN 267 aa linear PRI 15-JUL-1999
DEFINITION PROENKEPHALIN A PRECURSOR
[CONTAINS: MET-ENKEPHALIN; LEU-ENKEPHALIN].
ACCESSION P01210
PID g129770
VERSION P01210 GI:129770
DBSOURCE swissprot: locus PENK_HUMAN, accession P01210;
SOURCE human.

Region 100 . . . 104 = "MET-ENKEPHALIN 1."
Region 107 . . . 111 = "MET-ENKEPHALIN 2."
Region 136 . . . 140 = "MET-ENKEPHALIN 3."
Region 186 . . . 193 = "MET-ENKEPHALIN-ARG-GLY-LEU."
Region 210 . . . 214 = "MET-ENKEPHALIN 4."
Region 230 . . . 234 = "LEU-ENKEPHALIN."
Region 261 . . . 267 = "MET-ENKEPHALIN-ARG-PHE."

ORIGIN (SEQ ID NO: 59)

1 marfltlctw llllgpglla tvraecsqdc atcsyrlvrp adinflacvm ecegklpslk 61 iwetckellq lskpelpqdg tstlrenskp eeshllakry ggfmkryggf mkkmdelypm 121 epeeeangse ilakryggfm kkdaeeddsl anssdllkel letgdnrers hhqdgsdnee 181 evskryggfm rglkrspqle deakelqkry ggfmrrvgrp ewwmdyqkry ggflkrfaea 241 lpsdeegesy skevpemekr yggfmrf The SwissProt database records for accession numbers P01189, P01210, and P01213 as they appeared on Apr. 17, 2002 are incorporated herein by reference in their entireties.

Additional opioid peptides include, but are not limited to:

```
boc-Tyr-Tic

cy-[Tyr-Tic]

Tyr-D-Tic

Tyr-D-Tic-NH2

Tyr-cy-[D-Cys-Phe-D-Pen]

Tyr-D-Tic-Phe-Phe-NH2

Tyr-Tic-Phe-Phe

Tyr-cy-[D-Pen-Ala-Phe-D-Pen]

Tyr-cy-[D-Pen-D-Ala-Phe-D-Pen]

Tyr-cy-[D-Pen-Gly-Phe-D-Pen]

Tyr-cy-[D-Pen-Ser-Phe-Pen]

Tyr-D-Pen-Gly-Phe-DMPT

Tyr-D-Ala-Gly-Phe-D-Leu
(SEQ ID NO: 114)

Tyr-D-Nle-Gly-Phe-NleS

Tyr-Gly-Gly-Phe-Leu
(SEQ ID NO: 115)

Tyr-Gly-Gly-Phe-Met
(SEQ ID NO: 116)

Tyr-D-The-Gly-Phe-Leu-Thr
(SEQ ID NO: 117)

N,N-diallyl-(O-t-butyl)-Tyr-Aib-Aib-Phe-Leu-O-Me

Tyr-cy-[D-Pen-Gly-Phe-D-Pen]-Nle-Gly-NH2

Tyr-Gly-Gly-Phe-NH-NH-Phe-Gly-Gly-Tyr
(SEQ ID NOS: 118 and 119 for Tyr-Gly-Gly-Phe and
Phe-Gly-Gly-Tyr, respectively)

[Leu]-enkephalin
Where the following abbreviations are used:
Pen-penicilamine

Nle-nor-leucine (CH3-CH2-CH2-OH2-CH-(NH2)COOH)

NleS-CH3-CH2-CH2-OH2-CH-(NH2)SO3H

Tic-tetrahydroisoquinoline-3-carboxylic acid

Aib-alpha-aminoisobutryric acid

cy-cyclo
```

MTLPs may be linked to other molecules including, but not limited to, detectable labels, adsorption facilitating molecules, toxins or solid substrata by methods including, but not limited to, the use of homobifunctional and heterobifunctional cross-linking molecules (Carlsson et al. Biochem. J. 173:723, 1978; Cumber et al. Methods in Enzymology 112: 207, 1978; Jue et al. Biochem. 17:5399, 1978; Sun et al. Biochem. 13:2334, 1974; Blather et al. Biochem. 24:1517, 1985; Liu et al. Biochem. 18:690, 1979; Youle and Neville Proc. Natl. Acad. Sci. USA 77:5483, 1980; Lerner et al. Proc. Natl. Acad. Sci. USA 78:3403. 1981; Jung and Moroi Biochem. Biophys. Acta 761:162 1983; Caulfield et al. Biochem. 81:7772, 1984; Staros Biochem. 21:3950, 1982; Yoshitake et al. Eur. J. Biochem. 101:395, 1979; Yoshitake et al. J. Biochem. 92:1413, 1982; Pilch and Czech J. Biol. Chem. 254: 3375, 1979; Novick et al. J. Biol. Chem. 262:8483. 1987; Lomant and Fairbanks J. Mol. Biol. 104:243, 1976; Hamada and Tsuruo Anal. Biochem. 160:483, 1987; Hashida et at J. Applied Biochem. 6:56, 1984; Means and Feeney Bioconjugate Chem. 1:2, 1990).

MTLPs may be used as immunogens to generate antibodies which immunospecifically bind the immunogen. Such antibodies include, but are not limited to polyclonal, monoclonal, chimeric, single chain Fab fragments, $F(ab')_2$ fragments and Fab expression libraries. Uses of such antibodies include, but are not limited to, localization, imaging, diagnosis, treatment and treatment efficacy monitoring. For example, antibodies or antibody fragments specific to a domain of a MTLP, such as a dansyl group or some other epitope introduced into the peptide, can be used to identify the presence of the MTLP, to bind the MTLP to the surface of a particle, to quantitate the amount of the MTLP on a particle, to measure the amount of the MTLP in a physiological sample, to immunocytochemically localize the MTLP in a cell or tissue sample, to image the MTLP after in vivo administration and to purify the MTLP by immunoaffinity column chromatography.

The functional activity of a MTLP can be determined by suitable in vivo or in vitro assays known to those skilled in the art. These include, but are not limited to, immuno-, immunoradiometric-, immunodiffusion- and immunofluorescence assays and to western blot analysis.

A MTLP functions to target an active agent or an active particle to a cell, intracellular compartment, or cell layer and to enhance the uptake of the active agent or of the active particle into a cell, into and out of an intracellular compartment and across a cell layer. Cells include, but are not limited to, epithelial, endothelial and mesothelial cells, unicellular organisms and plant cells. Cell layers include epithelial, endothelial and mesothelial cell layers such as, but not limited to, the gastrointestinal tract, pulmonary epithelium, blood brain barrier and vascular endothelium. Preferably the cell is an epithelial cell and the cell layer is an epithelial cell layer. Most preferably, the cell is a GIT epithelial cell and the cell layer is the GIT epithelial cell layer. Intracellular compartments include, but not limited to, nuclear, mitochondrial, endoplasmic reticular and endosomal compartments. MTLPs can be used to enhance the uptake of an active agent or active particle that regulates or directs intra-cellular trafficking. Further, MTLPs can be used to enhance intracellular gene delivery. That is, a gene or plasmid DNA is encapsulated or complexed within a cationic lipid polymer system and the surface of the cationic lipid polymer system is complexed with an MTLP or with a targeting peptide. Alternatively, a plasmid DNA is condensed, the condensate is complexed with cationic lipids and the surface of the cationic lipids is complexed with an MTLP or with a targeting peptide.

Methods used to complex a MTLP to an active agent (MTLP-active agent complex) include, but are not limited to, covalent coupling of a MTLP and an active agent, either directly or via a linking moiety, noncovalent coupling of a MTLP and an active agent and generation of a fusion protein, wherein a MTLP is fused in-frame to an active agent including, but not limited to a therapeutic protein.

Methods used to complex a MTLP to an active agent loaded particle (MTLP-active particle complex) include, but are not limited to, adsorption to the active particle, noncovalent coupling to the active particle; covalent coupling, either directly or via a linker, to the active particle, to the polymer or polymers used to synthesize the active particle, to the monomer or monomers used to synthesize the polymer; and, to any other component comprising the active particle. Further, MTLPs can be complexed to a slow-release (controlled release) particle or device (Medical Applications of Controlled Release, Langer & Wise (eds.), CRC Press, Boca Raton, Fla., 1974; Controlled Drug Bioavailability, Drug Product Design and Performance, Smolen and Ball (eds.), Wiley, New York, 1984; Ranger et al. J. Macromol. Sci. Rev. Macromol. Chem. 23:61, 1983; Levy et al. Science 228:190, 1985; During et al. Ann. Neurol. 25:351, 1989; Howard et al. J. Neurosurg. 71:105 1989).

Methods used for viral based gene delivery systems include, but are not limited to, vectors modified at the nucleic acid level to express a MTLP on the surface of a viral particle and mammalian cells or helper viruses, which express MTLP-virus fusion proteins that are incorporated into a viral vector.

The present invention also provides pharmaceutical formulations, comprising a therapeutically effective amount of a MTLP-active agent complex or of a MTLP-active particle complex and a pharmaceutically acceptable carrier (Remington's Pharmaceutical Sciences by E. W. Martin). The term "pharmaceutically acceptable" includes, but is not limited to, carriers approved by a regulatory agency of a country or a state government or listed in the U.S. Pharmacopeia or other generally recognized pharmacopeia for use in animals, and more particularly in humans. The term "carrier" refers to a diluent, adjuvant, excipient, or vehicle with which the MTLP-active agent complex or the MTLP-active particle complex is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical formulation is administered orally. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The formulation, if desired, can also contain minor amounts of wetting or emulsifying agents, or pH buffering agents. These compositions include, but are not limited to, solutions, suspensions, emulsion, tablets, pills, capsules, powders and sustained-release formulations. The formulation can be a suppository, with traditional binders and carriers such as triglycerides. Oral formulation can include standard carriers including, but not limited to, pharmaceutical grades of mannitol, lactose, starch, magnesium stearate, sodium saccharine, cellulose and magnesium carbonate. Such formulations will contain a therapeutically effective amount of the active agent or of the active agent loaded into a particle, together with a suitable amount of carrier so as to provide the form for proper administration to an individual in need of the active agent.

Any route known in the art may be used to administer a MTLP-active agent complex or a MTLP-active particle complex, including but not limited, to oral, nasal, topical, mucosal, intravenous, intraperitoneal, intradermal, intrathecal, intramuscular, transdermal and osmotic. Preferably, administration is oral, wherein the MTLP enhances uptake of the active agent into a GIT epithelial cell and across the GIT epithelium into the circulation. The precise amount of active agent to be administered for the diagnosis, prevention or treatment of a particular pathological condition will depend on the pathological disorder, the severity of the pathological disorder, the active agent used and the route of administration. The amount of active agent to be administered and the schedule of administration can be determined by the practitioner using standard clinical techniques. In addition, in vitro assays may optionally be employed to help identify optimal ranges for active agent administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Peptide Synthesis

The membrane translocating peptides ZElan094, 204N and 204 and the targeting peptides HAX42, PAX2, P31 and Sni34 (U.S. patent application Ser. Nos. 09/079,819, 09/079,723 and 09/079,678) were synthesized chemically using a fmoc synthesis protocol (Anaspec, Inc., San Jose, Calif.). A dansyl group was added at the N-terminus of each sequence in order to enable the detection of the peptide with anti-dansyl antibody (Table 1).

The physical characteristics of Zelan094 (SEQ ID NO:2) are shown in Table 3.

TABLE 3

Physical characteristics of ZElan 094 (SEQ ID NO: 2)

| | |
|---|---|
| Mass (M + H+): | 1838.03 |
| Solubility | 1 mg/ml water |
| Appearance | white powder |
| HPLC purity | >95% |
| Kyle-Doolittle Hydropathy Plot | FIG. 1 |

Example 2

Preparation of MTLP-Active Particle Complexes and of Targeting Peptide-Active Particle Complexes Active particles were prepared from a polymer using a coacervation method. Preferably, particle size is between about 5 nm and 750 μm, more preferably between about 10 nm and 500 μm and most preferably between about 50 nm and 800 nm. MTLPs or targeting peptides were complexed to the particles using various methods known to those skilled in the art.

The following is a general method for preparation of coacervated particles.

Phase A A polymer agent, a surface-active agent, a surface-stabilizing agent, a surface-modifying agent or a surfactant is dissolved in water (A). Preferably the agent is a polyvinyl alcohol (hereinafter "PVA") or a derivative thereof having a % hydrolysis of about 50-100 and a molecular weight range of about 500-500,000 kDa. More preferably the agent is a PVA having a % hydrolysis of 80-100 and a molecular weight range of about 10,000-150,000 kDa. The mixture (A) is stirred under low shear conditions at 10-2000 rpm and, more preferably, at 100-600 rpm. The pH and ionic strength of the solution may be modified using salts, buffers or other modifying agents. The viscosity of the solution may be modified using polymers, salts, or other viscosity modifying agents.

Phase A may include agents such as, but not limited to, emulsifying agents, detergents, solubilizing agents, wetting agents, foaming agents, antifoaming agents, flocculents and defloculents. Examples include, but are not limited to, anionic surface agents such as sodium dodecanoate, sodium dodecyl-(lauryl)sulphate, sodium dioctyl-sulphosuccinate, ceto-stearyl alcohol, stearic acid and its salts such as magnesium stearate and sodium stearate, sodium dodecyl-benzene sulphonate, sodium cholate triethanolamine; cationic surface agents such as hexadecyl trimethyl ammonium bromide (cetrimide), dodecyl pyridinium iodide, dodecyl pyridinium chloride; non-ionic surface agents such as hexaoxyethylene monohexadecyl ether, polysorbates (Tweens), sorbitan esters (Spans), Macrogol ethers, Poloxalkols (Poloxamers), PVA, PVP, glycols and glycerol esters, fatty alcohol poly glycol ethers, dextrans, higher fatty alcohols; and, amphoteric surface agents such as N-dodecyl alanine, lecithin, proteins, peptides, polysaccharides, semisynthetic polysaccharides, sterol-containing substances, and finely divided solids such as magnesium hydroxide and montmorillonite clays.

Phase B A polymer is dissolved in a water miscible organic solvent to form the organic phase (B). Preferably the organic phase is an acetone-ethanol mixture in ratios from 0:100 acetone:ethanol to 100:0 acetone:ethanol depending upon the polymer used. Other polymers, peptides, sugars, salts, natural-polymers, synthetic polymers or other agents may be added to the organic phase (B) to modify the physical and chemical properties of the resultant particle product.

The polymers may be soluble, permeable, impermeable, biodegradable or gastroretentive. They may be a mixture of natural or synthetic polymers and copolymers. Such polymers include, but are not limited to, polylactides, polyglycolides, DL, L and D forms of poly(lactide-coglycolides) (PLGA), copolyoxalates, polycaprolactone, polyesteramides, polyorthoesters, polyanhydrides, polyalkylcyanoacrylates, polyhydroxy-butyrates, polyurethanes, albumin, casein, citosan derivatives, gelatin, acacia, celluloses, polysaccharides, alginic acid, polypeptides and the like, copolymers thereof, mixtures thereof, enantiomeric forms thereof, stereoisomers thereof and any MTLP conjugate thereof. Synthetic polymers include, but are not limited to, alkyl celluloses, hydroxyalkyl celluloses, cellulose ethers; cellulose esters, nitrocelluloses, acrylic and methacrylic acids and esters thereof, dextrans, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidones, polysiloxanes, polyurethanes and copolymers thereof.

Phase C Phase B is stirred into phase A at a continuous rate. Solvent is evaporated, preferably by increasing the temperature over ambient and/or by using a vacuum pump. The resultant particles are in the form of a suspension (C)

An active agent may be added into phase A or into phase B. Active agent loading may be in the range 0-90% w/w. An MTLP or a targeting peptide may be added into phase C. MTLP and targeting peptide loading may be in the range 0-90% w/w.

Phase D The particles (D) are separated from the suspension (C) using standard colloidal separation techniques including, but not limited to, centrifugation at high 'g' force, filtration, gel permeation chromatography, affinity chromatography or charge separation. The liquid phase is discarded and the particles (D) are re-suspended in a washing solution such as, but not limited to, water, salt solution, buffer or organic solvent. The particles are separated from the washing liquid using standard colloidal separation techniques and are washed two or more times. A MTLP or targeting peptide may be used to wash the particles or, alternatively, may be dissolved in the final wash. The particles are dried.

A secondary layer of polymers, peptides sugars, salts, natural and/or biological polymers or other agents may be deposited onto the preformed particulate core by any suitable method known in the art. The dried particles can be further processed by, for example, tableting, encapsulating or spray drying. The release profile of the particles formed may be varied from immediate to controlled or delayed release depending on the formulation used and/or desired.

Example 3

Bovine Insulin Loaded-MTLP Coated Nanoparticles—MTLP Added in the Final Wash Fast acting bovine insulin (28.1 IU/mg) was incorporated into polylactide-co-glycolide (PLGA, Boehringer Ingelheim, Indianapolis, Ind.) at a theoretical loading of 300 IU of insulin/210 mg of nanoparticles and the nanoparticles were coated with the dansylated ZElan094 (SEQ ID NO: 2).

| COMPONENT | AMOUNT |
|---|---|
| PLGA RG504H (Lot # 250583) | 2 g |
| Acetone | 45 mls |
| Ethanol | 5 mls |
| PVA (5% w/v) (13-23 kDa, 98% hydrolysis) | 400 mls |
| Bovine Insulin (Lot # 86HO674) | 100 mg |
| ZElan094 (SEQ. ID NO: 2) | 10 mg/50 ml dH20 |

Preparation:

1. Water was heated to near boiling, PVA was added to 5% w/v and the solution was stirred until cool (phase A).

2. Acetone and ethanol were mixed to form the organic phase (phase B).

3. PLGA was added to the acetone and ethanol (step 2) and dissolved by stirring (phase B).

4. An IKA™ reactor vessel was set at 25° C. Phase A (step 1) was added into the reactor vessel and stirred at 400 rpm.

5. Bovine insulin was added into the stirring phase A (step 4).

6. Using clean tubing and a green needle, phase B (step 3) was slowly dripped into the stirring solution (step 5) using a peristaltic pump set at 40.

7. The solvent was evaporated by opening the IKA™ reactor vessel ports and stirring overnight at 400 rpm to form a suspension (phase C).

8. The suspension, phase C (step 7) was centrifuged in a XL90 centrifuge at 12,500 to 15,000 rpm for 25 to 40 minutes at 4° C.

9. The supernatant was discarded, the particle "cake" broken up, and the particles (phase D) washed twice in 200 ml of $dH_20$ by centrifugation in an XL90 centrifuge at 12,500 to 15,000 rpm for 10-15 minutes at 4° C. The dansylated ZElan094 (SEQ ID NO: 2) was added into the final wash.

10. The supernatant was decanted, the 'cake' broken up and the particles dried in a vacuum oven. The dried particles were ground, placed in a securitainer and analyzed. Insulin loading was 5% or 50 mg insulin/g particles. Insulin potency, determined in HPLC, was 51.4 mg/g. Scanning electron microscopy showed discrete, reasonably spherical particles of about 300-400 nm in diameter.

Example 4

Bovine Insulin Loaded-MTLP Coated Nanoparticles—MTLP Added to Phase C

Fast acting bovine insulin (28.1 μl/mg) was incorporated into PLGA nanoparticles at a theoretical loading of 300 IU of insulin/210 mg of nanoparticles and the nanoparticles were coated with the MTLP ZElan094 (SEQ ID NO: 2).

| COMPONENT | AMOUNT |
|---|---|
| PLGA RG504H (Lot # 250583) | 2 g |
| Acetone | 45 mls |
| Ethanol | 5 mls |
| PVA (5% w/v) (13-15 kDa, 98% hydrolysis) | 400 mls |
| Bovine Insulin (Lot #. 86HO674) | 100 mg |
| ZElan094 (SEQ. ID NO: 2) | 10 mg/50 ml dH20 |

Preparation:
See steps 1-4 of Example 3.
Step 5. Insulin and ZElan094 were added to the stirring PVA solution.
See steps 6-9 of Example 3.
The particles (step 9) were ground, placed in a securitainer and analyzed.

Example 5

Bovine Insulin Loaded-MTLP Coated Nanoparticles—MTLP Added 1 Hour Prior to Centrifugation Fast acting bovine insulin (28.1 IU/mg) was incorporated into PLGA nanoparticles at a theoretical loading of 300 IU of insulin/210 mg of nanoparticles and the nanoparticles were coated with dansylated ZElan094 (SEQ ID NO: 2).

| COMPONENT | AMOUNT |
|---|---|
| PLGA RG504H (Lot # 250583) | 2 g |
| Acetone | 45 mls |
| Ethanol | 5 mls |
| PVA (5% w/v) (13-15 kDa, 98% hydrolysis) | 400 mls |
| Bovine Insulin (Lot #. 86HO674) | 100 mg |
| ZElan094 (SEQ. ID NO: 2) | 10 mg/50 ml dH20 |

Preparation.
See steps 1-7 of Example 3.
Step 8. ZElan094 was added to the stirring particle suspension. After 1 hr, the suspension was centrifuged at 12,500-14,000 rpm for 20 to 40 min at 4° C.
See steps 9-10 of Example 3.

Example 6

Bovine Insulin Loaded-MTLP Nanoparticles—MTLP Conjugated Polymer

Fast acting bovine insulin is incorporated into PLGA-dansylated ZElan094 (SEQ ID NO: 2) conjugate nanoparticles at a theoretical loading of 300 IU of insulin/210 mg of nanoparticles as follows.

Component
PLGA RG504H (Lot # 250583)
RG504H-ZElan094 (SEQ ID NO: 2) conjugate
Acetone
Ethanol
PVA (5% w/v) (13-15 kDa, 98% hydrolysis)
Bovine Insulin Preparation is as in steps 1-10 of Example 3, except that in step 3 RG504H and RG504H-ZElan094 conjugate are added to phase B (step 2).

Example 7

Bovine Insulin Loaded-Target Peptide Coated Nanoparticles

Fast acting bovine insulin (28.1 IU/mg) was incorporated into PLGA nanoparticles at a theoretical loading of 300 IU of insulin/210 mg of nanoparticles and the nanoparticles were coated with the targeting peptides dansylated ZElan 011, 055, 091, 101, 104, 128, 129 and 144 (U.S. patent application Ser. Nos. 09/079,819, 09/079,723 AND 09/079,678).

| COMPONENT | AMOUNT |
|---|---|
| PLGA RG504H (Lot # 250583) | 2 g |
| Acetone | 45 ml |
| Ethanol | 5 ml |
| PVA (5% w/v) (13-15 kDa, 98% hydrolysis) | 400 ml |
| Bovine Insulin (Lot #. 86HO674) | 100 mg |
| ZElan011, 055, 091, 101, 104, 128, 129 and 144 | 10 mg/50 ml dH20 |

(U.S. patent application Ser. Nos. 09/079,819, 09/079,723 AND 09/079,678, AND PCT APPLICATION PCT/US98/10088, PUBLISHED AS WO 98/51325))

Preparation:
See steps 1-10 of Example 3.
Insulin loading was 5% or 50 mg insulin/g particles.

Example 8

Animal Studies

In vivo oral insulin bioavailability from MTLP-insulin particle complexes (Example 3) and from targeting peptide-insulin particle complexes (Example 7) were assessed in the open loop rat model.

Fifty-nine Wistar rats (300-350 g) were fasted for 4 hours and were anaesthetized by intramuscular injection of 0.525 ml of ketamine (100 mg/ml)+0.875 ml of acepromazine maleate-BP (2 mg/ml) 15 to 20 minutes prior to administration of MTLP-insulin particle complexes or of targeting peptide-insulin particle complexes. The rats were divided into 9 groups, each group containing 6 or 7 animals. Approximately 200 mg of MTLP-insulin (300 IU) particle complexes, suspended in 1.5 ml of PBS, were injected intra-duodenally at 2-3 cm below the pyloris of each of 6 rats (Group 5). Approximately 200 mg of targeting peptide-insulin (300 IU) particle complexes, suspended in 1.5 ml of PBS, were injected intra-duodenally at 2-3 cm below the pyloris of each of 6-7 rats (Groups 1-4 and 6-9). The study groups are shown in Table 4.

TABLE 4

Study Groups

| GROUP # | # OF RATS | PEPTIDE | ZELAN NO | SEQ ID NO[a]: |
|---|---|---|---|---|
| 1 | 6 | HAX42 | 091 | 50 |
| 2 | 7 | PAX2 | 144 | 53 |
| 3 | 7 | PAX2 | 129 | 54 |
| 4 | 6 | P31 | 101 | 52 |

TABLE 4-continued

| Study Groups | | | | |
|---|---|---|---|---|
| GROUP # | # OF RATS | PEPTIDE | ZELAN NO | SEQ ID NO[a]: |
| 5 | 6 | MTLP | 094 | 48 |
| 6 | 7 | PAX2 | 128 | 55 |
| 7 | 7 | PAX2 | 104 | 56 |
| 8 | 7 | HAX42 | 011 | 49 |
| 9 | 7 | PAX2 | 055 | 51 |

[a](U.S. patent application Ser. Nos. 09/079,819, 09/079,723 AND 09/079,678, AND PCT APPLICATION PCT/US98/10088 PUBLISHED AS WO 98/51325)

Systemic blood was sampled from the tail vein (0.4 ml) of each rat at 0 minutes and at 15, 30, 45, 60 and 120 minutes after intra-duodenal administration of the ZElan094-insulin particle complexes or of the targeting peptide-insulin particle complexes. Blood glucose in each sample was measured using a Glucometer (Bayer; 0.1 to 33.3 μm/mol/L). The blood was centrifuged and the plasma was retained. Plasma insulin was assayed in duplicate using a Phadeseph RIA Kit (Pharmacia, Piscataway, N.J.; 3 to 240 μU/ml).

Figure 2:
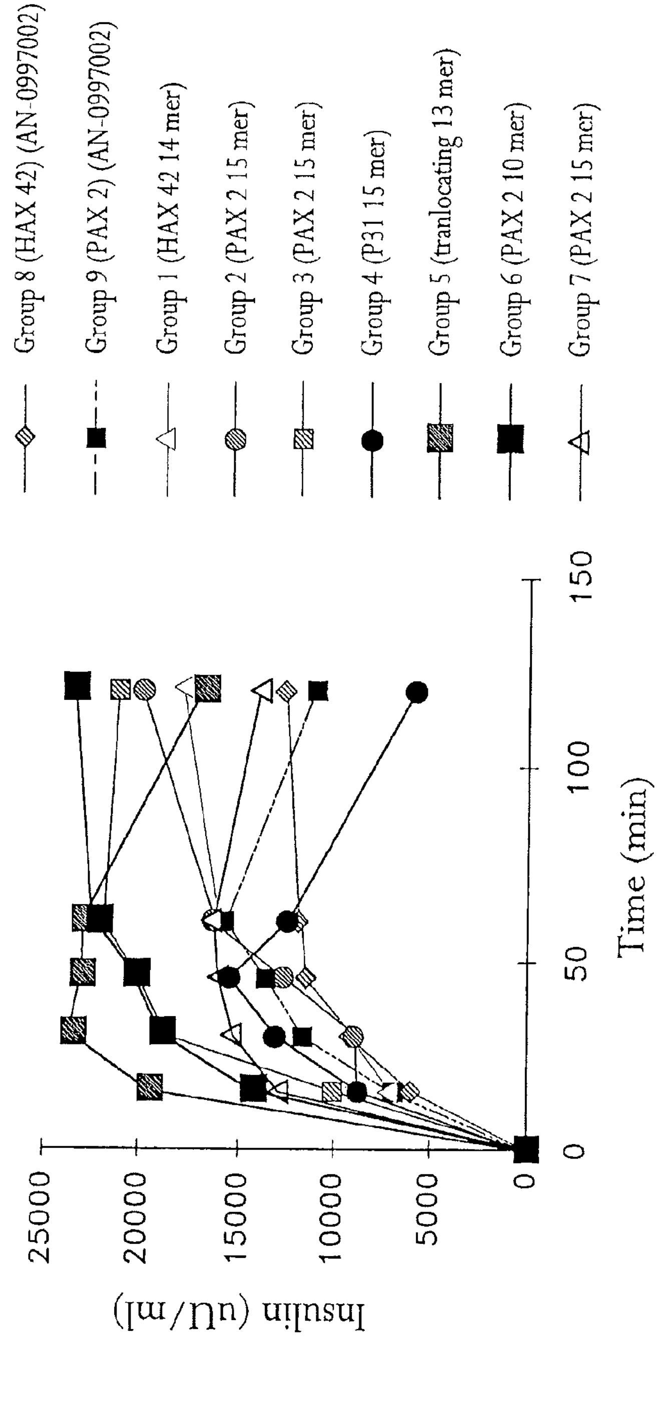
FIG. 2 shows the systemic blood insulin levels following in vivo delivery of insulin from a ZElan094-insulin nanoparticle complex and from HAX42-, PAX2- and P31-insulin nanoparticle complexes in the open loop rat model. Each point is the mean of 6-7 animals.

FIG. 2 shows the plasma insulin levels following intra-duodenal administration of ZElan094-insulin particle complexes (Group 5) and of targeting peptide ZElan091—(Group 1), 144—(Group 2), 129—(Group 3), 101—(Group 4), 128—(Group 6), 104—(Group 7) and 011—(Group 8) insulin particle complexes. As shown in FIG. 2, during the 60 minutes following intra-duodenal administration, ZElan094-insulin particle complexes provided the most potent enhancement of insulin delivery followed by ZElan055-, 129- and 094-, 101-, 128-, 091- and 144, and 011-insulin particle complexes. These data show that the plasma insulin levels obtained using MTLP-insulin particle complexes, were greater than those obtained using the targeting peptide-insulin particle complexes.

Figure 3:
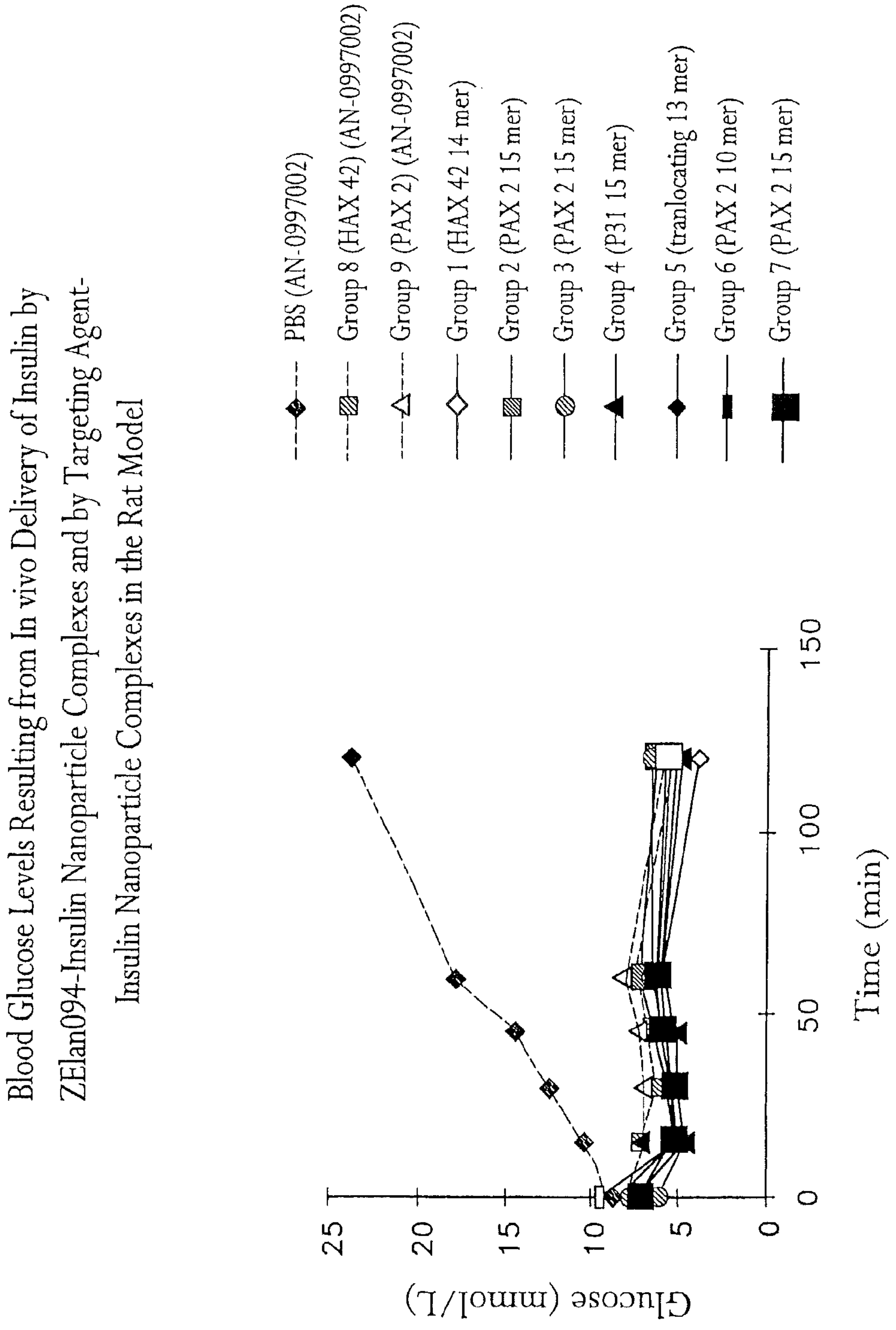
FIG. 3 shows the systemic blood glucose levels following in vivo delivery of insulin from a ZElan094-insulin nanoparticle complex and from HAX42-, PAX2- and P31-insulin nanoparticle complexes in the open loop rat model. Each point is the mean of 6-7 animals.

To ensure that the insulin delivered from the MTLP-insulin particle complexes and from the targeting peptide-insulin particle complexes was bioactive, blood glucose levels were measured. As shown in FIG. 3, during the 20 minutes following intra-duodenal administration, blood glucose levels fell from between about 6.0-9.5 mmol/L to about 4.5-7.0 mmol/L and remained significantly below control values (PBS) for at least 60 minutes. There was no significant differences in blood glucose levels among the animals receiving the MTLP-insulin particle complexes and the animals receiving the targeting peptide-insulin particle complexes at 60 minutes and at 120 minutes. These data show that insulin delivered from the dansylated ZElan094-insulin particle complexes and from the dansylated Zelan011, 055, 091, 144, 129, 101, 129, 128 and 104-insulin particle complexes remained bioactive. Further, these data show that insulin delivered from MTLP-insulin particle complexes enabled a significant and long lasting decrease in blood glucose levels.

Example 9

Preparation of DNA Containing Liposomes and of DNA Containing MTLP Coated Liposomes DNA containing liposomes and DNA containing MLTP coated liposomes were prepared as follows:

Solution 1 Twelve nmol lipofectamine (Gibco BRL, Rockville, Md.), ±0.6 mg of protamine sulphate, was prepared in a final volume of 75 ml optiMEM.

Solution 2 One mg of pHM6lacZ DNA (Boehringer Mannheim) was prepared in a final volume of 75 ml optiMEM. The reporter plasmid pHM6lacZ contains the lacZ gene, which codes for bacterial β-galactosidase.

Solution 3 Solution 1 and Solution 2 were combined and incubated for 15 minutes at RT to enable complex formation.

Solution 4 ZElan094, 204N or 204 (SEQ ID Nos: 2, 23, 24) were added to Solution 3 to a final concentration of 100 mM and incubated for 5 minutes at RT. Six-hundred ml of opti-MEM was added and the solution was mixed gently.

The DNA containing liposomes and the DNA containing MTLP coated liposome complexes were analyzed in scanning electron microscopy (SCM) or in transmission electron microscopy (TEM) to confirm complex liposome formation and by zeta potential analysis to confirm surface charge properties.

Example 10

Delivery of DNA from Liposomes and from MTLP-Liposomes into Caco-2 Cells

DNA delivery into Caco-2 cells from liposomes and from MTLP coated liposomes was calculated as β-galactosidase expression per mg of total protein in the cell supernatant. β-galactosidase expression was determined using the Boehringer Mannheim chemiluminescence kit. Protein was determined using the Pierce Micro bichinconate (BCA) protein assay.

Caco-2 cells were plated at $1\times10^5$ cells/well in 1 ml of culture media and incubated at 37° C. in 5% $CO_2$ overnight. The cells were washed twice in 0.5 ml of optiMEM. ZElan094, 204N or 204 (SEQ ID NOS: 2, 23, 24) (Solution 4, Example 9) were each added to triplicate wells (250 μl/well) of the washed cells and incubated for 4 h at 37° C. After 4 h, 250 μl of optiMEM containing 2× fetal calf serum was added and the cells were incubated for an additional 20 h at 37° C. At 24 h post-transfection, the cells were lysed with Boehringer Mannheim Lysis Buffer. The lysate was centrifuged for 2 min at 14,000 rpm in an Eppendorf Centrifiguge and the supernatant was collected.

Table 5 shows relative β-galactosidase expression per mg of total protein using ZElan094, ZElan204N and ZElan204 (SEQ ID NOS: 2, 23, 24) coated liposomes as the DNA delivery particles.

TABLE 5

| β-galactosidase expression in Caco-2 cells | | |
|---|---|---|
| | EXPERIMENTS | |
| | 1 | 2 |
| Lipofectamine + DNA (control) | 100% | 100% |
| Lipofectamine + DNA + protamine (control) | 90% | 162% |
| Lipofectamine + DNA + protamine + ZElan094 | 387% | 260% |
| Lipofectamine + DNA + protamine + ZElan204N | 495% | 217% |
| Lipofectamine + DNA + protamine + ZElanN204 | 176% | 122% |

The MLTPs ZElan094, 204N and N204 (SEQ ID NOS: 2, 23 and 24) coated liposomes delivered more DNA into the Caco-2 cells than did the lipofectamine+DNA and lipofectamine+DNA+protamine control liposomes. Moreover, as indicated by b-galactosidase expression, the ZElan094 derivative ZElan204N, which is modified at the C-terminus by the addition of a nuclear localisation sequence (NLS), was most effective in enhancing both delivery of DNA into and expression of DNA within Caco-2 cells. The MTLP ZElan094 and its derivatives, in combination with cationic lipids and DNA condensing agents, enhanced both the targeting of genes to cells and the subsequent uptake of the genes by the cells.

As MTLPs enhance uptake of both active-agents and active-particles into cells, MTLPs including, but not limited to, ZElan094 and ZElan 204N, can be used as coating agents on polymer based particle systems and on liposome based particle systems as active agent and active particle delivery systems. Further, MTLPs also can be used as coating agents on viral vector based particle systems including, but not limited to, adenovirus, adeno-associated virus, lentivirus, and vaccinia virus. In such systems, the virus itself may code for the MTLP, wherein the DNA sequence coding for the MTLP has been cloned in frame to one or more genes which code for one or more viral capsid protein or for one or more viral surface proteins. Alternatively, the surface of the virus used for gene delivery may be modified with a MTLP following virus production and purification from a cell including, but not limited to, a mammalian cell.

Example 11

Effects of MTLPs and of the Targeting Peptides on Substrate Transport Across a Cell Layer The effect of the MTLPs ZElan094, ZElan178 and ZElan187 (SEQ ID NOS: 2, 7 and 16) and of the targeting peptide ZElan022 (U.S. patent application Ser. Nos. 09/079,819, 09/079,723 AND 09/079,678, AND PCT APPLICATION PCT/US98/10088, PUBLISHED AS WO 98/51325) on the transport of the dipeptide $^{14}$C-gly-sar and of the reporter molecule $^{3}$H-fMLP across Caco-2 monolayers was determined. The Caco-2 monolayers were grown on Transwell-Snapwells. Cell viability was determined by measuring TEER of the Caco-2 monolayers during each experiment. No significant drop in TEER was measured. Cell permeability was determined by measuring mannitol flux across the Caco-2 monolayers during each experiment. No increase in mannitol flux was measured in the presence of the MTLP ZElan094.

The flux of the dipeptide $^{14}$C-gly-sar and of the reporter molecule $^{3}$H-fMLP across the Caco-2 monolayers in the absence and in the presence of the MTLPs ZElan094, ZElan178 and ZElan187 (SEQ ID NOS: 2, 7 and 16) and of the targeting peptide ZElan022 (U.S. patent application Ser. Nos. 09/079,819, 09/079,723 AND 09/079,678), AND PCT APPLICATION PCT/US98/10088, PUBLISHED AS WO 98/51325 was measured over 2 h, and reduction in the permeability coefficient was determined in the presence of cold substrates.

Figure 4:
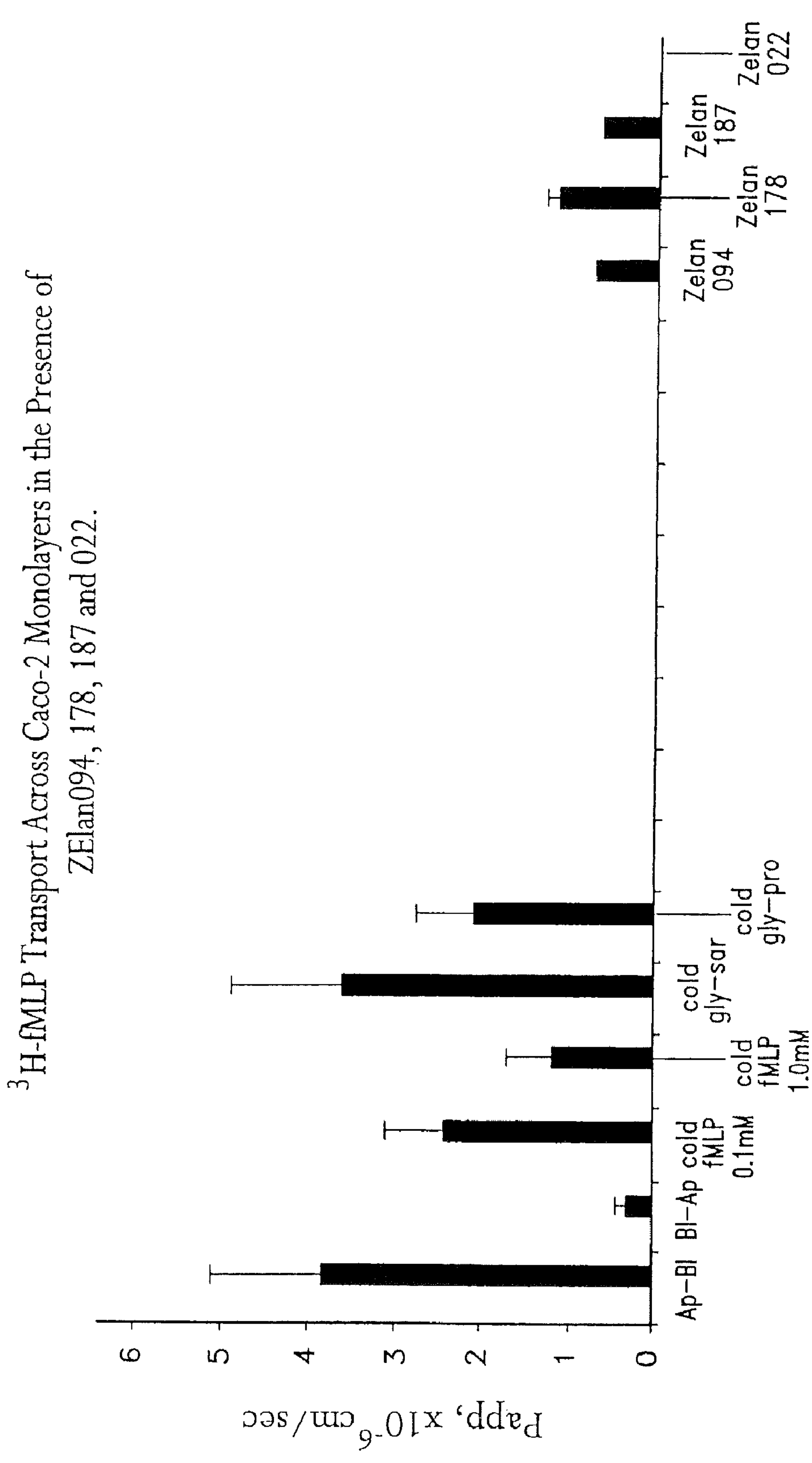
FIG. 4 shows the transport of the reporter drug $^3$H-fMLP across Caco-2 monolayers in the presence of the MTLPs ZElan094, 178, 187 and the targeting peptide ZElan022.

As shown in Table 6, the MTLPs ZElan 094, 178 and 187 inhibited transport of the reporter molecule $^{3}$H-fMLP (FIG. 4), but did not inhibit transport of the dipeptide $^{14}$C-gly-sar. The targeting peptide ZElan 022 inhibited transport of the reporter molecule $^{3}$H-fMLP (FIG. 4). The ability of the MTLPs ZElan094 178 and 187 to compete for the transport of fMLP across polarised Caco-2 cells indicates that this novel transport assay can be used to screen derivatives, fragments, motifs, analogs and peptidomimetics of ZElan094 and small organic molecules functionally similar to ZElan094 to identify those having improved transport characteristics.

TABLE 6

Transport studies

| ZElan N0: | SEQ ID NO: | % inhibition $^{3}$H-fMLP transport | % inhibition $^{14}$C-gly-sar transport |
|---|---|---|---|
| 094 | 2 | 77.2 | NS |
| 178 | 7 | 71.5 | NS |
| 187 | 16 | 84.5 | NS |
| 022 | U.S. patent application Ser. Nos. 09/079,819, 09/079,723 AND 09/079,678,, AND PCT APPLICATION PCT/US98/10088, PUBLISHED AS WO 98/51325 | 00.0 | |

NS: no significant difference between experimental (+MTLP) and control cells (−MTLP) in the transport of radiolabeled drug.

Moreover, that the MTLPs inhibited transport of the reporter molecule $^{3}$H-fMLP, but did not inhibit transport of the dipeptide $^{14}$C-gly-sar suggest that their effect on fMLP transport is not due to a generalized perturbation of the membranes in polarized epithelial cells. Further, as fMLP is known to play a role in inflammation in the GIT, MTLPs, which decrease transport of fMLP across Caco-2 monolayers, may have a therapeutic role in preventing local inflammation by decreasing the chemoattractant effect of fMLP in the GIT.

Example 12

Figure 5:
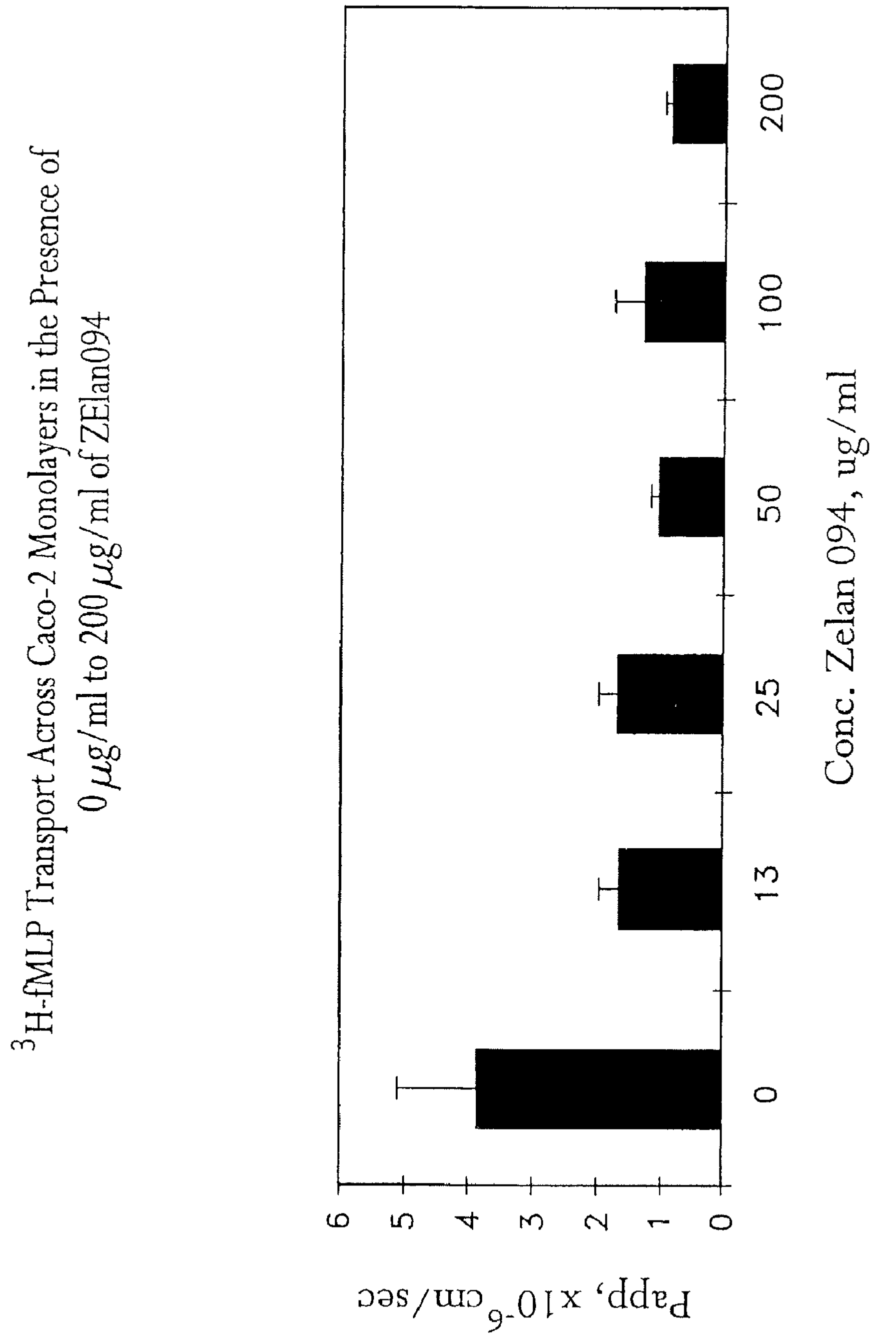
FIG. 5 shows the transport of the reporter drug $^3$H-fMLP across Caco-2 monolayers in the presence of increasing concentrations of the MTLP ZElan094.

Effect of Increasing Concentrations of an MTLP on the Transport of $^{3}$H-fMLP Across a Cell Layer Caco-2 monolayers were grown and tested for viability as in Example 11. Transport of $^{3}$H-fMLP across Caco-2 monolayers was measured in the presence from 0 to 200 μg/ml of the MTLP ZElan094. As shown in FIG. 5, the MTLP ZElan094 inhibited $^{3}$H-fMLP transport even at the lowest concentration (13 mg/ml or 7.1 ml) tested. This indicates that the MTLP ZElan094 is a potent inhibitor of fMLP transport across an epithelial cell layer.

Example 13

Stability of MTLPs in Simulated Intestinal Fluid

MTLPs ZElan094 and ZElan207 (SEQ. ID NO: 2 and 60) were dissolved in water and mixed with simulated intestinal fluid pH 6.8 containing porcine derived pancreatin (SIF+Pancreatin) at 37° C. The mixtures were incubated for up to 60 minutes at 37° C., with aliquots taken at designated time points. The reaction was quenched with quenching solution after the relevant time points in order to halt the reaction between the SIF and ligand.

The composition of Simulated Intestinal Fluid was as follows:

Amylase 25 USP Units
Lipase 2.0 USP units
Protease 25 USP units
(Sigma P8096)

Approximately 1 mg of ligand was dissolved in 1 ml of water. This standard stock solution of ligand was used to prepare the solutions containing Ligand+SIF+Pancreatin. 50 μL of ligand solution was mixed with volumes of SIF+Pancreatin in separate eppendorfs, as follows:

TABLE 7

| Volume of Ligand Solution (μL) | Volume of SIF (μL) | Temperature (° C.) | Time (minutes) |
|---|---|---|---|
| 50 | 100 | 37 | 5 |
| 50 | 100 | 37 | 10 |
| 50 | 100 | 37 | 30 |
| 50 | 100 | 37 | 60 |

TABLE 7-continued

| Volume of Ligand Solution (μL) | Volume of SIF (μL) | Temperature (° C.) | Time (minutes) |
|---|---|---|---|
| 50 | 200 | 37 | 5 |
| 50 | 200 | 37 | 10 |
| 50 | 200 | 37 | 30 |
| 50 | 200 | 37 | 60 |

Two different volumes of SIF were utilised in order to monitor if increasing the SIF:ligand ratio had an effect on the extent and rate of degradation. At the appropriate time point the reaction between the ligand and SIF was stopped by pipetting 100 μL of the mixture into 500 μL of quenching solution (Acetonitrile:Water 30:70). 20 μL of the mixture was injected onto the HPLC system.

HPLC Experimental

Column: Jupiter $C_{18}$ RP, 5 μm, 300 Å, 250×4.6 mm, TCD #188

Mobile phase: A: 10% acetonitrile in 0.1% trifluoroacetic acid in water

B: 0.1% trifluoroacetic acid in acetonitrile

Flow rate: 1.0 ml/min

Temperature: ambient

Injection volume: 20 μl

Detector λ: 220 nm

Run time: 38 minutes

Control samples of ligand in water and in quenching solution were prepared to check for recovery of ligand in the absence of SIF+Pancreatin.

No recovery for ligand ZELAN094 (SEQ ID NO 2) was obtained at any of the time points. Degradation products were seen in the chromatogram.

No result table is presented for ZELAN094 as no recovery was obtained for any of the time points. This is demonstrated by the disappearance of the peptide peak. This ligand is therefore degraded almost immediately on contact with SIF medium. Degradation products appear at retention times 12.258, 13.55 and 14.067 minutes.

The controls demonstrated that the peptide is not degraded at 37° C. over time when SIF+Pancreatin are not present. Also, the quenching solution does not affect the recovery. It should be remembered that while the HPLC method used above has not been optimised as a stability-indicating assay, the disappearance of the ligand peaks and appearance of new component peaks were clearly visible.

The recovery of ZELAN207 (SEQ ID NO 60) from SIF solutions is tabulated below.

TABLE 8

Stability of peptide ZELAN 207 (Lot# 11243) in presence of SIF (USP) pH 6.8 at 37 C.

| Sample | Time point (min) | Std area (mean) | Std precision (% CV) | Std Conc (ug/ml) | Sample Area | Actual Conc Drug (ug/ml) | Theoretical Drug Conc (ug/ml) | % Recovery |
|---|---|---|---|---|---|---|---|---|
| Peptide + 100 uL SIF | 5 | 2012290 | 0.9 | 60.63 | 1727236 | 52.04 | 53.9 | 96.6 |
| | 10 | 2012290 | 0.9 | 60.63 | 1742290 | 52.49 | 53.9 | 97.4 |
| | 30 | 2012290 | 0.9 | 60.63 | 1571456 | 47.35 | 53.9 | 87.8 |
| | 60 | 2012290 | 0.9 | 60.63 | 1747950 | 52.67 | 53.9 | 97.7 |
| Peptide + 200 uL SIF | 5 | 2013467 | 1.0 | 60.63 | 1062099 | 31.98 | 32.3 | 99.0 |
| | 10 | 2013467 | 1.0 | 60.63 | 1032597 | 31.09 | 32.3 | 96.3 |
| | 30 | 2013467 | 1.0 | 60.63 | 995036 | 29.96 | 32.3 | 92.8 |
| | 60 | 2013467 | 1.0 | 60.63 | 1035460 | 31.18 | 32.3 | 96.5 |
| Pep + H2O (100 ul) + Q* | 60 | 2016394 | 1.1 | 60.63 | 1810419 | 54.44 | 53.9 | 101.0 |
| Pep + H2O (100 ul) + H2O | 60 | 2016394 | 1.1 | 60.63 | 1806474 | 54.32 | 53.9 | 100.8 |

*Q = quenching solution

Incubation with SIF for up to 1 hour allowed recovery of >90% of the parent peptide indicating that D-amino acid substitution substantially increased the stability profile for the peptide.

Example 14

Evaluation of MTLPs for Delivery of a Model Opioid Peptide In Vitro (Caco-2) and In Vivo (Intraduodenal; Conscious Rat Model)

A. Opioid Peptide Stability in SIF

A model D-form opioid peptide (H-ffir-NH2; kappa receptor specific; molecular weight 581 Da) was evaluated for stability in SIF.

Pancreatin (Fisher Scientific) was dissolved at 1 mg/ml in 1× phosphate buffer solution. The pH of the solution was adjusted to 7.5 with 0.01 M NaOH and it was heated in a waterbath to 37° C. Two dry peptide samples were weighed out. One sample was dissolved in phosphate buffer solution at 1.0 mg/ml as a control. The second sample was dissolved in SIF at 1.0 mg/ml for stability analysis.

HPLC Analysis Conditions

RP-HPLC analysis with C-18 short column (Betasil column, 5 μm (50×3 mm) PN: 055-701-3) with the following gradient:

| Time (min) | Solvents Mixture |
|---|---|
| 0 | 95% water-5% acetonitrile (0.05% TFA) |
| 0 | 95% water-5% acetonitrile (0.05% TFA) |
| 0 | 5% water-95% acetonitrile (0.05% TFA) linear solvent gradient |
| 8 | 5% water-95% acetonitrile (0.05% TFA) |

Diode array detector on the system, 214 nm used for analysis

Peptide control initially injected

Solution in SIF injected at 0, 1, 3, and 24 hours

LCMS Analysis

Analyzed control and 24 hour sample by LCMS.

The kappa peptide, H-ffir-NH2, was very stable over the 24 hour period (see Table 9). Mass spectrometry confirmed this result with only one compound detectable initially and after 24 hours. The kappa peptide was selected as a suitable model drug for further evaluation in targeting studies.

TABLE 9

| H-ffir-NH2 | Control RT | Area | Initial RT | Area | 1 hr RT | Area | 24 hr RT | Area |
|---|---|---|---|---|---|---|---|---|
| | 0.467 | 347767 | 0.467 | 336841 | 0.467 | 360462 | 0.467 | 330859 |
| | | | 2.133 | 249457 | 2.117 | 285901 | | |
| | 2.333 | | 2.317 | 11107788 | 2.317 | 11691106 | 2.317 | 11215885 |
| Sequence | H— | | f | | f | i | r | —NH2 |
| % Compound | 1 hr | | 105.25% | | | | | |
| | 24 hr | | 100.97% | | | | | |

In Table 10, 3 Elan207 (SEQ ID NO 60) conjugates are compared to the H-ffir-NH2 (SEQ ID NO:113) peptide control (unconjugated). The three conjugates are 1) H-ffir-NH2 (SEQ ID NO:113) conjugated to N-terminal of 207 through a lysine linker (P10-110), 2) H-ffir-NH2 (SEQ ID NO:113) conjugated to C-terminal of 207 through a lysine linker (P10-114) and 3) H-ffir-NH2 (SEQ ID NO:113) conjugated to N-terminal of 207 directly i.e. no linker (P10-118). Assays were performed on 3 separate occasions (duplicates on day 5 and triplicates on day 82). Opioid activity is significantly reduced by conjugation as described in 1) and 3). Using 2) i.e. C-terminus and lysine linker the opioid activity is retained, or even enhanced suggesting the need for the linker amino acid and/or conformation induced in this format. The assay is cell based and subject to some variation-however the trend remains consistent throughout.

IC50 values indicated that optimal opioid activity was retained post conjugation of the opioid peptide to the C-terminus of the ELAN207 MTLP through a lysine linker. Note that the opioid activity may have been enhanced by addition of ELAN207.

In Table 11, ELAN094, 178, 207 & 208 (SEQ ID NOS: 109, 110, 111 and 112) biotin labelled conjugates are compared to the H-ffir-NH2 peptide control (unconjugated).

B. Synthesis and Evaluation of Kappa Peptide Conjugates In Vitro

Conjugates of the kappa peptide, H-ffir-NH2, and various MTLPs (ELAN094, ELAN207, ELAN208 & ELAN178) were synthesised in various formats to determine optimal conjugation strategies for subsequent synthesis of batches for in vivo evaluation. Structural formats included:

i) C-terminal or N-terminal opioid peptide, ii) Conjugated with/without a lysine linker, iii) Unlabelled/biotin labelled.

The integrity of the opioid peptide was evaluated post conjugation to assess suitability for inclusion in further studies. Opioid activity was assessed in vitro using a competition assay (competition for binding of a radiolabelled kappa peptide to rat brain homogenates). Results are expressed as IC50 values i.e. the concentration of conjugate which inhibits binding of the radiolabelled ligand by 50%.

TABLE 10

| Cmpnd | # M.W. | M.W | Day 1 IC50 nM | Day 5 IC50 nM | IC50 nM | Day 82 IC50 nM | IC50 nM | IC50 nM |
|---|---|---|---|---|---|---|---|---|
| P10- | 110 H-ffirk(kkaaavllpvllaap-NH-e)-NH2 (SEQ ID NO: 106) | 2166 | 52.1 | 81.8 | 181.8 | 25.9 | 17.1 | 19704.9 |
| P10- | 114 H-kkaaavllpvllaapk(ffir-NH-e)-NH2 (SEQ ID NO: 107) | 2166 | 3.7 | 19.9 | 1.0 | 0.8 | 0.8 | 4.4 |
| P10- | 118 H-ffirkkaaavllpvllaap-NH2 (SEQ ID NO: 108) | 2038 | 113.1 | 63.0 | 302.5 | 177.1 | 38.8 | 189.9 |
| | H-ffir-NH2 (SEQ ID NO: 113) | | | 14.0 | 3.3 | 4 | 1.7 | 3.9 |

TABLE 11

| | | ELAN No. | MW | IC50 nM | IC50 nM |
|---|---|---|---|---|---|
| P37-114 | H-K(biotin-LC)KKAAAVLLPVLLAAPK(ffir-NH-e)-NH2 (SEQ ID NO: 109) | 94 | 2633 | 0.4 | 7.9 |
| P37-116 | H-K(biotin-LC)KKCAAVLLPVLLACK(ffir-NH-e)-NH2 (SEQ ID NO: 110) | 178 | 2598 | 0.2 | 11.7 |
| P34-154 | H-K(biotin-LC)kkaaavllpvllaapk(ffir-NH-e)-NH2 (SEQ ID NO: 111) | 207 | 2633 | 1.1 | 12.4 |
| P37-115 | H-K(biotin-LC)paallvpllvaaakkK(ffir-NH-e)-NH2 (SEQ ID NO: 112) | 208 | 2633 | 9.2 | 9.8 |
| | H-ffir-NH2 (SEQ ID NO: 113) | | | 1.7 | 3.9 |

IC50 Values Indicated that:

i) the ELAN207 opioid peptide conjugate (P34-154) retained activity post biotin labelling ii) ELAN094 (P37-114), 178 (P37-116) & 208 (P37-115) opioid peptide conjugates, with C-terminal opioid peptide and lysine linker, exhibited activity equivalent to that observed with ELAN207 (P34-154).

Peptide conjugates P37-114 (ELAN094) and P34-154 (ELAN207) were synthesised in a tritium labelled format for in vivo studies.

Example 15

C. Synthesis and Evaluation of Tritiated Kappa Peptide Conjugates In Vitro

Conjugates of the kappa peptide, H-ffir-NH2, and MTLPs ELAN094 and ELAN207 (SEQ ID NOs 2 and 60), were synthesised using standard peptide synthesis protocols. Two phenylalanine residues on the kappa peptide were labelled by tritium exchange and radio-peptide purity was assessed by RP-HPLC. Peptide purity of >95% and specific activities of 42-54 Ci/mmol were achieved.

The tritiated opioid peptide conjugates were evaluated for permeability through differentiated Caco-2 cell monolayers i.e. to assess the integrity of the membrane translocating peptide moiety Both the kappa peptide conjugates and the kappa peptide control exhibited permeability coefficients in the $10^{-6}$ cm/sec range, indicating that they would be suitable candidates for oral bioavailability evaluation in vivo. No significant increase in permeability was detectable when the ZELAN094 or ZELAN207 peptide conjugates were compared to the kappa peptide control (n=5). Highest transport values were obtained in the first 30 min followed by a 2-4 fold decrease at 60 min. The significance of these findings is unclear. The data may be indicative of dual binding/uptake events occurring through i) a kappa receptor specific mechanism and ii) direct membrane interaction through lipid interaction of the membrane permeable peptide.

FIG. 6 shows results on the transport of tritiated kappa peptide conjugates and kappa peptide control across differentiated Caco-2 cell monolayers.

D. Evaluation of Tritiated Kappa Peptide Conjugates In Vivo

The possible enhancing effects of ELAN094 and ELAN207 MTLPs (SEQ ID NOs 2 and 60) on intestinal absorption of the kappa peptide were examined in a conscious rat model.

Experimental:

The study was non-randomised, parallel group design. Wistar rats within the 250-350 g weight range were used. All animals were fasted for a period of 16 h prior to study initiation. Water was available at all times.

Treatment Regimen:

Group 1 (n=6)

Intravenous injection of 10 μCi of $^3$H-kappa peptide-Kaffiralin-1 (plain kappa peptide) (tail vein injection).

Group 3 (n=6)

Intraduodenal instillation of 100 μCi of $^3$H-kappa peptide-Elan094 (Analysed). The Elan094 ligand contains a membrane translocating sequence.

Group 4 (n=6)

Intraduodenal instillation of 100 μCi of $^3$H-kappa peptide-Elan207 (Analysed). The Elan207 ligand contains a membrane translocating sequence.

Group 10 (n=6)

Intraduodenal instillation of 100 μCi of $^3$H-kappa peptide-Kaffiralin-1.

$^3$H Bio-Analysis: Plasma Samples

The plasma (100-250 μl) was made up to 1 ml with BTS-450 (an organic tissue solubiliser) and incubated for 1 hour. Ten ml of Scintillation fluid was added and the radioactivity was measured.

Results:

The study was a non-randomised, parallel group biostudy designed to evaluate the systemic bioavailability of tritium labelled kappa peptide conjugates after intra-duodenal instillation in the conscious rat model. Each rat only received one treatment and the plasma samples were analysed for tritium content. The calculation of AUClast, Amax, tmax, Volume of Distribution (V d) and Clearance was based on base line corrected data. The absolute bioavailability was calculated using potency corrected data.

Stock solutions of the tritiated ligand were administered to the rats on different dates. These stock solutions were analysed in order to correct for potency. Data analysed on one particular day suggested a discrepancy in the bioavailability for Group 4 and a repeat of Group 4. It was decided to re-analyse the stock solution administered to Group 4 (repeat). The potency correction factor for all treatments, including the re-analysis of Group 4 (repeat), are summarised below:

Potency Correction Analysis:

TABLE 12

| Day received | Theoritical Value uCi/ml | Group No. | Ligand | dpm/100 ul | dpm/ml | Actual Value uCi/ml | % of theo dose | Potency Corr. Factor |
|---|---|---|---|---|---|---|---|---|
| 1 | 303 | 10 | Kappa-peptide | 74811764 | 748117640 | 336.990 | 111.22 | 0.899 |
| 6 | 303 | 10 | Kappa-peptide | 47279266 | 472792660 | 212.970 | 70.29 | 1.423 |
| 13 | 303 | 4 | Elan207 | 83174222 | 831742220 | 374.659 | 123.65 | 0.809 |
| 21 | 303 | 4 | Elan207 | 83186452 | 831864520 | 374.714 | 123.67 | 0.809 |
| 27 | 50 | 1 | Kappa-peptide | 12839706 | 128397060 | 57.837 | 115.67 | 0.865 |
| 48 | 303 | 3 | Elan094 | 32985636 | 329856360 | 148.584 | 49.04 | 2.039 |
| 62 | 303 | 4 (Repeat) | Elan207 | 44012732 | 440127320 | 198.256 | 65.43 | 1.528 |
| 113 | 303 | 4 (Repeat) | Elan207 | 88311270 | 883112700 | 397.799 | 131.29 | 0.762 |

Day numbers are unrelated to those in Table 10.

The absolute bioavailability and mean pharmacokinetic parameters are summarized below.

Absolute $^{3}H$ Bioavailability (%)

The absolute $^{3}H$ bioavailability for the treatments in rank order were the following: for Treatment 3-100 μCi $^{3}H$-Kappa peptide-Elan094 (ID) was 46.48±6.24% (CV 13.4%), for Treatment 4-100 μCi $^{3}H$-Kappa peptide Elan207 (ID) (Repeat) was 16.60±2.50% (15.1%), for Treatment 4-100 μCi $^{3}H$-Kappa peptide Elan207 (ID) (original) was 11.52±0.96% (CV 8.3%), and in the absence of delivery enhancer ligand Treatment 10-100 μCi $^{3}H$-Kappa peptide Kaffiralin-1 (ID) was 7.94±1.92% (CV 24.1%). This represents approximately a 6 fold increase in delivery with Treatment 3-100 μCi $^{3}H$-Kappa peptide-Elan094 (ID), approx. 2 fold increase with Treatment 4-100 μCi $^{3}H$-Kappa peptide Elan207 (ID) (Repeat). A similar delivery was observed with Treatment 4-100 μCi $^{3}H$-Kappa peptide Elan207 (ID) (original) as compared to the absolute $^{3}H$ bioavailability of Kappa-peptide in the absence of enhancer ligand Treatment 10-100 μCi $^{3}H$-Kappa peptide Kaffiralin-1 (ID).

$^{3}H$ AUClast (dpm/ml·h)

The AUClast for the ID treatments in rank order were as follows: for Treatment 3-100 μCi $^{3}H$-Kappa peptide-Elan094 (ID) was 260642.53±35010.58 dpm/ml·h (CV 13.4%), for Treatment 4-100 μCi $^{3}H$-Kappa peptide Elan207 (ID) (Repeat) was 249021.32±37503.78 dpm/ml·h (CV 15.1%), for Treatment 4-100 μCi $^{3}H$-Kappa peptide-Elan207 (ID) (original) was 162743.70±13549.10 dpm/ml·h (CV 8.3%), for Treatment 1-10 μCi $^{3}H$ Kappa Peptide-Kaffiralin-1 (IV) was 132184.24±13288.32 dpm/ml·h (CV 10.1%), while in the absence of ligand Treatment 10-100 μCi $^{3}H$-Kappa peptide Kaffiralin-1 (ID) was 73098.43±9493.88 dpm/ml·h (CV % 13.0).

$^{3}H$ Amax (dpm/ml)

The maximum radioactivity following administration of the ID treatments in order of magnitude were as follows: for Treatment 1-10 μCi $^{3}H$ Kappa Peptide-Kaffiralin-1 (IV) was 903603.03±186855.31 dpm/ml (CV 20.7%), for Treatment 4-100 μCi $^{3}H$-Kappa peptide Elan207 (ID) (Repeat) was 201464.40±44854.19 dpm/ml (CV 22.3%), for Treatment 3-100 μCi $^{3}H$-Kappa peptide-Elan094 (ID) was 158512.67±18907.79 dpm/ml (CV % 11.9), for Treatment 4-100 μCi $^{3}H$-Kappa peptide Elan207 (ID) (original) was 100041.17±6274.57 dpm/ml (CV % 6.3), for Kappa-peptide alone Treatment 10-100 μCi $^{3}H$-Kappa peptide Kaffiralin-1 (ID) was 70925.33±23631.28 dpm/ml (CV % 33.3).

$^{3}H$ Tmax (h)

The time to reach maximum radioactivity was 0.08±0.00 h for all ID treatments.

Volume of Distribution (ml)

The observed volume of distribution for Trt 1 10 μCi 3H-Kappa peptide-Kaffiralin-1 (IV) was 963.87±255.65 ml (CV 26.5%).

Clearance (ml/h)

The observed clearance for Trt 1 10 μCi 3H-Kappa peptide-Kaffiralin-1 (IV) was 142.85±17.24 ml/h (CV 12.1%).

The Elan207 MTLP (SEQ ID NO 60) showed absolute $^{3}H$ bioavailability in excess of 1.5 fold increase respectively in comparison to administration of the kappa peptide control. Following re-analysis of the stocks for Group 4 (repeat), the recalculated absolute bioavailability was comparable to that observed for Group 4 (original). The correlation of this repeat data, together with the observed stability of the ELAN207 and kappa peptides in simulated intestinal fluid, would suggest that the observed radioactivity is associated with presence of the intact radio-peptide conjugate in the plasma. The radioactivity profiles will be correlated with LCMS analysis of plasma samples exhibiting high tritium counts for verification.

The Elan094 MTLP (SEQ ID NO 2) showed absolute $^{3}H$ bioavailability in excess of approximately 5.8 fold compared to administration of the kappa peptide control. Note that the inherent instability of the ELAN094 peptide in simulated intestinal fluid would suggest that the radioactivity profile should be interpreted with caution in this instance. It is possible that the parent ELAN094 kappa peptide conjugate has deteriorated in vivo and thus, the observed radioactivity may not be associated with presence of the intact radio-peptide conjugate in the plasma.

A rapid delivery of $^{3}H$ kappa-peptide was detected in all treatments with observed tmax of 0.08 h for all treatments. This suggests that the kappa peptide rapidly crossed the gastrointestinal barriers into the systemic circulation. It should be noted that as the absorption was very rapid, the AUC might be underestimated due to the fact that the maximum radioactivity was measured in the first sampling point (5 minutes after dosing).

$^{3}H$ Bio-Analysis: Tissue Samples

The tissue was weighed and a representative sample, (ca 0.1 g), was removed to a scintillation vial. The tissue was solubilzed with 1 ml of BTS-450 (an organic tissue solubliser). Ten ml of scintillation fluid was added and the radioactivity was measured. The radioactivity was expressed as dpm/initial weight of tissue.

Results:

The results are summarized in Table 14.

TABLE 14

| Summary Table % of administered dose (Mean ± SD - CV %) (Potency corrected data) | | | | |
|---|---|---|---|---|
| % of Admin. Dose | Group 1 - 10 μCi 3H-Kappa peptide-Kaffiralin-1 (IV) n = 6 | Group 3 - 100 μCi 3H-Kappa peptide-Elan094 (IDV) n = 6 | Group 4 - 100 μCi 3H-Kappa peptide-Elan 207 (ID) n = 6 | Group 10 - 100 μCi 3H-Kappa peptide-Kaffiralin-1 (ID) n = 6 |
| *Total Recovery (%) | 34.43 ± 13.36 | 46.00 ± 19.91 | 40.91 ± 23.32 | 61.79 ± 16.93 |
| (CV %) | 38.8 | 43.3 | 57.0 | 27.4 |
| Catheter (%) | — | 0.20 ± 0.10 | 0.14 ± 0.09 | 0.06 ± 0.05 |
| (CV %) | — | 49.3 | 63.4 | 88.8 |
| Plasma (%) | 0.16 ± 0.03 | 0.42 ± 0.08 | 0.10 ± 0.01 | 0.06 ± 0.01 |
| (CV %) | 18.9 | 17.7 | 9.2 | 11.6 |
| Liver (%) | 6.66 ± 1.77 | 0.37 ± 0.06 | 0.47 ± 0.20 | 0.63 ± 0.37 |
| (CV %) | 26.6 | 17.3 | 41.9 | 57.9 |
| Kidney (%) | 0.51 ± 0.08 | 0.12 ± 0.07 | 0.17 ± 0.07 | 0.16 ± 0.17 |
| (CV %) | 16.1 | 54.1 | 40.6 | 109.6 |
| GI Tissue (%) | 1.62 ± 0.41 | 11.61 ± 11.27 | 4.08 ± 2.47 | 7.72 ± 4.98 |
| (CV %) | 25.4 | 97.1 | 60.4 | 64.5 |
| GI contents (%) | 23.50 ± 11.04 | 23.57 ± 21.57 | 26.34 ± 17.00 | 37.31 ± 15.75 |
| (CV %) | 47.0 | 91.50 | 64.5 | 42.2 |
| GI Washing (%) | 1.98 ± 1.01 | 9.70 ± 5.24 | 9.60 ± 16.65 | 15.85 ± 5.00 |
| (CV %) | 51.1 | 54.1 | 173.4 | 31.5 |
| Total GI (% recovery from GI tissue, GI contents & GI wash) | 27.10 ± 11.93 | 44.89 ± 19.94 | 40.03 ± 23.23 | 60.87 ± 16.74 |
| (CV %) | 44.0 | 44.4 | 58.0 | 27.5 |

Summation of radioactivity recovered from catheter, plasma, all tissues, GI contents & GI washing expressed as a percentage of administered dose The tissue distribution following IV administration in rank order were as follows: GI contents>Liver>GI Washing>GI Tissue>Kidney>Plasma. Assuming the $^3$H label remained attached to the Kappa-peptide, this data suggests that following IV administration the administered $^3$H Kappa-peptide-Kaffiralin-1 had widely distributed throughout the rat and was concentrated mainly in the GI, particularly in GI contents. The concentration in GI contents may possibly be due to biliary excretion. However only 34.43±13.36% (CV 38.8%) of administered dose had been recovered at t=6 h suggesting some Kappa-peptide had been excreted or had possibly distributed to other sites.

% Recovered in Catheter

The % of administered dose recovered in the catheter, for the various treatments, ranged from 0.06-0.39%. This data suggests that a negligible amount of the administered dose is lost in the catheter.

% Recovered in Plasma

The % of administered dose recovered in plasma was calculated at t=6 h. The % of administered dose ranged from 0.06-0.42% for the various treatments. The rank order for the various treatments were as follows: for Treatment 3-100 μCi $^3$H-Kappa peptide-Elan094 (ID) was 0.42±0.08% (17.7%), for Treatment 1-10 μCi $^3$H Kappa peptide-Kaffiralin-1 (IV) was 0.16±0.03% (CV 18.9%), for Treatment 4-100 μCi $^3$H-Kappa peptide Elan207 (ID) (original) was 0.10±0.01% (CV 9.2%), and in the absence of delivery enhancer ligand Treatment 10-100 μCi $^3$H-Kappa peptide Kaffiralin-1 (ID) the % of administered dose was 0.06±0.01% (CV 11.6%). This rank order correlates identically with that observed for absolute bioavailability reported in the data pack for Biostudy 1000003 for the various treatments.

% Recovered in Liver

The % of administered dose recovered in the liver ranged from 0.26-6.66%. Following IV administration, Treatment 1-10 μCi $^3$H Kappa peptide-Kaffiralin-1 (IV), the % recovery was 6.66±1.77% (CV 26.6%). This recovery far exceeded the amount recovered in liver tissue for any other treatments.

% Recovered in Kidney Tissue

The % of administered dose recovered in kidney ranged from 0.12-0.51% for the various treatments. This data suggests a negligible amount of administered dose of $^3$H Kappa-peptide had accumulated in kidney tissue at t=6 h.

% Recovered in GI Tract

The % of administered dose recovered in the GI tract ranged from 27.10-89.26%. The GI tract can be further sub divided into GI tissue, GI contents and GI Washing, the range for each was 1.62-11.97%, 23.50-65.68% and 1.98-25.84% respectively. The data presented as % of administered dose recovered in the GI Tract represents the summation of 6 segments of GI tissue. Within the GI tract the highest levels of radioactivity were associated with the latter segments (refer to raw data table). The recovered radioactivity associated with GI segment 6 and its corresponding GI contents were higher than that observed for other segments.

In summary, the greatest % of administered dose of $^3$H Kappa-peptide-ligand conjugates were recovered primarily in the GI tract and more specifically in GI contents. Assuming that the $^3$H label remained attached to the Kappa-peptide, not all the administered dose was recovered suggesting that the Kappa-peptide-ligand-conjugates may have been excreted or had distributed to other sites within the rat. It must be noted that other potential sites for distribution, such as CNS tissue, weren't analysed in this study. These measurements are of $^3$H Kappa-peptide only and not of intact conjugate.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

That which is claimed is:

1. A composition comprising a translocating peptide, wherein said translocating peptide is a transport peptide or an extended peptide comprising said transport peptide, wherein said transport peptide is a retroinverted peptide and wherein the retroinverted peptide comprises a d-form amino acid sequence selected from the group consisting of a peptide of SEQ ID NOS:85 and 95-103 and the retroinverted sequence of SEQ ID NO:120.

2. The composition of claim 1, wherein the transport peptide is partially or completely cyclic.

3. The composition of claim 1, wherein the transport peptide is completely cyclic.

4. The composition of claim 1, wherein the carboxyl end group of the translocating peptide has been modified to create an amide group.

5. A chimeric polypeptide comprising (A) a translocating peptide selected from the group consisting of a transport peptide, an extended peptide comprising said transport peptide, and a transport-active fragment of at least 4 contiguous amino acids of said transport peptide, wherein said transport peptide is a retroinverted peptide and wherein the retroinverted peptide comprises a d-form amino acid sequence selected from the group consisting of a peptide of SEQ ID NOS:85 and 95-103 and the retroinverted sequence of SEQ ID NO:120, (B) a translocatable peptide, and (C) an amino acid linker sequence that directly links the translocating peptide to the translocatable peptide, wherein said translocatable peptide is between 3 and 200 amino acids, and wherein said amino acid linker sequence is between 1 and 20 amino acids.

6. The chimeric peptide of claim 5 wherein said translocatable peptide is between 3 and 30 amino acids.

7. The chimeric peptide of claim 5 wherein the translocatable peptide is an opioid peptide.

8. The chimeric peptide of claim 5 wherein said linker sequence is not more than 7 amino acids.

9. A composition comprising a translocating peptide, said translocating peptide selected from the group consisting of a transport peptide, an extended peptide comprising said transport peptide, and a transport-active fragment of at least 4 contiguous amino acids of said transport peptide, wherein said transport peptide a retroinverted peptide and wherein the retroinverted peptide comprises a d-form amino acid sequence selected from the group consisting of a peptide of SEQ ID NOS:85 and 95-103 and the retroinverted sequence of SEQ ID NO:120, and wherein said transport peptide is partially or completely cyclic.

10. A composition comprising a translocating peptide, said translocating peptide selected from the group consisting of a transport peptide, an extended peptide comprising said transport peptide, and a transport-active fragment of at least 4 contiguous amino acids of said transport peptide, wherein said transport peptide a retroinverted peptide and wherein the retroinverted peptide comprises a d-form amino acid sequence selected from the group consisting of a peptide of SEQ ID NOS:85 and 95-103 and the retroinverted sequence of SEQ ID NO:120, and wherein said transport-active fragment is partially or completely cyclic.

11. The composition of claim 9, wherein said transport peptide is completely cyclic.

12. The composition of claim 10, wherein said transport-active fragment is completely cyclic.

* * * * *

UNITED STATES PATENT AND TRADEMARK OFFICE

CERTIFICATE OF CORRECTION

PATENT NO. : 8,017,727 B2
APPLICATION NO. : 12/645922
DATED : September 13, 2011
INVENTOR(S) : O'Mahony et al.

It is certified that error appears in the above-identified patent and that said Letters Patent is hereby corrected as shown below:

On the Title Page:
Item (56) References Cited, Other Publications: Please add

-- Caulfield, M.†, "The 64-Kilodalton Membrane Protein of Bacillus Subtilis is also Present as a Multiprotein Complex on Membrane-Free Ribosomes", Proc. Natl. Acad. Sci. USA, Vol. 81, December 1984, pp. 7772-7776 -- and -- King, D. et al.; "A cleavage method which minimizes side reactions following Fmoc solid phase peptide synthesis"; Int. J. Peptide protein Res.; 36; 1990; pp. 255-266 --

In the Patent:
Column 11, Table 1, Column and Header, Lines 6-7, 10-43;

Please correct "K(ϵ-dansyl" to read -- K(ε-dansyl --

Line 49: Please correct "K(ϵ-dansyl" to read -- K(ε-dansyl --

Column 12, Table 2, Seq. Id. No. 26, sequence: Please correct "TNYTN-GCN" to read -- TNYTNGCN --

Column 13, Table 2, Seq. Id. No. 38, sequence:
Please correct "AARGCNGCNGTNYTNYTNCCNGTNYTNY TNGGNGCN"
to read -- AARGCNGCNGTNYTNYTNCCNGTNYTNY TNGCNGCN --

Table 2, Seq. Id. No. 39, last line of sequence: Please correct "NGGN" to read -- NGCN --

Signed and Sealed this
Seventeenth Day of April, 2012

David J. Kappos
*Director of the United States Patent and Trademark Office*

Column 13, Table 2, Seq. Id. No. 45, sequence:
Please correct "AARYTNGCNGTNYTNYTNGCNGCNCCN"
to read -- AARYTNCCNGTNYTNYTNGCNGCNCCN --

Column 18, Seq. Id. No. 58, $4^{th}$ line of sequence:
Please correct "qqflkrfaea" to read -- ggflkrfaea --

Column 19, Line 46: Please correct "(CH3–CH2–CH2–OH2–CH–"
to read -- (CH3–CH2–CH2–CH2–CH– --

Line 48: Please correct "NleS–CH3–CH2–CH2–OH2–CH–"
to read -- NleS–CH3–CH2–CH2–CH2–CH --

Column 23, Line 49: Please indent "Phase C" to indicate start of new paragraph

Column 25, Line 6: Please correct "28.1 μl/mg" to read -- 28.1 IU/mg --

Columns 33-34, Table 9: Please align the contents of Table 9 so they appear under the appropriate column headers as shown below:

| | Control | | Initial | | 1 hr | | 24 hr | |
|---|---|---|---|---|---|---|---|---|
| H-ffir-NH2 | RT | Area | RT | Area | RT | Area | RT | Area |
| | 0.467 | 347767 | 0.467 | 336841 | 0.467 | 360462 | 0.467 | 330859 |
| | | | 2.133 | 249457 | 2.117 | 285901 | | |
| | 2.333 | | 2.317 | 11107788 | 2.317 | 11691106 | 2.317 | 11215885 |

| Sequence | H— | f | f | i | r | —NH2 |
|---|---|---|---|---|---|---|
| %Compound | 1 hr | 105.25% | | | | |
| | 24 hr | 100.97% | | | | |

Column 33, Table 10, second heading: Please correct "# M.W."
to read -- # --

In the Claims:
Column 133, Claim 1, Line 27: Please correct "consisting of a peptide of"
to read -- consisting of --